(12) United States Patent
Gan et al.

(10) Patent No.: US 12,240,905 B2
(45) Date of Patent: Mar. 4, 2025

(54) ANTIBODIES BINDING CTLA-4 AND USES THEREOF

(71) Applicant: Harbour BioMed (Shanghai) Co., Ltd., Shanghai (CN)

(72) Inventors: Xin Gan, Shanghai (CN); Yun He, Shanghai (CN); Yuqiang Shen, Shanghai (CN); Jiuqiao Zhao, Newton, MA (US); Yiping Rong, Shanghai (CN); Frank Grosveld, Rotterdam (NL); Dubravka Drabek, Rotterdam (NL); Marinus (Rien) Van Haperen, Prinsenbeek (NL); Rick Janssens, Rotterdam (NL)

(73) Assignee: Harbour BioMed (Shanghai) Co., Ltd., Shanghai (CN)

( * ) Notice: Subject to any disclaimer, the term of this patent is extended or adjusted under 35 U.S.C. 154(b) by 903 days.

(21) Appl. No.: 17/375,940

(22) Filed: Jul. 14, 2021

(65) Prior Publication Data

US 2022/0002414 A1   Jan. 6, 2022

Related U.S. Application Data

(62) Division of application No. 16/224,825, filed on Dec. 19, 2018, now Pat. No. 11,098,122.

(60) Provisional application No. 62/607,917, filed on Dec. 20, 2017.

(51) Int. Cl.
  *C07K 16/28*  (2006.01)
  *A61K 39/00*  (2006.01)
  *A61P 35/00*  (2006.01)

(52) U.S. Cl.
  CPC ......... *C07K 16/2818* (2013.01); *A61P 35/00* (2018.01); *C07K 16/2878* (2013.01); *A61K 2039/505* (2013.01); *C07K 2317/21* (2013.01); *C07K 2317/24* (2013.01); *C07K 2317/33* (2013.01); *C07K 2317/51* (2013.01); *C07K 2317/52* (2013.01); *C07K 2317/565* (2013.01); *C07K 2317/70* (2013.01); *C07K 2317/72* (2013.01); *C07K 2317/732* (2013.01); *C07K 2317/76* (2013.01); *C07K 2317/92* (2013.01); *C07K 2317/94* (2013.01)

(58) Field of Classification Search
  CPC ............ C07K 16/2818; C07K 16/2878; C07K 2317/21; C07K 2317/24; C07K 2317/33; C07K 2317/51; C07K 2317/52; C07K 2317/565; C07K 2317/70; C07K 2317/72; C07K 2317/732; C07K 2317/76; C07K 2317/92; C07K 2317/94; A61P 35/00; A61K 2039/505
See application file for complete search history.

(56) References Cited

U.S. PATENT DOCUMENTS 7,193,064 B2 * 3/2007 Mikayama ............... A61P 37/04
                                                          435/69.6
2006/0240006 A1   10/2006 Chu et al.

FOREIGN PATENT DOCUMENTS

| CN | 102766210 A | 11/2012 |
|----|-------------|---------|
| CN | 103547595 A | 1/2014 |
| CN | 106046164 A | 10/2016 |
| CN | 106046165 A | 10/2016 |
| CN | 106188297 A | 12/2016 |
| CN | 106220732 A | 12/2016 |
| RU | 2346702 C2  | 2/2009 |
| RU | 2356579 C1  | 5/2009 |
| WO | 2017/198212 A1 | 11/2017 |

OTHER PUBLICATIONS

[No Author Listed], Harbour Antibodies Announces First U.S. Patent for Novel Transgenic Mouse Antibody Technology for Next Generation Therapeutic Antibody Discovery. Businesswire.com. Dec. 19, 2014. 2 pages. Accessible at businesswire.com/news/home/20141219005576/en/Harbour-Antibodies-Announces-First-U.S.-Patent-for-Novel-Transgenic-Mouse-Antibody-Technology-for-Next-Generation-Therapeutic-Antibody-Discovery.
Callahan et al., Anti-CTLA-4 Antibody Therapy: Immune Monitoring During Clinical Development of a Novel Immunotherapy. Semin Oncol. 2010;37:473-84.
Lederman et al., A single amino acid substitution in a common African allele of the CD4 molecule ablates binding of the monoclonal antibody, OKT4. Mol Immunol. Nov. 1991;28(11):1171-81.
Li et al., beta-Endorphin omission analogs: dissociation of immunoreactivity from other biological activities. Proc Natl Acad Sci U S A. Jun. 1980;77(6):3211-4.
Paul, Fundamental Immunology. Third Edition. 1993. Page 293.
Rudikoff et al., Single amino acid substitution altering antigen-binding specificity. Proc Natl Acad Sci U S A. Mar. 1982;79(6):1979-83.
Caljon et al., Affinity is an important determinant of the anti-trypanosome activity of nanobodies. PLoS Negl Trop Dis. 2012;6(11):e1902(1-8). Epub Nov. 15, 2012.

(Continued)

*Primary Examiner* — Brad Duffy
*Assistant Examiner* — Elizabeth A Shupe
(74) *Attorney, Agent, or Firm* — Mintz Levin Cohn Ferris Glovsky and Popeo, P.C.

(57) ABSTRACT

Disclosed are isolated monoclonal antibodies, comprising a CD152-binding domain, wherein the antibodies bind specifically to human CD152. Methods of making and using the antibodies to treat diseases including cancers and autoimmune diseases are also provided.

20 Claims, 13 Drawing Sheets

Specification includes a Sequence Listing.

(56) References Cited

OTHER PUBLICATIONS

Lazar et al., Engineered antibody Fc variants with enhanced effector function. Proc Natl Acad Sci U S A. Mar. 14, 2006;103(11):4005-10. Epub Mar. 6, 2006.
Mitchell et al., Comparative analysis of nanobody sequence and structure data. Proteins. Jul. 2018;86(7):697-706. Epub Apr. 15, 2018.

* cited by examiner

SEQUENCE LISTING

```
<160> NUMBER OF SEQ ID NOS: 200

<210> SEQ ID NO 1
<211> LENGTH: 1113
<212> TYPE: DNA
<213> ORGANISM: Homo Sapiens

<400> SEQUENCE: 1
atggagaccg acaccctgct gctgtgggtg ctgctgctgt gggtgcccgg atccaccggc      60
tctgaggtgc agctggtgga gattggagga ggcgagatcc agccgggggg gtccctgaga     120
ctctcgtgtg cagcctctgg gttcaacgtc agtaagaact acatgagttg ggtccgccag     180
gctccaggga aggggctgga gtgggtctca gtaatctata gtggtggtgg tacagaatac     240
gcagcctccg tgaagggccg atttaacatc tccagagaca gttccaagaa tatgttgtat     300
cttcaaatga acaacctgag agccgaggac acggccgtgt attattgtgc gagggccgtc     360
cccaggcccc atgggactga tatctggggc caagggacaa tggtcaccgt ctcttcagag     420
cccaaatctt gtgacaaaac tcacacatgc ccaccgtgcc cagcacctga actcctgggg     480
ggaccgtcag tcttcctctt ccccccaaaa cccaaggaca cctcatgat ctcccggacc     540 cctgaggtca catgcgtggt ggtggacgtg agccacgaag accctgaggt caagttcaac     600
tggtacgtgg acggcgtgga ggtgcataat gccaagacaa agccgcggga ggagcagtac     660
aacagcacgt accgggtggt cagcgtcctc accgtcctgc accaggactg gctgaatggc     720
aaggagtaca agtgcaaggt ctccaacaaa gccctcccag ccccatcga gaaaaccatc     780
```

-continued

```
tccaaagcca aagggcagcc ccgagaacca caggtgtaca ccctgccccc atcccgggag    840
gagatgacca agaaccaggt cagcctgacc tgcctggtca aaggcttcta tcccagcgac    900
atcgccgtgg agtgggagag caatgggcag ccggagaaca actacaagac cacgcctccc    960
gtgctggact ccgacggctc cttcttcctc tacagcaagc tcaccgtgga caagagcagg   1020
tggcagcagg ggaacgtctt ctcatgctcc gtgatgcatg aggctctgca caaccactac   1080
acgcagaaga gcctctccct gtctccgggt aaa                                1113
```

<210> SEQ ID NO 2
<211> LENGTH: 371
<212> TYPE: PRT
<213> ORGANISM: Homo Sapiens

<400> SEQUENCE: 2

Met Glu Thr Asp Thr Leu Leu Leu Trp Val Leu Leu Leu Trp Val Pro
1               5                   10                  15

Gly Ser Thr Gly Ser Glu Val Gln Leu Val Glu Ile Gly Gly Gly Glu
            20                  25                  30

Ile Gln Pro Gly Gly Ser Leu Arg Leu Ser Cys Ala Ala Ser Gly Phe
        35                  40                  45

Asn Val Ser Lys Asn Tyr Met Ser Trp Val Arg Gln Ala Pro Gly Lys
    50                  55                  60

Gly Leu Glu Trp Val Ser Val Ile Tyr Ser Gly Gly Thr Glu Tyr
65                  70                  75                  80

Ala Ala Ser Val Lys Gly Arg Phe Asn Ile Ser Arg Asp Ser Ser Lys
                85                  90                  95

Asn Met Leu Tyr Leu Gln Met Asn Asn Leu Arg Ala Glu Asp Thr Ala
            100                 105                 110

Val Tyr Tyr Cys Ala Arg Ala Val Pro Arg Pro His Gly Thr Asp Ile
        115                 120                 125

Trp Gly Gln Gly Thr Met Val Thr Val Ser Ser Glu Pro Lys Ser Cys
    130                 135                 140

Asp Lys Thr His Thr Cys Pro Pro Cys Pro Ala Pro Glu Leu Leu Gly
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
        195                 200                 205

His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ala Pro Ile
                245                 250                 255

Glu Lys Thr Ile Ser Lys Ala Lys Gly Gln Pro Arg Glu Pro Gln Val
            260                 265                 270

Tyr Thr Leu Pro Pro Ser Arg Glu Glu Met Thr Lys Asn Gln Val Ser
        275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Asn Tyr Lys Thr Thr Pro Pro

```
                305                 310                 315                 320
Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
                340                 345                 350

His Glu Ala Leu His Asn His Tyr Thr Gln Lys Ser Leu Ser Leu Ser
                355                 360                 365

Pro Gly Lys
        370

<210> SEQ ID NO 3
<211> LENGTH: 118
<212> TYPE: PRT
<213> ORGANISM: Homo Sapiens

<400> SEQUENCE: 3

Glu Val Gln Leu Val Glu Ile Gly Gly Gly Glu Ile Gln Pro Gly Gly
1               5                   10                  15

Ser Leu Arg Leu Ser Cys Ala Ala Ser Gly Phe Asn Val Ser Lys Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Thr Glu Tyr Ala Ala Ser Val Lys
    50                  55                  60

Gly Arg Phe Asn Ile Ser Arg Asp Ser Ser Lys Asn Met Leu Tyr Leu
65                  70                  75                  80

Gln Met Asn Asn Leu Arg Ala Glu Asp Thr Ala Val Tyr Tyr Cys Ala
                85                  90                  95

Arg Ala Val Pro Arg Pro His Gly Thr Asp Ile Trp Gly Gln Gly Thr
            100                 105                 110

Met Val Thr Val Ser Ser
        115

<210> SEQ ID NO 4
<211> LENGTH: 10
<212> TYPE: PRT
<213> ORGANISM: Homo Sapiens

<400> SEQUENCE: 4

Gly Phe Asn Val Ser Lys Asn Tyr Met Ser
1               5                   10

<210> SEQ ID NO 5
<211> LENGTH: 16
<212> TYPE: PRT
<213> ORGANISM: Homo Sapiens

<400> SEQUENCE: 5

Val Ile Tyr Ser Gly Gly Gly Thr Glu Tyr Ala Ala Ser Val Lys Gly
1               5                   10                  15

<210> SEQ ID NO 6
<211> LENGTH: 10
<212> TYPE: PRT
<213> ORGANISM: Homo Sapiens

<400> SEQUENCE: 6

Ala Val Pro Arg Pro His Gly Thr Asp Ile
1               5                   10
```

<210> SEQ ID NO 7
<211> LENGTH: 1116
<212> TYPE: DNA
<213> ORGANISM: Homo Sapiens

<400> SEQUENCE: 7

| | | | | | |
|---|---|---|---|---|---|
| atggagaccg | acaccctgct | gctgtgggtg | ctgctgctgt | gggtgcccgg | atccaccggc | 60 |
| tctgaggtgc | agctggcgga | gactggagga | ggcttgatcc | agcctggggg | gtccctgaga | 120 |
| ctctcctgtg | cagtctctgg | gttcaatgtc | agtaagaatt | acatgagctg | ggtccgccag | 180 |
| gttccaggga | aggggctgga | gtgggtcgca | gttgtttata | gcggtggtag | caaaacctac | 240 |
| gcagactccg | tgaagggccg | attcatcctc | tccagagaca | attccgacaa | cacactgtat | 300 |
| cttcaaatga | acaacctgag | agccgaggac | acggccgtgt | attactgtgc | gagagccgtt | 360 |
| cctcattccc | ccagttcttt | tgatatctgg | ggccaaggga | caatggtcac | cgtctcttca | 420 |
| gagcccaaat | cttgtgacaa | aactcacaca | tgcccaccgt | gcccagcacc | tgaactcctg | 480 |
| gggggaccgt | cagtcttcct | cttccccca | aacccaagg | acaccctcat | gatctcccgg | 540 |
| accccctgagg | tcacatgcgt | ggtggtggac | gtgagccacg | aagaccctga | ggtcaagttc | 600 |
| aactggtacg | tggacggcgt | ggaggtgcat | aatgccaaga | caaagccgcg | ggaggagcag | 660 |
| tacaacagca | cgtaccgggt | ggtcagcgtc | ctcaccgtcc | tgcaccagga | ctggctgaat | 720 |
| ggcaaggagt | acaagtgcaa | ggtctccaac | aaagccctcc | cagcccccat | cgagaaaacc | 780 |
| atctccaaag | ccaaagggca | gccccgagaa | ccacaggtgt | acaccctgcc | cccatcccgg | 840 |
| gaggagatga | ccaagaacca | ggtcagcctg | acctgcctgg | tcaaaggctt | ctatcccagc | 900 |
| gacatcgccg | tggagtggga | gagcaatggg | cagccggaga | caactacaa | gaccacgcct | 960 |
| cccgtgctgg | actccgacgg | ctccttcttc | ctctacagca | agctcaccgt | ggacaagagc | 1020 |
| aggtggcagc | aggggaacgt | cttctcatgc | tccgtgatgc | atgaggctct | gcacaaccac | 1080 |
| tacacgcaga | agagcctctc | cctgtctccg | ggtaaa | | | 1116 |

<210> SEQ ID NO 8
<211> LENGTH: 372
<212> TYPE: PRT
<213> ORGANISM: Homo Sapiens

<400> SEQUENCE: 8

Met Glu Thr Asp Thr Leu Leu Leu Trp Val Leu Leu Leu Trp Val Pro
1               5                   10                  15

Gly Ser Thr Gly Ser Glu Val Gln Leu Ala Glu Thr Gly Gly Gly Leu
            20                  25                  30

Ile Gln Pro Gly Gly Ser Leu Arg Leu Ser Cys Ala Val Ser Gly Phe
        35                  40                  45

Asn Val Ser Lys Asn Tyr Met Ser Trp Val Arg Gln Val Pro Gly Lys
    50                  55                  60

Gly Leu Glu Trp Val Ala Val Val Tyr Ser Gly Gly Ser Lys Thr Tyr
65                  70                  75                  80

Ala Asp Ser Val Lys Gly Arg Phe Ile Leu Ser Arg Asp Asn Ser Asp
                85                  90                  95

Asn Thr Leu Tyr Leu Gln Met Asn Asn Leu Arg Ala Glu Asp Thr Ala
            100                 105                 110

Val Tyr Tyr Cys Ala Arg Ala Val Pro His Ser Pro Ser Ser Phe Asp
        115                 120                 125

Ile Trp Gly Gln Gly Thr Met Val Thr Val Ser Ser Glu Pro Lys Ser

```
            130                 135                 140
Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 9
<211> LENGTH: 119
<212> TYPE: PRT
<213> ORGANISM: Homo Sapiens

<400> SEQUENCE: 9

Glu Val Gln Leu Ala Glu Thr Gly Gly Gly Leu Ile Gln Pro Gly Gly
1               5                   10                  15

Ser Leu Arg Leu Ser Cys Ala Val Ser Gly Phe Asn Val Ser Lys Asn
            20                  25                  30

Tyr Met Ser Trp Val Arg Gln Val Pro Gly Lys Gly Leu Glu Trp Val
        35                  40                  45

Ala Val Val Tyr Ser Gly Gly Ser Lys Thr Tyr Ala Asp Ser Val Lys
    50                  55                  60

Gly Arg Phe Ile Leu Ser Arg Asp Asn Ser Asp Asn Thr Leu Tyr Leu
65                  70                  75                  80

Gln Met Asn Asn Leu Arg Ala Glu Asp Thr Ala Val Tyr Tyr Cys Ala
                85                  90                  95

Arg Ala Val Pro His Ser Pro Ser Phe Asp Ile Trp Gly Gln Gly
            100                 105                 110

Thr Met Val Thr Val Ser Ser
        115
```

<210> SEQ ID NO 10
<211> LENGTH: 10
<212> TYPE: PRT
<213> ORGANISM: Homo Sapiens

<400> SEQUENCE: 10

Gly Phe Asn Val Ser Lys Asn Tyr Met Ser
1               5                   10

<210> SEQ ID NO 11
<211> LENGTH: 16
<212> TYPE: PRT
<213> ORGANISM: Homo Sapiens)

<400> SEQUENCE: 11

Val Val Tyr Ser Gly Gly Ser Lys Thr Tyr Ala Asp Ser Val Lys Gly
1               5                   10                  15

<210> SEQ ID NO 12
<211> LENGTH: 11
<212> TYPE: PRT
<213> ORGANISM: Homo Sapiens

<400> SEQUENCE: 12

Ala Val Pro His Ser Pro Ser Ser Phe Asp Ile
1               5                   10

<210> SEQ ID NO 13
<211> LENGTH: 1116
<212> TYPE: DNA
<213> ORGANISM: Homo Sapiens)

<400> SEQUENCE: 13

```
atggagaccg acaccctgct gctgtgggtg ctgctgctgt gggtgcccgg atccaccggc    60
tctgaggtgc agctggagga gactggagga gacttgatcc agccgggggg gtccctgaga   120
ctctcctgta cagcctctgg gtttaacgtc agtagaatct acatgagctg ggtccgccag   180
gctccaggga aggggctgga gtgggtctca gtgatttata gcggtggaag tatatattac   240
gcagattccg tgaggggccg atttaccatc tccagagaca gttccacgaa cacggtgttt   300
cttcaaatga acagcctgag agccgaggac tcggccgtgt attactgtgc gagagccgtc   360
ccaagtgccc ctagttcttt tgatatctgg ggccaaggga caatggtcac cgtctcttca   420
gagcccaaat cttgtgacaa aactcacaca tgcccaccgt gcccagcacc tgaactcctg   480
gggggaccgt cagtcttcct cttcccccca aaacccaagg acaccctcat gatctcccgg   540
acccctgagg tcacatgcgt ggtggtggac gtgagccacg aagaccctga ggtcaagttc   600
aactggtacg tggacggcgt ggaggtgcat aatgccaaga caaagccgcg ggaggagcag   660
tacaacagca cgtaccgggt ggtcagcgtc ctcaccgtcc tgcaccagga ctggctgaat   720
ggcaaggagt acaagtgcaa ggtctccaac aaagccctcc cagcccccat cgagaaaacc   780
atctccaaag ccaaagggca gccccgagaa ccacaggtgt acaccctgcc cccatcccgg   840
gaggagatga ccaagaacca ggtcagcctg acctgcctgg tcaaaggctt ctatcccagc   900
gacatcgccg tggagtggga gagcaatggg cagccggaga caactacaa gaccacgcct   960
cccgtgctgg actccgacgg ctccttcttc ctctacagca agctcaccgt ggacaagagc  1020
aggtggcagc aggggaacgt cttctcatgc tccgtgatgc atgaggctct gcacaaccac  1080
tacacgcaga agagcctctc cctgtctccg ggtaaa                            1116
```

<210> SEQ ID NO 14
<211> LENGTH: 372
<212> TYPE: PRT
<213> ORGANISM: Homo Sapiens)

<400> SEQUENCE: 14

```
Met Glu Thr Asp Thr Leu Leu Leu Trp Val Leu Leu Leu Trp Val Pro
1               5                   10                  15

Gly Ser Thr Gly Ser Glu Val Gln Leu Glu Glu Thr Gly Gly Asp Leu
            20                  25                  30

Ile Gln Pro Gly Gly Ser Leu Arg Leu Ser Cys Thr Ala Ser Gly Phe
        35                  40                  45

Asn Val Ser Arg Ile Tyr Met Ser Trp Val Arg Gln Ala Pro Gly Lys
50                  55                  60

Gly Leu Glu Trp Val Ser Val Ile Tyr Ser Gly Gly Ser Ile Tyr Tyr
65                  70                  75                  80

Ala Asp Ser Val Arg Gly Arg Phe Thr Ile Ser Arg Asp Ser Ser Thr
                85                  90                  95

Asn Thr Val Phe Leu Gln Met Asn Ser Leu Arg Ala Glu Asp Ser Ala
            100                 105                 110

Val Tyr Tyr Cys Ala Arg Ala Val Pro Ser Ala Pro Ser Ser Phe Asp
        115                 120                 125

Ile Trp Gly Gln Gly Thr Met Val Thr Val Ser Ser Glu Pro Lys Ser
130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
370
```

<210> SEQ ID NO 15
<211> LENGTH: 119
<212> TYPE: PRT
<213> ORGANISM: Homo Sapiens

<400> SEQUENCE: 15

Glu Val Gln Leu Glu Glu Thr Gly Gly Asp Leu Ile Gln Pro Gly Gly
1               5                   10                  15

Ser Leu Arg Leu Ser Cys Thr Ala Ser Gly Phe Asn Val Ser Arg Ile
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Ile Tyr Tyr Ala Asp Ser Val Arg
    50                  55                  60

Gly Arg Phe Thr Ile Ser Arg Asp Ser Ser Thr Asn Thr Val Phe Leu
65                  70                  75                  80

Gln Met Asn Ser Leu Arg Ala Glu Asp Ser Ala Val Tyr Tyr Cys Ala
                85                  90                  95

Arg Ala Val Pro Ser Ala Pro Ser Ser Phe Asp Ile Trp Gly Gln Gly
            100                 105                 110

Thr Met Val Thr Val Ser Ser
        115

<210> SEQ ID NO 16
<211> LENGTH: 10
<212> TYPE: PRT
<213> ORGANISM: Homo Sapiens

<400> SEQUENCE: 16

Gly Phe Asn Val Ser Arg Ile Tyr Met Ser
1               5                   10

<210> SEQ ID NO 17
<211> LENGTH: 16
<212> TYPE: PRT
<213> ORGANISM: Homo Sapiens

<400> SEQUENCE: 17

Val Ile Tyr Ser Gly Gly Ser Ile Tyr Tyr Ala Asp Ser Val Arg Gly
1               5                   10                  15

<210> SEQ ID NO 18
<211> LENGTH: 11
<212> TYPE: PRT
<213> ORGANISM: Homo Sapiens

<400> SEQUENCE: 18

Ala Val Pro Ser Ala Pro Ser Ser Phe Asp Ile
1               5                   10

<210> SEQ ID NO 19
<211> LENGTH: 1119
<212> TYPE: DNA
<213> ORGANISM: Homo Sapiens

<400> SEQUENCE: 19
atggagaccg acaccctgct gctgtgggtg ctgctgctgt gggtgcccgg atccaccggc      60
tctgaggtgc agctggtgga gtccggggga ggcttagttc agcctggggg gtccctgaga     120
ctctcctgtg cagcctctgg attcaccttc agtaactact ggatgcactg ggtccgccaa     180

-continued

```
gctccaggga agggctggt gtgggtctca cgtattaata gtgatgggag taacacaacc    240
tacgcggact ccgtgaaggg ccgattcacc atctccagag acaacgccaa gaacacgctg    300
tatctgcaaa tgaacagtct gagagccgag gacacggctg tgtattactg tgcaagatgg    360
ttcggggagc actactacgg aatggacgtc tggggccaag ggaccacggt caccgtctct    420
tcagagccca aatcttgtga caaaactcac acatgcccac cgtgcccagc acctgaactc    480 ctgggggac cgtcagtctt cctcttcccc ccaaaaccca aggacaccct catgatctcc    540
cggacccctg aggtcacatg cgtggtggtg gacgtgagcc acgaagaccc tgaggtcaag    600
ttcaactggt acgtggacgg cgtggaggtg cataatgcca agacaaagcc gcgggaggag    660
cagtacaaca gcacgtaccg ggtggtcagc gtcctcaccg tcctgcacca ggactggctg    720
aatggcaagg agtacaagtg caaggtctcc aacaaagccc tcccagcccc catcgagaaa    780
accatctcca aagccaaagg gcagccccga gaaccacagg tgtacaccct gcccccatcc    840
cgggaggaga tgaccaagaa ccaggtcagc ctgacctgcc tggtcaaagg cttctatccc    900
agcgacatcg ccgtggagtg ggagagcaat gggcagccgg agaacaacta caagaccacg    960
cctcccgtgc tggactccga cggctccttc ttcctctaca gcaagctcac cgtggacaag   1020
agcaggtggc agcaggggaa cgtcttctca tgctccgtga tgcatgaggc tctgcacaac   1080
cactacacgc agaagagcct ctccctgtct ccgggtaaa                          1119
```

<210> SEQ ID NO 20
<211> LENGTH: 373
<212> TYPE: PRT
<213> ORGANISM: Homo Sapiens

<400> SEQUENCE: 20

```
Met Glu Thr Asp Thr Leu Leu Leu Trp Val Leu Leu Leu Trp Val Pro
1               5                   10                  15

Gly Ser Thr Gly Ser Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Asn Tyr Trp Met His Trp Val Arg Gln Ala Pro Gly Lys
    50                  55                  60

Gly Leu Val Trp Val Ser Arg Ile Asn Ser Asp Gly Ser Asn Thr Thr
65                  70                  75                  80

Tyr Ala Asp Ser Val Lys Gly Arg Phe Thr Ile Ser Arg Asp Asn Ala
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Trp Phe Gly Glu His Tyr Tyr Gly Met
        115                 120                 125

Asp Val Trp Gly Gln Gly Thr Thr Val Thr Val Ser Ser Glu Pro Lys
    130                 135                 140

Ser Cys Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205
```

```
Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Glu Glu Met Thr Lys Asn Gln
        275                 280                 285

Val Ser Leu Thr Cys Leu Val Lys Gly Phe Tyr Pro Ser Asp Ile Ala
290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
        355                 360                 365

Leu Ser Pro Gly Lys
    370

<210> SEQ ID NO 21
<211> LENGTH: 120
<212> TYPE: PRT
<213> ORGANISM: Homo Sapiens

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Asn Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Phe Gly Glu His Tyr Tyr Gly Met Asp Val Trp Gly Gln
            100                 105                 110

Gly Thr Thr Val Thr Val Ser Ser
        115                 120

<210> SEQ ID NO 22
<211> LENGTH: 10
<212> TYPE: PRT
<213> ORGANISM: Homo Sapiens

<400> SEQUENCE: 22

Gly Phe Thr Phe Ser Asn Tyr Trp Met His
1               5                   10

<210> SEQ ID NO 23
```

```
<211> LENGTH: 17
<212> TYPE: PRT
<213> ORGANISM: Homo Sapiens

<400> SEQUENCE: 23

Arg Ile Asn Ser Asp Gly Ser Asn Thr Thr Tyr Ala Asp Ser Val Lys
1               5                   10                  15

Gly

<210> SEQ ID NO 24
<211> LENGTH: 11
<212> TYPE: PRT
<213> ORGANISM: Homo Sapiens

<400> SEQUENCE: 24

Trp Phe Gly Glu His Tyr Tyr Gly Met Asp Val
1               5                   10

<210> SEQ ID NO 25
<211> LENGTH: 1116
<212> TYPE: DNA
<213> ORGANISM: Homo Sapiens

<400> SEQUENCE: 25
```

| | | | | | |
|---|---|---|---|---|---|
| atggagaccg | acaccctgct | gctgtgggtg | ctgctgctgt | gggtgcccgg | atccaccggc        60 |
| tctgaggtgc | agctggtgga | gactggagga | gggctgatcc | agccgggggg | gtccctgaga       120 |
| ctctcctgtg | cagtctctgg | gttcaccgtc | agaaacaact | acatgagctg | ggcccgccag       180 |
| gttccaggga | agggactgga | gtgggtctca | gttatttata | gcggtgggag | tataacctac       240 |
| gcagactccg | tgaagggccg | attcatcatc | tccagagaca | attccaacaa | cacgctatat       300 |
| cttcaaatga | acggtctgag | agccgaggac | acggccgtat | attactgtgc | gagagccgtc       360 |
| ccacatgccc | caagtgcttt | tgacatctgg | ggccagggga | caatggtcac | cgtctcttca       420 |
| gagcccaaat | cttgtgacaa | aactcacaca | tgcccaccgt | gcccagcacc | tgaactcctg       480 |
| gggggaccgt | cagtcttcct | cttccccccca | aaacccaagg | acaccctcat | gatctcccgg       540 |
| acccctgagg | tcacatgcgt | ggtggtggac | gtgagccacg | aagaccctga | ggtcaagttc       600 |
| aactggtacg | tggacggcgt | ggaggtgcat | aatgccaaga | caaagccgcg | ggaggagcag       660 |
| tacaacagca | cgtaccgggt | ggtcagcgtc | ctcaccgtcc | tgcaccagga | ctggctgaat       720 |
| ggcaaggagt | acaagtgcaa | ggtctccaac | aaagccctcc | cagcccccat | cgagaaaacc       780 |
| atctccaaag | ccaaagggca | gccccgagaa | ccacaggtgt | acaccctgcc | cccatcccgg       840 |
| gaggagatga | ccaagaacca | ggtcagcctg | acctgcctgg | tcaaaggctt | ctatcccagc       900 |
| gacatcgccg | tggagtggga | gagcaatggg | cagccggaga | acaactacaa | gaccacgcct       960 |
| cccgtgctgg | actccgacgg | ctccttcttc | ctctacagca | agctcaccgt | ggacaagagc      1020 |
| aggtggcagc | aggggaacgt | cttctcatgc | tccgtgatgc | atgaggctct | gcacaaccac      1080 |
| tacacgcaga | agagcctctc | cctgtctccg | ggtaaa     |            |                1116 |

```
<210> SEQ ID NO 26
<211> LENGTH: 372
<212> TYPE: PRT
<213> ORGANISM: Homo Sapiens

<400> SEQUENCE: 26

Met Glu Thr Asp Thr Leu Leu Leu Trp Val Leu Leu Leu Trp Val Pro
1               5                   10                  15
```

```
Gly Ser Thr Gly Ser Glu Val Gln Leu Val Glu Gly Gly Leu
            20                  25                  30

Ile Gln Pro Gly Gly Ser Leu Arg Leu Ser Cys Ala Val Ser Gly Phe
            35                  40                  45

Thr Val Arg Asn Asn Tyr Met Ser Trp Ala Arg Gln Val Pro Gly Lys
        50                  55                  60

Gly Leu Glu Trp Val Ser Val Ile Tyr Ser Gly Ser Ile Thr Tyr
65                  70                  75                  80

Ala Asp Ser Val Lys Gly Arg Phe Ile Ile Ser Arg Asp Asn Ser Asn
                85                  90                  95

Asn Thr Leu Tyr Leu Gln Met Asn Gly Leu Arg Ala Glu Asp Thr Ala
            100                 105                 110

Val Tyr Tyr Cys Ala Arg Ala Val Pro His Ala Pro Ser Ala Phe Asp
        115                 120                 125

Ile Trp Gly Gln Gly Thr Met Val Thr Val Ser Ser Glu Pro Lys Ser
130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 27
<211> LENGTH: 119
<212> TYPE: PRT
<213> ORGANISM: Homo Sapiens

<400> SEQUENCE: 27

Glu Val Gln Leu Val Glu Thr Gly Gly Gly Leu Ile Gln Pro Gly Gly
1               5                   10                  15
```

Ser Leu Arg Leu Ser Cys Ala Val Ser Gly Phe Thr Val Arg Asn Asn
                20                  25                  30

Tyr Met Ser Trp Ala Arg Gln Val Pro Gly Lys Gly Leu Glu Trp Val
        35                  40                  45

Ser Val Ile Tyr Ser Gly Gly Ser Ile Thr Tyr Ala Asp Ser Val Lys
    50                  55                  60

Gly Arg Phe Ile Ile Ser Arg Asp Asn Ser Asn Asn Thr Leu Tyr Leu
65                  70                  75                  80

Gln Met Asn Gly Leu Arg Ala Glu Asp Thr Ala Val Tyr Tyr Cys Ala
                85                  90                  95

Arg Ala Val Pro His Ala Pro Ser Ala Phe Asp Ile Trp Gly Gln Gly
            100                 105                 110

Thr Met Val Thr Val Ser Ser
            115

<210> SEQ ID NO 28
<211> LENGTH: 10
<212> TYPE: PRT
<213> ORGANISM: Homo Sapiens

<400> SEQUENCE: 28

Gly Phe Thr Val Arg Asn Asn Tyr Met Ser
1               5                   10

<210> SEQ ID NO 29
<211> LENGTH: 16
<212> TYPE: PRT
<213> ORGANISM: Homo Sapiens

<400> SEQUENCE: 29

Val Ile Tyr Ser Gly Gly Ser Ile Thr Tyr Ala Asp Ser Val Lys Gly
1               5                   10                  15

<210> SEQ ID NO 30
<211> LENGTH: 11
<212> TYPE: PRT
<213> ORGANISM: Homo Sapiens

<400> SEQUENCE: 30

Ala Val Pro His Ala Pro Ser Ala Phe Asp Ile
1               5                   10

<210> SEQ ID NO 31
<211> LENGTH: 1113
<212> TYPE: DNA
<213> ORGANISM: Homo Sapiens

<400> SEQUENCE: 31
atggagaccg acaccctgct gctgtgggtg ctgctgctgt gggtgcccgg atccaccggc      60
tctgaggtgc agctggtgga gactggagga ggcttaatcc agcctggggg gtccctgaga     120
ctctcctgtg cagcctctgg gctcaatgtc agtaggcact acttaagctg gtccgccag     180 gctccaggga aggggctgga gtgggtcgca gtaatttata gcggtggtgg tatagagtac     240
gtagactccg tgaagggccg attcaccatc tccagagaca tgccaacaa cacgctgtat     300 cttcaaatga agcctgag aaccgaagac tcggccgtat attactgtgc gcgggccatt     360
cccagacccc atggttcgga tatctgggc caagggacaa tggtcaccgt ctcttcagag     420
cccaaatctt gtgacaaaac tcacacatgc ccaccgtgcc cagcacctga actcctgggg     480

```
ggaccgtcag tcttcctctt ccccccaaaa cccaaggaca ccctcatgat ctcccggacc    540
cctgaggtca catgcgtggt ggtggacgtg agccacgaag accctgaggt caagttcaac    600
tggtacgtgg acggcgtgga ggtgcataat gccaagacaa agccgcggga ggagcagtac    660
aacagcacgt accgggtggt cagcgtcctc accgtcctgc accaggactg gctgaatggc    720
aaggagtaca agtgcaaggt ctccaacaaa gccctcccag cccccatcga gaaaaccatc    780
tccaaagcca agggcagccc cgagaaccca caggtgtaca ccctgccccc atcccgggag    840
gagatgacca agaaccaggt cagcctgacc tgcctggtca aaggcttcta tcccagcgac    900
atcgccgtgg agtgggagag caatgggcag ccggagaaca actacaagac cacgcctccc    960
gtgctggact ccgacggctc cttcttcctc tacagcaagc tcaccgtgga caagagcagg   1020
tggcagcagg ggaacgtctt ctcatgctcc gtgatgcatg aggctctgca caaccactac   1080
acgcagaaga gcctctccct gtctccgggt aaa                                1113
```

```
<210> SEQ ID NO 32
<211> LENGTH: 371
<212> TYPE: PRT
<213> ORGANISM: Homo Sapiens

<400> SEQUENCE: 32
```

```
Met Glu Thr Asp Thr Leu Leu Leu Trp Val Leu Leu Leu Trp Val Pro
  1               5                  10                  15

Gly Ser Thr Gly Ser Glu Val Gln Leu Val Glu Thr Gly Gly Gly Leu
             20                  25                  30

Ile Gln Pro Gly Gly Ser Leu Arg Leu Ser Cys Ala Ala Ser Gly Leu
         35                  40                  45

Asn Val Ser Arg His Tyr Leu Ser Trp Val Arg Gln Ala Pro Gly Lys
     50                  55                  60

Gly Leu Glu Trp Val Ala Val Ile Tyr Ser Gly Gly Ile Glu Tyr
 65                  70                  75                  80

Val Asp Ser Val Lys Gly Arg Phe Thr Ile Ser Arg Asp Asn Ala Asn
                 85                  90                  95

Asn Thr Leu Tyr Leu Gln Met Arg Ser Leu Arg Thr Glu Asp Ser Ala
            100                 105                 110

Val Tyr Tyr Cys Ala Arg Ala Ile Pro Arg Pro His Gly Ser Asp Ile
        115                 120                 125

Trp Gly Gln Gly Thr Met Val Thr Val Ser Ser Glu Pro Lys Ser Cys
    130                 135                 140

Asp Lys Thr His Thr Cys Pro Pro Cys Pro Ala Pro Glu Leu Leu Gly
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
        195                 200                 205

His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ala Pro Ile
                245                 250                 255

Glu Lys Thr Ile Ser Lys Ala Lys Gly Gln Pro Arg Glu Pro Gln Val
```

```
                    260                 265                 270
Tyr Thr Leu Pro Pro Ser Arg Glu Glu Met Thr Lys Asn Gln Val Ser
                275                 280                 285

Leu Thr Cys Leu Val Lys Gly Phe Tyr Pro Ser Asp Ile Ala Val Glu
        290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
                340                 345                 350

His Glu Ala Leu His Asn His Tyr Thr Gln Lys Ser Leu Ser Leu Ser
            355                 360                 365

Pro Gly Lys
        370

<210> SEQ ID NO 33
<211> LENGTH: 118
<212> TYPE: PRT
<213> ORGANISM: Homo Sapiens

<400> SEQUENCE: 33

Glu Val Gln Leu Val Glu Thr Gly Gly Gly Leu Ile Gln Pro Gly Gly
1               5                   10                  15

Ser Leu Arg Leu Ser Cys Ala Ala Ser Gly Leu Asn Val Ser Arg His
            20                  25                  30

Tyr Leu Ser Trp Val Arg Gln Ala Pro Gly Lys Gly Leu Glu Trp Val
        35                  40                  45

Ala Val Ile Tyr Ser Gly Gly Gly Ile Glu Tyr Val Asp Ser Val Lys
    50                  55                  60

Gly Arg Phe Thr Ile Ser Arg Asp Asn Ala Asn Asn Thr Leu Tyr Leu
65                  70                  75                  80

Gln Met Arg Ser Leu Arg Thr Glu Asp Ser Ala Val Tyr Tyr Cys Ala
                85                  90                  95

Arg Ala Ile Pro Arg Pro His Gly Ser Asp Ile Trp Gly Gln Gly Thr
            100                 105                 110

Met Val Thr Val Ser Ser
        115

<210> SEQ ID NO 34
<211> LENGTH: 10
<212> TYPE: PRT
<213> ORGANISM: Homo Sapiens

<400> SEQUENCE: 34

Gly Leu Asn Val Ser Arg His Tyr Leu Ser
1               5                   10

<210> SEQ ID NO 35
<211> LENGTH: 16
<212> TYPE: PRT
<213> ORGANISM: Homo Sapiens

<400> SEQUENCE: 35

Val Ile Tyr Ser Gly Gly Gly Ile Glu Tyr Val Asp Ser Val Lys Gly
1               5                   10                  15

<210> SEQ ID NO 36
```

```
<211> LENGTH: 10
<212> TYPE: PRT
<213> ORGANISM: Homo Sapiens

<400> SEQUENCE: 36

Ala Ile Pro Arg Pro His Gly Ser Asp Ile
1               5                   10

<210> SEQ ID NO 37
<211> LENGTH: 1116
<212> TYPE: DNA
<213> ORGANISM: Homo Sapiens

<400> SEQUENCE: 37
atggagaccg acaccctgct gctgtgggtg ctgctgctgt gggtgcccgg atccaccggc      60
tctgaggtgc agctggtgga gactggagga ggcttgatcc agcctggggg gtccctgaga     120
ctctcctgtg cagcctctgg gttcaccgtc agtagcaact acatgagctg gtccgccag     180 gctccaggga aggggctgga gtgggtctca gttatttata gcggtggtag cacatactac     240
gcagactccg tgaagggccg attcaccatc tccagagaca attccaagaa cacgctgtat     300
cttcaaatga gcaacctgac cgccgaggac acggccgtgt attactgtgc gagagccgtt     360 cccccactccc ccagtgcttt tgataggtgg ggccagggaa ccctggtcac cgtctcttca     420
gagcccaaat cttgtgacaa aactcacaca tgcccaccgt gcccagcacc tgaactcctg     480
gggggaccgt cagtcttcct cttcccccca aaacccaagg acaccctcat gatctcccgg     540
accctgaggg tcacatgcgt ggtggtggac gtgagccacg aagaccctga ggtcaagttc     600
aactggtacg tggacggcgt ggaggtgcat aatgccaaga caaagccgcg ggaggagcag     660
tacaacagca cgtaccgggt ggtcagcgtc ctcaccgtcc tgcaccagga ctggctgaat     720
ggcaaggagt acaagtgcaa ggtctccaac aaagccctcc cagcccccat cgagaaaacc     780
atctccaaag ccaaagggca gccccgagaa ccacaggtgt acaccctgcc cccatcccgg     840
gaggagatga ccaagaacca ggtcagcctg acctgcctgg tcaaaggctt ctatcccagc     900
gacatcgccg tggagtggga gagcaatggg cagccggaga caactacaa gaccacgcct     960 cccgtgctgg actccgacgg ctccttcttc ctctacagca agctcaccgt ggacaagagc    1020
aggtggcagc aggggaacgt cttctcatgc tccgtgatgc atgaggctct gcacaaccac    1080
tacacgcaga agagcctctc cctgtctccg ggtaaa                              1116

<210> SEQ ID NO 38
<211> LENGTH: 372
<212> TYPE: PRT
<213> ORGANISM: Homo Sapiens

<400> SEQUENCE: 38

Met Glu Thr Asp Thr Leu Leu Leu Trp Val Leu Leu Leu Trp Val Pro
1               5                   10                  15

Gly Ser Thr Gly Ser Glu Val Gln Leu Val Glu Thr Gly Gly Gly Leu
            20                  25                  30

Ile Gln Pro Gly Gly Ser Leu Arg Leu Ser Cys Ala Ala Ser Gly Phe
        35                  40                  45

Thr Val Ser Ser Asn Tyr Met Ser Trp Val Arg Gln Ala Pro Gly Lys
    50                  55                  60

Gly Leu Glu Trp Val Ser Val Ile Tyr Ser Gly Gly Ser Thr Tyr Tyr
65                  70                  75                  80

Ala Asp Ser Val Lys Gly Arg Phe Thr Ile Ser Arg Asp Asn Ser Lys
```

```
                            85                  90                  95
Asn Thr Leu Tyr Leu Gln Met Ser Asn Leu Thr Ala Glu Asp Thr Ala
                100                 105                 110

Val Tyr Tyr Cys Ala Arg Ala Val Pro His Ser Pro Ser Ala Phe Asp
        115                 120                 125

Arg Trp Gly Gln Gly Thr Leu Val Thr Val Ser Ser Glu Pro Lys Ser
130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
                180                 185                 190

His Glu Asp Pro Glu Val Lys Phe Asn Trp Tyr Val Asp Gly Val Glu
                195                 200                 205

Val His Asn Ala Lys Thr Lys Pro Arg Glu Glu Gln Tyr Asn Ser Thr
        210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
                260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
                340                 345                 350

Met His Glu Ala Leu His Asn His Tyr Thr Gln Lys Ser Leu Ser Leu
        355                 360                 365

Ser Pro Gly Lys
        370

<210> SEQ ID NO 39
<211> LENGTH: 119
<212> TYPE: PRT
<213> ORGANISM: Homo Sapiens

<400> SEQUENCE: 39

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80
```

```
Gln Met Ser Asn Leu Thr Ala Glu Asp Thr Ala Val Tyr Tyr Cys Ala
                85                  90                  95

Arg Ala Val Pro His Ser Pro Ser Ala Phe Asp Arg Trp Gly Gln Gly
            100                 105                 110

Thr Leu Val Thr Val Ser Ser
        115

<210> SEQ ID NO 40
<211> LENGTH: 10
<212> TYPE: PRT
<213> ORGANISM: Homo Sapiens

<400> SEQUENCE: 40

Gly Phe Thr Val Ser Ser Asn Tyr Met Ser
1               5                   10

<210> SEQ ID NO 41
<211> LENGTH: 16
<212> TYPE: PRT
<213> ORGANISM: Homo Sapiens

<400> SEQUENCE: 41

Val Ile Tyr Ser Gly Gly Ser Thr Tyr Tyr Ala Asp Ser Val Lys Gly
1               5                   10                  15

<210> SEQ ID NO 42
<211> LENGTH: 11
<212> TYPE: PRT
<213> ORGANISM: Homo Sapiens

<400> SEQUENCE: 42

Ala Val Pro His Ser Pro Ser Ala Phe Asp Arg
1               5                   10

<210> SEQ ID NO 43
<211> LENGTH: 1116
<212> TYPE: DNA
<213> ORGANISM: Homo Sapiens

<400> SEQUENCE: 43
atggagaccg acaccctgct gctgtgggtg ctgctgctgt gggtgcccgg atccaccggc      60
tctgaggtgc agctggagga gactggagga gacttgatcc agccgggggg gtccctgaga     120
ctctcctgta cagcctctgg gtttaacgtc agtagaatct acatgagctg ggtccgccag     180
gctccaggga aggggctgga gtgggtctca gtgatttata gcggtggaag tatatattac     240
gcagattccg tgaggggccg atttaccatc tccagagaca gttccacgaa cacggtgtat     300
cttcaaatga cagcctgag agccgaggac tcggccgtgt attactgtgc gagagccgtc     360
ccacatgccc ctagtaattt tgataaatgg ggccaaggga caagggtcac cgtctcttca     420
gagcccaaat cttgtgacaa aactcacaca tgcccaccgt gcccagcacc tgaactcctg     480
gggggaccgt cagtcttcct cttccccca aaacccaagg acaccctcat gatctcccgg     540
acccctgagg tcacatgcgt ggtggtggac gtgagccacg aagaccctga ggtcaagttc     600
aactggtacg tggacggcgt ggaggtgcat aatgccaaga caaagccgcg ggaggagcag     660
tacaacagca cgtaccgggt ggtcagcgtc ctcaccgtcc tgcaccagga ctggctgaat     720
ggcaaggagt acaagtgcaa ggtctccaac aaagccctcc cagcccccat cgagaaaacc     780
atctccaaag ccaaagggca gccccgagaa ccacaggtgt acaccctgcc cccatcccgg     840
gaggagatga ccaagaacca ggtcagcctg acctgcctgg tcaaaggctt ctatcccagc     900
```

```
gacatcgccg tggagtggga gagcaatggg cagccggaga acaactacaa gaccacgcct    960
cccgtgctgg actccgacgg ctccttcttc ctctacagca agctcaccgt ggacaagagc   1020
aggtggcagc aggggaacgt cttctcatgc tccgtgatgc atgaggctct gcacaaccac   1080
tacacgcaga gagcctctc cctgtctccg ggtaaa                              1116
```

<210> SEQ ID NO 44
<211> LENGTH: 372
<212> TYPE: PRT
<213> ORGANISM: Homo Sapiens

<400> SEQUENCE: 44

```
Met Glu Thr Asp Thr Leu Leu Leu Trp Val Leu Leu Leu Trp Val Pro
1               5                   10                  15

Gly Ser Thr Gly Ser Glu Val Gln Leu Glu Thr Gly Gly Asp Leu
                20                  25                  30

Ile Gln Pro Gly Gly Ser Leu Arg Leu Ser Cys Thr Ala Ser Gly Phe
                35                  40                  45

Asn Val Ser Arg Ile Tyr Met Ser Trp Val Arg Gln Ala Pro Gly Lys
            50                  55                  60

Gly Leu Glu Trp Val Ser Val Ile Tyr Ser Gly Gly Ser Ile Tyr Tyr
65              70                  75                  80

Ala Asp Ser Val Arg Gly Arg Phe Thr Ile Ser Arg Asp Ser Ser Thr
                85                  90                  95

Asn Thr Val Tyr Leu Gln Met Asn Ser Leu Arg Ala Glu Asp Ser Ala
            100                 105                 110

Val Tyr Tyr Cys Ala Arg Ala Val Pro His Ala Pro Ser Asn Phe Asp
        115                 120                 125

Lys Trp Gly Gln Gly Thr Arg Val Thr Val Ser Ser Glu Pro Lys Ser
130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335
```

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
        370

<210> SEQ ID NO 45
<211> LENGTH: 119
<212> TYPE: PRT
<213> ORGANISM: Homo Sapiens

<400> SEQUENCE: 45

Glu Val Gln Leu Glu Glu Thr Gly Gly Asp Leu Ile Gln Pro Gly Gly
1               5                   10                  15

Ser Leu Arg Leu Ser Cys Thr Ala Ser Gly Phe Asn Val Ser Arg Ile
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Ile Tyr Tyr Ala Asp Ser Val Arg
    50                  55                  60

Gly Arg Phe Thr Ile Ser Arg Asp Ser Ser Thr Asn Thr Val Tyr Leu
65                  70                  75                  80

Gln Met Asn Ser Leu Arg Ala Glu Asp Ser Ala Val Tyr Tyr Cys Ala
                85                  90                  95

Arg Ala Val Pro His Ala Pro Ser Asn Phe Asp Lys Trp Gly Gln Gly
            100                 105                 110

Thr Arg Val Thr Val Ser Ser
        115

<210> SEQ ID NO 46
<211> LENGTH: 10
<212> TYPE: PRT
<213> ORGANISM: Homo Sapiens

<400> SEQUENCE: 46

Gly Phe Asn Val Ser Arg Ile Tyr Met Ser
1               5                   10

<210> SEQ ID NO 47
<211> LENGTH: 16
<212> TYPE: PRT
<213> ORGANISM: Homo Sapiens

<400> SEQUENCE: 47

Val Ile Tyr Ser Gly Gly Ser Ile Tyr Tyr Ala Asp Ser Val Arg Gly
1               5                   10                  15

<210> SEQ ID NO 48
<211> LENGTH: 11
<212> TYPE: PRT
<213> ORGANISM: Homo Sapiens

<400> SEQUENCE: 48

Ala Val Pro His Ala Pro Ser Asn Phe Asp Lys
1               5                   10

<210> SEQ ID NO 49
<211> LENGTH: 1125
<212> TYPE: DNA

<213> ORGANISM: Homo Sapiens

<400> SEQUENCE: 49

```
atggagaccg acaccctgct gctgtgggtg ctgctgctgt gggtgcccgg atccaccggc      60
tctgaggtgc agctggtgga gtctggggga ggcttggttc agccgggggg gtccctgcga     120
ctctcctgtg tagcctctgg attcaccttc agtaactatt ggatgcactg ggtccgccaa     180
attccaggga aggggatggt gtggatctca gaaattaaca gtgacgggaa taggacaggc     240
tatgcggact ccgtaaaggg ccgattcacc atctccagag acaacgccaa gaagatgttg     300
tatctgcaaa tgaacagtct gagagccgag gacacggctg tttattattg tgcaagaaac     360
tggggatcgg gccccatca taccgctttt gatggttggg gccaagggac aatggtcacc      420
gtctcttcag agcccaaatc ttgtgacaaa actcacacat gcccaccgtg cccagcacct     480
gaactcctgg ggggaccgtc agtcttcctc ttccccccaa aacccaagga caccctcatg     540
atctcccgga cccctgaggt cacatgcgtg gtggtggacg tgagccacga agaccctgag     600
gtcaagttca actggtacgt ggacggcgtg gaggtgcata atgccaagac aaagccgcgg     660
gaggagcagt acaacagcac gtaccgggtg gtcagcgtcc tcaccgtcct gcaccaggac     720
tggctgaatg gcaaggagta caagtgcaag gtctccaaca aagccctccc agcccccatc     780
gagaaaacca tctccaaagc caaagggcag ccccgagaac acaggtgta caccctgccc      840
ccatcccggg aggagatgac caagaaccag gtcagcctga cctgcctggt caaaggcttc     900
tatcccagcg acatcgccgt ggagtgggag agcaatgggc agccggagaa caactacaag     960
accacgcctc ccgtgctgga ctccgacggc tccttcttcc tctacagcaa gctcaccgtg    1020
gacaagagca ggtggcagca ggggaacgtc ttctcatgct ccgtgatgca tgaggctctg    1080
cacaaccact acacgcagaa gagcctctcc ctgtctccgg gtaaa                    1125
```

<210> SEQ ID NO 50
<211> LENGTH: 375
<212> TYPE: PRT
<213> ORGANISM: Homo Sapiens

<400> SEQUENCE: 50

```
Met Glu Thr Asp Thr Leu Leu Leu Trp Val Leu Leu Leu Trp Val Pro
1               5                   10                  15

Gly Ser Thr Gly Ser Glu Val Gln Leu Val Glu Ser Gly Gly Gly Leu
            20                  25                  30

Val Gln Pro Gly Gly Ser Leu Arg Leu Ser Cys Val Ala Ser Gly Phe
        35                  40                  45

Thr Phe Ser Asn Tyr Trp Met His Trp Val Arg Gln Ile Pro Gly Lys
    50                  55                  60

Gly Met Val Trp Ile Ser Glu Ile Asn Ser Asp Gly Asn Arg Thr Gly
65                  70                  75                  80

Tyr Ala Asp Ser Val Lys Gly Arg Phe Thr Ile Ser Arg Asp Asn Ala
                85                  90                  95

Lys Lys Met Leu Tyr Leu Gln Met Asn Ser Leu Arg Ala Glu Asp Thr
            100                 105                 110

Ala Val Tyr Tyr Cys Ala Arg Asn Trp Gly Ser Gly Pro His His Thr
        115                 120                 125

Ala Phe Asp Gly Trp Gly Gln Gly Thr Met Val Thr Val Ser Ser Glu
    130                 135                 140

Pro Lys Ser Cys Asp Lys Thr His Thr Cys Pro Pro Cys Pro Ala Pro
145                 150                 155                 160
```

```
Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Lys Phe Asn Trp Tyr Val Asp
        195                 200                 205

Gly Val Glu Val His Asn Ala Lys Thr Lys Pro Arg Glu Glu Gln Tyr
    210                 215                 220

Asn Ser Thr Tyr Arg Val Val Ser Val Leu Thr Val Leu His Gln Asp
225                 230                 235                 240

Trp Leu Asn Gly Lys Glu Tyr Lys Cys Lys Val Ser Asn Lys Ala Leu
                245                 250                 255

Pro Ala Pro Ile Glu Lys Thr Ile Ser Lys Ala Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Val Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375

<210> SEQ ID NO 51
<211> LENGTH: 122
<212> TYPE: PRT
<213> ORGANISM: Homo Sapiens

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Trp Met His Trp Val Arg Gln Ile Pro Gly Lys Gly Met Val Trp Ile
        35                  40                  45

Ser Glu Ile Asn Ser Asp Gly Asn Arg Thr Gly Tyr Ala Asp Ser Val
    50                  55                  60

Lys Gly Arg Phe Thr Ile Ser Arg Asp Asn Ala Lys Lys Met Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Gly Ser Gly Pro His His Thr Ala Phe Asp Gly Trp
            100                 105                 110

Gly Gln Gly Thr Met Val Thr Val Ser Ser
        115                 120

<210> SEQ ID NO 52
<211> LENGTH: 10
<212> TYPE: PRT
```

<213> ORGANISM: Homo Sapiens

<400> SEQUENCE: 52

Gly Phe Thr Phe Ser Asn Tyr Trp Met His
1               5                   10

<210> SEQ ID NO 53
<211> LENGTH: 17
<212> TYPE: PRT
<213> ORGANISM: Homo Sapiens

<400> SEQUENCE: 53

Glu Ile Asn Ser Asp Gly Asn Arg Thr Gly Tyr Ala Asp Ser Val Lys
1               5                   10                  15

Gly

<210> SEQ ID NO 54
<211> LENGTH: 13
<212> TYPE: PRT
<213> ORGANISM: Homo Sapiens

<400> SEQUENCE: 54

Asn Trp Gly Ser Gly Pro His His Thr Ala Phe Asp Gly
1               5                   10

<210> SEQ ID NO 55
<211> LENGTH: 1116
<212> TYPE: DNA
<213> ORGANISM: Homo Sapiens

<400> SEQUENCE: 55

| | | | | | |
|---|---|---|---|---|---|
| atggagaccg | acaccctgct | gctgtgggtg | ctgctgctgt | gggtgcccgg | atccaccggc | 60 |
| tctgaggtgc | agctggagga | gactggagga | gacttgatcc | agccgggggg | gtccctgaga | 120 |
| ctctcctgta | cagcctctgg | gtttaccgtc | agtagaatct | acatgagctg | ggtccgccag | 180 |
| gctccaggga | aggggctgga | gtgggtctca | gtgatttata | gcggtggaag | tatatattac | 240 |
| gcagattccg | tgaggggccg | atttaccatc | tccagagaca | gttccacgaa | cacggtgttt | 300 |
| cttcaaatga | acagcctgag | agccgaggac | tcggccgtgt | attactgtgc | gagagccgtc | 360 |
| ccaagtgccc | ctagttcttt | tgatatctgg | ggccaaggga | caatggtcac | cgtctcttca | 420 |
| gagcccaaat | cttgtgacaa | aactcacaca | tgcccaccgt | gcccagcacc | tgaactcctg | 480 |
| gggggaccgt | cagtcttcct | cttcccccca | aaacccaagg | acaccctcat | gatctcccgg | 540 |
| acccctgagg | tcacatgcgt | ggtggtggac | gtgagccacg | aagaccctga | ggtcaagttc | 600 |
| aactggtacg | tggacggcgt | ggaggtgcat | aatgccaaga | caaagccgcg | ggaggagcag | 660 |
| tacaacagca | cgtaccgggt | ggtcagcgtc | ctcaccgtcc | tgcaccagga | ctggctgaat | 720 |
| ggcaaggagt | acaagtgcaa | ggtctccaac | aaagccctcc | cagcccccat | cgagaaaacc | 780 |
| atctccaaag | ccaaagggca | gccccgagaa | ccacaggtgt | acaccctgcc | ccatcccgg | 840 |
| gaggagatga | ccaagaacca | ggtcagcctg | acctgcctgg | tcaaaggctt | ctatcccagc | 900 |
| gacatcgccg | tggagtggga | gagcaatggg | cagccggaga | caactacaa | gaccacgcct | 960 |
| cccgtgctgg | actccgacgg | ctccttcttc | ctctacagca | agctcaccgt | ggacaagagc | 1020 |
| aggtggcagc | aggggaacgt | cttctcatgc | tccgtgatgc | atgaggctct | gcacaaccac | 1080 |
| tacacgcaga | agagcctctc | cctgtctccg | ggtaaa | | | 1116 |

<210> SEQ ID NO 56

```
<211> LENGTH: 372
<212> TYPE: PRT
<213> ORGANISM: Homo Sapiens

<400> SEQUENCE: 56

Met Glu Thr Asp Thr Leu Leu Leu Trp Val Leu Leu Trp Val Pro
1               5                   10                  15

Gly Ser Thr Gly Ser Glu Val Gln Leu Glu Thr Gly Gly Asp Leu
            20                  25                  30

Ile Gln Pro Gly Gly Ser Leu Arg Leu Ser Cys Thr Ala Ser Gly Phe
        35                  40                  45

Thr Val Ser Arg Ile Tyr Met Ser Trp Val Arg Gln Ala Pro Gly Lys
    50                  55                  60

Gly Leu Glu Trp Val Ser Val Ile Tyr Ser Gly Gly Ser Ile Tyr Tyr
65                  70                  75                  80

Ala Asp Ser Val Arg Gly Arg Phe Thr Ile Ser Arg Asp Ser Ser Thr
                85                  90                  95

Asn Thr Val Phe Leu Gln Met Asn Ser Leu Arg Ala Glu Asp Ser Ala
            100                 105                 110

Val Tyr Tyr Cys Ala Arg Ala Val Pro Ser Ala Pro Ser Ser Phe Asp
        115                 120                 125

Ile Trp Gly Gln Gly Thr Met Val Thr Val Ser Ser Glu Pro Lys Ser
130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370
```

<210> SEQ ID NO 57
<211> LENGTH: 119
<212> TYPE: PRT
<213> ORGANISM: Homo Sapiens

<400> SEQUENCE: 57

Glu Val Gln Leu Glu Glu Thr Gly Gly Asp Leu Ile Gln Pro Gly Gly
1               5                   10                  15

Ser Leu Arg Leu Ser Cys Thr Ala Ser Gly Phe Thr Val Ser Arg Ile
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Ile Tyr Tyr Ala Asp Ser Val Arg
    50                  55                  60

Gly Arg Phe Thr Ile Ser Arg Asp Ser Ser Thr Asn Thr Val Phe Leu
65                  70                  75                  80

Gln Met Asn Ser Leu Arg Ala Glu Asp Ser Ala Val Tyr Tyr Cys Ala
                85                  90                  95

Arg Ala Val Pro Ser Ala Pro Ser Ser Phe Asp Ile Trp Gly Gln Gly
            100                 105                 110

Thr Met Val Thr Val Ser Ser
        115

<210> SEQ ID NO 58
<211> LENGTH: 10
<212> TYPE: PRT
<213> ORGANISM: Homo Sapiens

<400> SEQUENCE: 58

Gly Phe Thr Val Ser Arg Ile Tyr Met Ser
1               5                   10

<210> SEQ ID NO 59
<211> LENGTH: 16
<212> TYPE: PRT
<213> ORGANISM: Homo Sapiens

<400> SEQUENCE: 59

Val Ile Tyr Ser Gly Gly Ser Ile Tyr Tyr Ala Asp Ser Val Arg Gly
1               5                   10                  15

<210> SEQ ID NO 60
<211> LENGTH: 11
<212> TYPE: PRT
<213> ORGANISM: Homo Sapiens

<400> SEQUENCE: 60

Ala Val Pro Ser Ala Pro Ser Ser Phe Asp Ile
1               5                   10

<210> SEQ ID NO 61
<211> LENGTH: 1116
<212> TYPE: DNA
<213> ORGANISM: Homo Sapiens

<400> SEQUENCE: 61
atggagaccg acaccctgct gctgtgggtg ctgctgctgt gggtgcccgg atccaccggc      60
tctgaggtgc agctggtgga gagcggagga ggcttgatcc agccgggggg gtccctgaga     120
ctctcctgtg ccgcctctgg gtttaccgtc agtagaatct acatgagctg ggtccgccag     180
gctccaggga aggggctgga gtgggtctca gtgatttata gcggtggaag tatatattac     240

```
gcagattccg tgaagggccg atttaccatc tccagagaca gttccaagaa cacggtgtac      300
cttcaaatga acagcctgag agccgaggac accgccgtgt attactgtgc gagagccgtc      360
ccaagtgccc ctagttcttt tgatatctgg ggccaaggga caatggtcac cgtctcttca      420
gagcccaaat cttgtgacaa aactcacaca tgcccaccgt gcccagcacc tgaactcctg      480 ggggggaccgt cagtcttcct cttcccccca aaacccaagg acaccctcat gatctcccgg      540
acccctgagg tcacatgcgt ggtggtggac gtgagccacg aagaccctga ggtcaagttc      600
aactggtacg tggacggcgt ggaggtgcat aatgccaaga caaagccgcg ggaggagcag      660
tacaacagca cgtaccgggt ggtcagcgtc ctcaccgtcc tgcaccagga ctggctgaat      720
ggcaaggagt acaagtgcaa ggtctccaac aaagccctcc cagcccccat cgagaaaacc      780
atctccaaag ccaaagggca gccccgagaa ccacaggtgt acaccctgcc cccatcccgg      840
gaggagatga ccaagaacca ggtcagcctg acctgcctgg tcaaaggctt ctatcccagc      900
gacatcgccg tggagtggga gagcaatggg cagccggaga caactacaa gaccacgcct       960 cccgtgctgg actccgacgg ctccttcttc ctctacagca agctcaccgt ggacaagagc     1020
aggtggcagc aggggaacgt cttctcatgc tccgtgatgc atgaggctct gcacaaccac     1080
tacacgcaga agagcctctc cctgtctccg ggtaaa                               1116
```

<210> SEQ ID NO 62
<211> LENGTH: 372
<212> TYPE: PRT
<213> ORGANISM: Homo Sapiens

<400> SEQUENCE: 62

```
Met Glu Thr Asp Thr Leu Leu Leu Trp Val Leu Leu Leu Trp Val Pro
1               5                   10                  15

Gly Ser Thr Gly Ser Glu Val Gln Leu Val Glu Ser Gly Gly Gly Leu
            20                  25                  30

Ile Gln Pro Gly Gly Ser Leu Arg Leu Ser Cys Ala Ala Ser Gly Phe
        35                  40                  45

Thr Val Ser Arg Ile Tyr Met Ser Trp Val Arg Gln Ala Pro Gly Lys
    50                  55                  60

Gly Leu Glu Trp Val Ser Val Ile Tyr Ser Gly Gly Ser Ile Tyr Tyr
65                  70                  75                  80

Ala Asp Ser Val Lys Gly Arg Phe Thr Ile Ser Arg Asp Ser Ser Lys
                85                  90                  95

Asn Thr Val Tyr Leu Gln Met Asn Ser Leu Arg Ala Glu Asp Thr Ala
            100                 105                 110

Val Tyr Tyr Cys Ala Arg Ala Val Pro Ser Ala Pro Ser Ser Phe Asp
        115                 120                 125

Ile Trp Gly Gln Gly Thr Met Val Thr Val Ser Ser Glu Pro Lys Ser
    130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
```

```
            210                 215                 220
Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
                260                 265                 270

Val Tyr Thr Leu Pro Pro Ser Arg Glu Glu Met Thr Lys Asn Gln Val
            275                 280                 285

Ser Leu Thr Cys Leu Val Lys Gly Phe Tyr Pro Ser Asp Ile Ala Val
            290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
                340                 345                 350

Met His Glu Ala Leu His Asn His Tyr Thr Gln Lys Ser Leu Ser Leu
            355                 360                 365

Ser Pro Gly Lys
    370

<210> SEQ ID NO 63
<211> LENGTH: 119
<212> TYPE: PRT
<213> ORGANISM: Homo Sapiens

<400> SEQUENCE: 63

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Arg Ile
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Ile Tyr Tyr Ala Asp Ser Val Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ala Val Pro Ser Ala Pro Ser Ser Phe Asp Ile Trp Gly Gln Gly
                100                 105                 110

Thr Met Val Thr Val Ser Ser
        115

<210> SEQ ID NO 64
<211> LENGTH: 10
<212> TYPE: PRT
<213> ORGANISM: Homo Sapiens

<400> SEQUENCE: 64

Gly Phe Thr Val Ser Arg Ile Tyr Met Ser
1               5                   10

<210> SEQ ID NO 65
<211> LENGTH: 16
<212> TYPE: PRT
```

<213> ORGANISM: Homo Sapiens

<400> SEQUENCE: 65

Val Ile Tyr Ser Gly Gly Ser Ile Tyr Tyr Ala Asp Ser Val Lys Gly
1               5                   10                  15

<210> SEQ ID NO 66
<211> LENGTH: 11
<212> TYPE: PRT
<213> ORGANISM: Homo Sapiens

<400> SEQUENCE: 66

Ala Val Pro Ser Ala Pro Ser Ser Phe Asp Ile
1               5                   10

<210> SEQ ID NO 67
<211> LENGTH: 1116
<212> TYPE: DNA
<213> ORGANISM: Homo Sapiens

<400> SEQUENCE: 67

```
atggagaccg acaccctgct gctgtgggtg ctgctgctgt gggtgcccgg atccaccggc      60
tctgaggtgc agctggtgga gactggagga gggctgatcc agccgggggg gtccctgaga     120
ctctcctgtg cagtctctgg gttcaccgtc agaaacaact acatgagctg ggcccgccag     180
gttccaggga agggactgga gtgggtctca gttatttata gcggtgggag tataacctac     240
gcagactccg tgaagggccg attcatcatc tccagagaca attccaagaa cacgctatat     300
cttcaaatga acggtctgag agccgaggac acggccgtat attactgtgc gagagccgtc     360
ccacatgccc aagtgctttt tgacatctgg ggccagggga caatggtcac cgtctcttca     420
gagcccaaat cttgtgacaa aactcacaca tgcccaccgt gcccagcacc tgaactcctg     480
gggggaccgt cagtcttcct cttccccccca aaacccaagg acaccctcat gatctcccgg     540
acccctgagg tcacatgcgt ggtggtggac gtgagccacg aagaccctga ggtcaagttc     600
aactggtacg tggacggcgt ggaggtgcat aatgccaaga caaagccgcg ggaggagcag     660
tacaacagca cgtaccgggt ggtcagcgtc ctcaccgtcc tgcaccagga ctggctgaat     720
ggcaaggagt acaagtgcaa ggtctccaac aaagccctcc cagcccccat cgagaaaacc     780
atctccaaag ccaaagggca gccccgagaa ccacaggtgt acaccctgcc cccatcccgg     840
gaggagatga ccaagaacca ggtcagcctg acctgcctgg tcaaaggctt ctatcccagc     900
gacatcgccg tggagtggga gagcaatggg cagccggaga acaactacaa gaccacgcct     960
cccgtgctgg actccgacgg ctccttcttc ctctacagca agctcaccgt ggacaagagc    1020
aggtggcagc aggggaacgt cttctcatgc tccgtgatgc atgaggctct gcacaaccac    1080
tacacgcaga agagcctctc cctgtctccg ggtaaa                              1116
```

<210> SEQ ID NO 68
<211> LENGTH: 372
<212> TYPE: PRT
<213> ORGANISM: Homo Sapiens

<400> SEQUENCE: 68

Met Glu Thr Asp Thr Leu Leu Leu Trp Val Leu Leu Leu Trp Val Pro
1               5                   10                  15

Gly Ser Thr Gly Ser Glu Val Gln Leu Val Glu Thr Gly Gly Gly Leu
            20                  25                  30

Ile Gln Pro Gly Gly Ser Leu Arg Leu Ser Cys Ala Val Ser Gly Phe

```
                35                  40                  45
Thr Val Arg Asn Asn Tyr Met Ser Trp Ala Arg Gln Val Pro Gly Lys
 50                  55                  60

Gly Leu Glu Trp Val Ser Val Ile Tyr Ser Gly Ser Ile Thr Tyr
 65                  70                  75                  80

Ala Asp Ser Val Lys Gly Arg Phe Ile Ile Ser Arg Asp Asn Ser Lys
                 85                  90                  95

Asn Thr Leu Tyr Leu Gln Met Asn Gly Leu Arg Ala Glu Asp Thr Ala
                100                 105                 110

Val Tyr Tyr Cys Ala Arg Ala Val Pro His Ala Pro Ser Ala Phe Asp
                115                 120                 125

Ile Trp Gly Gln Gly Thr Met Val Thr Val Ser Ser Glu Pro Lys Ser
130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
                180                 185                 190

His Glu Asp Pro Glu Val Lys Phe Asn Trp Tyr Val Asp Gly Val Glu
                195                 200                 205

Val His Asn Ala Lys Thr Lys Pro Arg Glu Glu Gln Tyr Asn Ser Thr
210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
                260                 265                 270

Val Tyr Thr Leu Pro Pro Ser Arg Glu Glu Met Thr Lys Asn Gln Val
                275                 280                 285

Ser Leu Thr Cys Leu Val Lys Gly Phe Tyr Pro Ser Asp Ile Ala Val
290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
                340                 345                 350

Met His Glu Ala Leu His Asn His Tyr Thr Gln Lys Ser Leu Ser Leu
                355                 360                 365

Ser Pro Gly Lys
   370

<210> SEQ ID NO 69
<211> LENGTH: 119
<212> TYPE: PRT
<213> ORGANISM: Homo Sapiens

<400> SEQUENCE: 69

Glu Val Gln Leu Val Glu Thr Gly Gly Gly Leu Ile Gln Pro Gly Gly
 1               5                  10                  15

Ser Leu Arg Leu Ser Cys Ala Val Ser Gly Phe Thr Val Arg Asn Asn
                20                  25                  30
```

```
Tyr Met Ser Trp Ala Arg Gln Val Pro Gly Lys Gly Leu Glu Trp Val
            35                  40                  45

Ser Val Ile Tyr Ser Gly Gly Ser Ile Thr Tyr Ala Asp Ser Val Lys
 50                  55                  60

Gly Arg Phe Ile Ile Ser Arg Asp Asn Ser Lys Asn Thr Leu Tyr Leu
 65                  70                  75                  80

Gln Met Asn Gly Leu Arg Ala Glu Asp Thr Ala Val Tyr Tyr Cys Ala
                 85                  90                  95

Arg Ala Val Pro His Ala Pro Ser Ala Phe Asp Ile Trp Gly Gln Gly
            100                 105                 110

Thr Met Val Thr Val Ser Ser
        115

<210> SEQ ID NO 70
<211> LENGTH: 10
<212> TYPE: PRT
<213> ORGANISM: Homo Sapiens

<400> SEQUENCE: 70

Gly Phe Thr Val Arg Asn Asn Tyr Met Ser
1               5                   10

<210> SEQ ID NO 71
<211> LENGTH: 16
<212> TYPE: PRT
<213> ORGANISM: Homo Sapiens

<400> SEQUENCE: 71

Val Ile Tyr Ser Gly Gly Ser Ile Thr Tyr Ala Asp Ser Val Lys Gly
1               5                   10                  15

<210> SEQ ID NO 72
<211> LENGTH: 11
<212> TYPE: PRT
<213> ORGANISM: Homo Sapiens

<400> SEQUENCE: 72

Ala Val Pro His Ala Pro Ser Ala Phe Asp Ile
1               5                   10

<210> SEQ ID NO 73
<211> LENGTH: 1116
<212> TYPE: DNA
<213> ORGANISM: Homo Sapiens

<400> SEQUENCE: 73
atggagaccg acaccctgct gctgtgggtg ctgctgctgt gggtgcccgg atccaccggc      60
tctgaggtgc agctggtgga gagcggagga gggctgatcc agccgggggg gtccctgaga     120
ctctcctgtg cagcctctgg gttcaccgtc agaaacaact acatgagctg ggtgcgccag     180
gccccaggga agggactgga gtgggtctca gttatttata gcggtgggag tataacctac     240
gcagactccg tgaagggccg attcaccatc tccagagaca attccaagaa cacgctatat     300
cttcaaatga acagcctgag agccgaggac acggccgtat attactgtgc gagagccgtc     360
ccacatgccc caagtgcttt tgacatctgg ggccagggga caatggtcac cgtctcttca     420
gagcccaaat cttgtgacaa aactcacaca tgcccaccgt gcccagcacc tgaactcctg     480
gggggaccgt cagtcttcct cttccccccca aaacccaagg acaccctcat gatctcccgg     540
acccctgagg tcacatgcgt ggtggtggac gtgagccacg aagaccctga ggtcaagttc     600
```

-continued

```
aactggtacg tggacggcgt ggaggtgcat aatgccaaga caaagccgcg ggaggagcag    660
tacaacagca cgtaccgggt ggtcagcgtc ctcaccgtcc tgcaccagga ctggctgaat    720
ggcaaggagt acaagtgcaa ggtctccaac aaagccctcc cagcccccat cgagaaaacc    780
atctccaaag ccaaagggca gccccgagaa ccacaggtgt acaccctgcc cccatcccgg    840
gaggagatga ccaagaacca ggtcagcctg acctgcctgg tcaaaggctt ctatcccagc    900
gacatcgccg tggagtggga gagcaatggg cagccggaga acaactacaa gaccacgcct    960
cccgtgctgg actccgacgg ctccttcttc ctctacagca agctcaccgt ggacaagagc   1020
aggtggcagc aggggaacgt cttctcatgc tccgtgatgc atgaggctct gcacaaccac   1080
tacacgcaga agagcctctc cctgtctccg ggtaaa                             1116
```

<210> SEQ ID NO 74
<211> LENGTH: 372
<212> TYPE: PRT
<213> ORGANISM: Homo Sapiens

<400> SEQUENCE: 74

```
Met Glu Thr Asp Thr Leu Leu Leu Trp Val Leu Leu Leu Trp Val Pro
1               5                   10                  15

Gly Ser Thr Gly Ser Glu Val Gln Leu Val Glu Ser Gly Gly Gly Leu
            20                  25                  30

Ile Gln Pro Gly Gly Ser Leu Arg Leu Ser Cys Ala Ala Ser Gly Phe
        35                  40                  45

Thr Val Arg Asn Asn Tyr Met Ser Trp Val Arg Gln Ala Pro Gly Lys
    50                  55                  60

Gly Leu Glu Trp Val Ser Val Ile Tyr Ser Gly Ser Ile Thr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Ala Val Pro His Ala Pro Ser Ala Phe Asp
        115                 120                 125

Ile Trp Gly Gln Gly Thr Met Val Thr Val Ser Ser Glu Pro Lys Ser
    130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285
```

```
Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 75
<211> LENGTH: 119
<212> TYPE: PRT
<213> ORGANISM: Homo Sapiens

<400> SEQUENCE: 75

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Arg Asn Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Ile Thr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Val Pro His Ala Pro Ser Ala Phe Asp Ile Trp Gly Gln Gly
            100                 105                 110

Thr Met Val Thr Val Ser Ser
        115

<210> SEQ ID NO 76
<211> LENGTH: 10
<212> TYPE: PRT
<213> ORGANISM: Homo Sapiens

<400> SEQUENCE: 76

Gly Phe Thr Val Arg Asn Asn Tyr Met Ser
1               5                   10

<210> SEQ ID NO 77
<211> LENGTH: 16
<212> TYPE: PRT
<213> ORGANISM: Homo Sapiens

<400> SEQUENCE: 77

Val Ile Tyr Ser Gly Gly Ser Ile Thr Tyr Ala Asp Ser Val Lys Gly
1               5                   10                  15

<210> SEQ ID NO 78
<211> LENGTH: 11
<212> TYPE: PRT
<213> ORGANISM: Homo Sapiens
```

<400> SEQUENCE: 78

Ala Val Pro His Ala Pro Ser Ala Phe Asp Ile
1               5                   10

<210> SEQ ID NO 79
<211> LENGTH: 1116
<212> TYPE: DNA
<213> ORGANISM: Homo Sapiens

<400> SEQUENCE: 79

```
atggagaccg acaccctgct gctgtgggtg ctgctgctgt gggtgcccgg atccaccggc      60
tctgaggtgc agctggtgga gactggagga ggcttgatcc agcctggggg gtccctgaga     120
ctctcctgtg cagcctctgg gttcaccgtc agtagcaact acatgagctg gtccgccag     180
gctccaggga aggggctgga gtgggtctca gttatttata gcggtggtag cacatactac     240
gcagactccg tgaagggccg attcaccatc tccagagaca attccaagaa cacgctgtat     300
cttcaaatga gcagcctgag ggccgaggac acggccgtgt attactgtgc gagagccgtt     360
ccccactccc ccagtgcttt tgataggtgg ggccagggaa ccctggtcac cgtctcttca     420
gagcccaaat cttgtgacaa aactcacaca tgcccaccgt gcccagcacc tgaactcctg     480
gggggaccgt cagtcttcct cttccccсcca aacccaagg acaccctcat gatctcccgg     540
acccctgagg tcacatgcgt ggtggtggac gtgagccacg aagaccctga ggtcaagttc     600
aactggtacg tggacggcgt ggaggtgcat aatgccaaga caaagccgcg ggaggagcag     660
tacaacagca cgtaccgggt ggtcagcgtc ctcaccgtcc tgcaccagga ctggctgaat     720
ggcaaggagt acaagtgcaa ggtctccaac aaagccctcc cagcccccat cgagaaaacc     780
atctccaaag ccaaagggca gccccgagaa ccacaggtgt acaccctgcc cccatcccgg     840
gaggagatga ccaagaacca ggtcagcctg acctgcctgg tcaaaggctt ctatcccagc     900
gacatcgccg tggagtggga gagcaatggg cagccggaga acaactacaa gaccacgcct     960
cccgtgctgg actccgacgg ctccttcttc ctctacagca agctcaccgt ggacaagagc    1020
aggtggcagc aggggaacgt cttctcatgc tccgtgatgc atgaggctct gcacaaccac    1080
tacacgcaga agagcctctc cctgtctccg ggtaaa                              1116
```

<210> SEQ ID NO 80
<211> LENGTH: 372
<212> TYPE: PRT
<213> ORGANISM: Homo Sapiens

<400> SEQUENCE: 80

Met Glu Thr Asp Thr Leu Leu Leu Trp Val Leu Leu Leu Trp Val Pro
1               5                   10                  15

Gly Ser Thr Gly Ser Glu Val Gln Leu Val Glu Thr Gly Gly Gly Leu
                20                  25                  30

Ile Gln Pro Gly Gly Ser Leu Arg Leu Ser Cys Ala Ala Ser Gly Phe
            35                  40                  45

Thr Val Ser Ser Asn Tyr Met Ser Trp Val Arg Gln Ala Pro Gly Lys
        50                  55                  60

Gly Leu Glu Trp Val Ser Val Ile Tyr Ser Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Ser Ser Leu Arg Ala Glu Asp Thr Ala
            100                 105                 110

```
Val Tyr Tyr Cys Ala Arg Ala Val Pro His Ser Pro Ser Ala Phe Asp
            115                 120                 125

Arg Trp Gly Gln Gly Thr Leu Val Thr Val Ser Ser Glu Pro Lys Ser
130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 81
<211> LENGTH: 119
<212> TYPE: PRT
<213> ORGANISM: Homo Sapiens

<400> SEQUENCE: 81

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Ala Val Pro His Ser Pro Ser Ala Phe Asp Arg Trp Gly Gln Gly
```

Thr Leu Val Thr Val Ser Ser
        115

<210> SEQ ID NO 82
<211> LENGTH: 10
<212> TYPE: PRT
<213> ORGANISM: Homo Sapiens

<400> SEQUENCE: 82

Gly Phe Thr Val Ser Ser Asn Tyr Met Ser
1               5                   10

<210> SEQ ID NO 83
<211> LENGTH: 16
<212> TYPE: PRT
<213> ORGANISM: Homo Sapiens

<400> SEQUENCE: 83

Val Ile Tyr Ser Gly Gly Ser Thr Tyr Tyr Ala Asp Ser Val Lys Gly
1               5                   10                  15

<210> SEQ ID NO 84
<211> LENGTH: 11
<212> TYPE: PRT
<213> ORGANISM: Homo Sapiens

<400> SEQUENCE: 84

Ala Val Pro His Ser Pro Ser Ala Phe Asp Arg
1               5                   10

<210> SEQ ID NO 85
<211> LENGTH: 1116
<212> TYPE: DNA
<213> ORGANISM: Homo Sapiens

<400> SEQUENCE: 85

```
atggagaccg acaccctgct gctgtgggtg ctgctgctgt gggtgcccgg atccaccggc      60
tctgaggtgc agctggtgga gagcggagga ggcttgatcc agcctggggg gtccctgaga     120
ctctcctgtg cagcctctgg gttcaccgtc agtagcaact acatgagctg ggtccgccag     180
gctccaggga aggggctgga gtgggtctca gttatttata gcggtggtag cacatactac     240
gcagactccg tgaagggccg attcaccatc tccagagaca attccaagaa cacgctgtat     300
cttcaaatga acagcctgag ggccgaggac acggccgtgt attactgtgc gagagccgtt     360
ccccactccc ccagtgcttt tgataggtgg ggccagggaa ccctggtcac cgtctcttca     420
gagcccaaat cttgtgacaa aactcacaca tgcccaccgt gcccagcacc tgaactcctg     480
gggggaccgt cagtcttcct cttcccccca aaacccaagg acaccctcat gatctcccgg     540
acccctgagg tcacatgcgt ggtggtggac gtgagccacg aagaccctga ggtcaagttc     600
aactggtacg tggacggcgt ggaggtgcat aatgccaaga caaagccgcg ggaggagcag     660
tacaacagca cgtaccgggt ggtcagcgtc ctcaccgtcc tgcaccagga ctggctgaat     720
ggcaaggagt acaagtgcaa ggtctccaac aaagccctcc cagcccccat cgagaaaacc     780
atctccaaag ccaaagggca gccccgagaa ccacaggtgt acaccctgcc cccatcccgg     840
gaggagatga ccaagaacca ggtcagcctg acctgcctgg tcaaaggctt ctatcccagc     900
gacatcgccg tggagtggga gagcaatggg cagccggaga caactacaa gaccacgcct     960
cccgtgctgg actccgacgg ctccttcttc ctctacagca agctcaccgt ggacaagagc    1020
```

-continued

```
aggtggcagc aggggaacgt cttctcatgc tccgtgatgc atgaggctct gcacaaccac    1080
tacacgcaga agagcctctc cctgtctccg ggtaaa                              1116
```

<210> SEQ ID NO 86
<211> LENGTH: 372
<212> TYPE: PRT
<213> ORGANISM: Homo Sapiens

<400> SEQUENCE: 86

| | | | | | | | | | | | | | | |
|---|---|---|---|---|---|---|---|---|---|---|---|---|---|---|
| Met | Glu | Thr | Asp | Thr | Leu | Leu | Leu | Trp | Val | Leu | Leu | Leu | Trp | Val | Pro |
| 1 | | | | 5 | | | | | 10 | | | | | 15 | |
| Gly | Ser | Thr | Gly | Ser | Glu | Val | Gln | Leu | Val | Glu | Ser | Gly | Gly | Gly | Leu |
| | | | 20 | | | | | 25 | | | | | 30 | | |
| Ile | Gln | Pro | Gly | Gly | Ser | Leu | Arg | Leu | Ser | Cys | Ala | Ala | Ser | Gly | Phe |
| | | | 35 | | | | 40 | | | | | 45 | | | |
| Thr | Val | Ser | Ser | Asn | Tyr | Met | Ser | Trp | Val | Arg | Gln | Ala | Pro | Gly | Lys |
| | | 50 | | | | | 55 | | | | 60 | | | | |
| Gly | Leu | Glu | Trp | Val | Ser | Val | Ile | Tyr | Ser | Gly | Gly | Ser | Thr | Tyr | Tyr |
| 65 | | | | 70 | | | | | 75 | | | | | 80 | |
| Ala | Asp | Ser | Val | Lys | Gly | Arg | Phe | Thr | Ile | Ser | Arg | Asp | Asn | Ser | Lys |
| | | | 85 | | | | | 90 | | | | | 95 | | |
| Asn | Thr | Leu | Tyr | Leu | Gln | Met | Asn | Ser | Leu | Arg | Ala | Glu | Asp | Thr | Ala |
| | | 100 | | | | | 105 | | | | | 110 | | | |
| Val | Tyr | Tyr | Cys | Ala | Arg | Ala | Val | Pro | His | Ser | Pro | Ser | Ala | Phe | Asp |
| | | 115 | | | | | 120 | | | | | 125 | | | |
| Arg | Trp | Gly | Gln | Gly | Thr | Leu | Val | Thr | Val | Ser | Ser | Glu | Pro | Lys | Ser |
| | 130 | | | | | 135 | | | | | 140 | | | | |
| Cys | Asp | Lys | Thr | His | Thr | Cys | Pro | Pro | Cys | Pro | Ala | Pro | Glu | Leu | Leu |
| 145 | | | | | 150 | | | | | 155 | | | | | 160 |
| Gly | Gly | Pro | Ser | Val | Phe | Leu | Phe | Pro | Pro | Lys | Pro | Lys | Asp | Thr | Leu |
| | | | | 165 | | | | | 170 | | | | | 175 | |
| Met | Ile | Ser | Arg | Thr | Pro | Glu | Val | Thr | Cys | Val | Val | Val | Asp | Val | Ser |
| | | | 180 | | | | | 185 | | | | | 190 | | |
| His | Glu | Asp | Pro | Glu | Val | Lys | Phe | Asn | Trp | Tyr | Val | Asp | Gly | Val | Glu |
| | | 195 | | | | | 200 | | | | | 205 | | | |
| Val | His | Asn | Ala | Lys | Thr | Lys | Pro | Arg | Glu | Glu | Gln | Tyr | Asn | Ser | Thr |
| 210 | | | | | 215 | | | | | 220 | | | | | |
| Tyr | Arg | Val | Val | Ser | Val | Leu | Thr | Val | Leu | His | Gln | Asp | Trp | Leu | Asn |
| 225 | | | | | 230 | | | | | 235 | | | | | 240 |
| Gly | Lys | Glu | Tyr | Lys | Cys | Lys | Val | Ser | Asn | Lys | Ala | Leu | Pro | Ala | Pro |
| | | | | 245 | | | | | 250 | | | | | 255 | |
| Ile | Glu | Lys | Thr | Ile | Ser | Lys | Ala | Lys | Gly | Gln | Pro | Arg | Glu | Pro | Gln |
| | | | 260 | | | | | 265 | | | | | 270 | | |
| Val | Tyr | Thr | Leu | Pro | Pro | Ser | Arg | Glu | Glu | Met | Thr | Lys | Asn | Gln | Val |
| | | 275 | | | | | 280 | | | | | 285 | | | |
| Ser | Leu | Thr | Cys | Leu | Val | Lys | Gly | Phe | Tyr | Pro | Ser | Asp | Ile | Ala | Val |
| | 290 | | | | | 295 | | | | | 300 | | | | |
| Glu | Trp | Glu | Ser | Asn | Gly | Gln | Pro | Glu | Asn | Asn | Tyr | Lys | Thr | Thr | Pro |
| 305 | | | | | 310 | | | | | 315 | | | | | 320 |
| Pro | Val | Leu | Asp | Ser | Asp | Gly | Ser | Phe | Phe | Leu | Tyr | Ser | Lys | Leu | Thr |
| | | | | 325 | | | | | 330 | | | | | 335 | |
| Val | Asp | Lys | Ser | Arg | Trp | Gln | Gln | Gly | Asn | Val | Phe | Ser | Cys | Ser | Val |
| | | | 340 | | | | | 345 | | | | | 350 | | |

-continued

Met His Glu Ala Leu His Asn His Tyr Thr Gln Lys Ser Leu Ser Leu
            355                 360                 365

Ser Pro Gly Lys
        370

<210> SEQ ID NO 87
<211> LENGTH: 119
<212> TYPE: PRT
<213> ORGANISM: Homo Sapiens

<400> SEQUENCE: 87

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Val Pro His Ser Pro Ser Ala Phe Asp Arg Trp Gly Gln Gly
            100                 105                 110

Thr Leu Val Thr Val Ser Ser
        115

<210> SEQ ID NO 88
<211> LENGTH: 10
<212> TYPE: PRT
<213> ORGANISM: Homo Sapiens

<400> SEQUENCE: 88

Gly Phe Thr Val Ser Ser Asn Tyr Met Ser
1               5                   10

<210> SEQ ID NO 89
<211> LENGTH: 16
<212> TYPE: PRT
<213> ORGANISM: Homo Sapiens

<400> SEQUENCE: 89

Val Ile Tyr Ser Gly Gly Ser Thr Tyr Tyr Ala Asp Ser Val Lys Gly
1               5                   10                  15

<210> SEQ ID NO 90
<211> LENGTH: 11
<212> TYPE: PRT
<213> ORGANISM: Homo Sapiens

<400> SEQUENCE: 90

Ala Val Pro His Ser Pro Ser Ala Phe Asp Arg
1               5                   10

<210> SEQ ID NO 91
<211> LENGTH: 1116
<212> TYPE: DNA
<213> ORGANISM: Homo Sapiens

<400> SEQUENCE: 91

```
atggagaccg acaccctgct gctgtgggtg ctgctgctgt gggtgcccgg atccaccggc        60
tctgaggtgc agctggagga gactggagga gacttgatcc agccgggggg gtccctgaga       120
ctctcctgta cagcctctgg gtttaccgtc agtagaatct acatgagctg ggtccgccag       180
gctccaggga aggggctgga gtgggtctca gtgatttata gcggtggaag tatatattac       240
gcagattccg tgaggggccg atttaccatc tccagagaca gttccacgaa cacggtgtat       300
cttcaaatga acagcctgag agccgaggac tcggccgtgt attactgtgc gagagccgtc       360
ccacatgccc ctagtaattt tgataaatgg ggccaaggga caagggtcac cgtctcttca       420
gagcccaaat cttgtgacaa aactcacaca tgcccaccgt gcccagcacc tgaactcctg       480
gggggaccgt cagtcttcct cttccccccc aaacccaagg acaccctcat gatctcccgg       540
accctgaggt gcacatgcgt ggtggtggac gtgagccacg aagaccctga ggtcaagttc       600
aactggtacg tggacggcgt ggaggtgcat aatgccaaga caaagccgcg ggaggagcag       660
tacaacagca cgtaccgggt ggtcagcgtc ctcaccgtcc tgcaccagga ctggctgaat       720
ggcaaggagt acaagtgcaa ggtctccaac aaagccctcc cagcccccat cgagaaaacc       780
atctccaaag ccaaagggca gccccgagaa ccacaggtgt acaccctgcc cccatcccgg       840
gaggagatga ccaagaacca ggtcagcctg acctgcctgg tcaaaggctt ctatcccagc       900
gacatcgccg tggagtggga gagcaatggg cagccggaga acaactacaa gaccacgcct       960
cccgtgctgg actccgacgg ctccttcttc ctctacagca agctcaccgt ggacaagagc      1020
aggtggcagc aggggaacgt cttctcatgc tccgtgatgc atgaggctct gcacaaccac      1080
tacacgcaga agagcctctc cctgtctccg ggtaaa                                1116
```

<210> SEQ ID NO 92
<211> LENGTH: 372
<212> TYPE: PRT
<213> ORGANISM: Homo Sapiens

<400> SEQUENCE: 92

```
Met Glu Thr Asp Thr Leu Leu Leu Trp Val Leu Leu Leu Trp Val Pro
1               5                   10                  15

Gly Ser Thr Gly Ser Glu Val Gln Leu Glu Glu Thr Gly Gly Asp Leu
            20                  25                  30

Ile Gln Pro Gly Gly Ser Leu Arg Leu Ser Cys Thr Ala Ser Gly Phe
        35                  40                  45

Thr Val Ser Arg Ile Tyr Met Ser Trp Val Arg Gln Ala Pro Gly Lys
    50                  55                  60

Gly Leu Glu Trp Val Ser Val Ile Tyr Ser Gly Gly Ser Ile Tyr Tyr
65                  70                  75                  80

Ala Asp Ser Val Arg Gly Arg Phe Thr Ile Ser Arg Asp Ser Ser Thr
                85                  90                  95

Asn Thr Val Tyr Leu Gln Met Asn Ser Leu Arg Ala Glu Asp Ser Ala
            100                 105                 110

Val Tyr Tyr Cys Ala Arg Ala Val Pro His Ala Pro Ser Asn Phe Asp
        115                 120                 125

Lys Trp Gly Gln Gly Thr Arg Val Thr Val Ser Ser Glu Pro Lys Ser
    130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175
```

```
Met Ile Ser Arg Thr Pro Glu Val Thr Cys Val Val Val Asp Val Ser
                180                 185                 190

His Glu Asp Pro Glu Val Lys Phe Asn Trp Tyr Val Asp Gly Val Glu
            195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
    275                 280                 285

Ser Leu Thr Cys Leu Val Lys Gly Phe Tyr Pro Ser Asp Ile Ala Val
290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
    355                 360                 365

Ser Pro Gly Lys
    370

<210> SEQ ID NO 93
<211> LENGTH: 119
<212> TYPE: PRT
<213> ORGANISM: Homo Sapiens

<400> SEQUENCE: 93

Glu Val Gln Leu Glu Glu Thr Gly Gly Asp Leu Ile Gln Pro Gly Gly
1               5                   10                  15

Ser Leu Arg Leu Ser Cys Thr Ala Ser Gly Phe Thr Val Ser Arg Ile
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Ile Tyr Tyr Ala Asp Ser Val Arg
    50                  55                  60

Gly Arg Phe Thr Ile Ser Arg Asp Ser Ser Asn Thr Val Tyr Leu
65                  70                  75                  80

Gln Met Asn Ser Leu Arg Ala Glu Asp Ser Ala Val Tyr Tyr Cys Ala
                85                  90                  95

Arg Ala Val Pro His Ala Pro Ser Asn Phe Asp Lys Trp Gly Gln Gly
            100                 105                 110

Thr Arg Val Thr Val Ser Ser
        115

<210> SEQ ID NO 94
<211> LENGTH: 10
<212> TYPE: PRT
<213> ORGANISM: Homo Sapiens

<400> SEQUENCE: 94
```

Gly Phe Thr Val Ser Arg Ile Tyr Met Ser
1               5                   10

<210> SEQ ID NO 95
<211> LENGTH: 16
<212> TYPE: PRT
<213> ORGANISM: Homo Sapiens

<400> SEQUENCE: 95

Val Ile Tyr Ser Gly Gly Ser Ile Tyr Tyr Ala Asp Ser Val Arg Gly
1               5                   10                  15

<210> SEQ ID NO 96
<211> LENGTH: 11
<212> TYPE: PRT
<213> ORGANISM: Homo Sapiens

<400> SEQUENCE: 96

Ala Val Pro His Ala Pro Ser Asn Phe Asp Lys
1               5                   10

<210> SEQ ID NO 97
<211> LENGTH: 1116
<212> TYPE: DNA
<213> ORGANISM: Homo Sapiens

<400> SEQUENCE: 97

| | |
|---|---:|
| atggagaccg acaccctgct gctgtgggtg ctgctgctgt gggtgcccgg atccaccggc | 60 |
| tctgaggtgc agctggcgga gactggagga ggcttgatcc agcctggggg gtccctgaga | 120 |
| ctctcctgtg cagtctctgg gttcaccgtc agtaagaatt acatgagctg ggtccgccag | 180 |
| gttccaggga aggggctgga gtgggtcgca gttgtttata gcggtggtag caaaacctac | 240 |
| gcagactccg tgaagggccg attcatcctc tccagagaca attccgacaa cacactgtat | 300 |
| cttcaaatga acaacctgag agccgaggac acggccgtgt attactgtgc gagagccgtt | 360 |
| cctcattccc ccagttcttt tgatatctgg ggccaaggga caatggtcac cgtctcttca | 420 |
| gagcccaaat cttgtgacaa aactcacaca tgcccaccgt gcccagcacc tgaactcctg | 480 |
| gggggaccgt cagtcttcct cttcccccca aaacccaagg acaccctcat gatctcccgg | 540 |
| accccctgagg tcacatgcgt ggtggtggac gtgagccacg aagaccctga ggtcaagttc | 600 |
| aactggtacg tggacggcgt ggaggtgcat aatgccaaga caaagccgcg ggaggagcag | 660 |
| tacaacagca cgtaccgggt ggtcagcgtc ctcaccgtcc tgcaccagga ctggctgaat | 720 |
| ggcaaggagt acaagtgcaa ggtctccaac aaagccctcc cagcccccat cgagaaaacc | 780 |
| atctccaaag ccaaagggca gccccgagaa ccacaggtgt acaccctgcc cccatcccgg | 840 |
| gaggagatga ccaagaacca ggtcagcctg acctgcctgg tcaaaggctt ctatcccagc | 900 |
| gacatcgccg tggagtggga gagcaatggg cagccggaga caactacaa gaccacgcct | 960 |
| cccgtgctgg actccgacgg ctccttcttc ctctacagca agctcaccgt ggacaagagc | 1020 |
| aggtggcagc aggggaacgt cttctcatgc tccgtgatgc atgaggctct gcacaaccac | 1080 |
| tacacgcaga agagcctctc cctgtctccg ggtaaa | 1116 |

<210> SEQ ID NO 98
<211> LENGTH: 372
<212> TYPE: PRT
<213> ORGANISM: Homo Sapiens

<400> SEQUENCE: 98

```
Met Glu Thr Asp Thr Leu Leu Leu Trp Val Leu Leu Leu Trp Val Pro
1               5                   10                  15

Gly Ser Thr Gly Ser Glu Val Gln Leu Val Glu Ser Gly Gly Gly Leu
            20                  25                  30

Ile Gln Pro Gly Gly Ser Leu Arg Leu Ser Cys Ala Ala Ser Gly Phe
            35                  40                  45

Thr Val Ser Arg Ile Tyr Met Ser Trp Val Arg Gln Ala Pro Gly Lys
50                  55                  60

Gly Leu Glu Trp Val Ser Val Ile Tyr Ser Gly Ser Ile Tyr Tyr
65                  70                  75                  80

Ala Asp Ser Val Lys Gly Arg Phe Thr Ile Ser Arg Asp Ser Ser Lys
            85                  90                  95

Asn Thr Val Tyr Leu Gln Met Asn Ser Leu Arg Ala Glu Asp Thr Ala
            100                 105                 110

Val Tyr Tyr Cys Ala Arg Ala Val Pro His Ala Pro Ser Asn Phe Asp
            115                 120                 125

Lys Trp Gly Gln Gly Thr Leu Val Thr Val Ser Glu Pro Lys Ser
            130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
            165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
            195                 200                 205

Val His Asn Ala Lys Thr Lys Pro Arg Glu Glu Gln Tyr Asn Ser Thr
210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
            245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
            275                 280                 285

Ser Leu Thr Cys Leu Val Lys Gly Phe Tyr Pro Ser Asp Ile Ala Val
            290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
            325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
            355                 360                 365

Ser Pro Gly Lys
    370

<210> SEQ ID NO 99
<211> LENGTH: 119
<212> TYPE: PRT
<213> ORGANISM: Homo Sapiens

<400> SEQUENCE: 99
```

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Arg Ile
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Ile Tyr Tyr Ala Asp Ser Val Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ala Val Pro His Ala Pro Ser Asn Phe Asp Lys Trp Gly Gln Gly
            100                 105                 110

Thr Leu Val Thr Val Ser Ser
        115
```

<210> SEQ ID NO 100
<211> LENGTH: 10
<212> TYPE: PRT
<213> ORGANISM: Homo Sapiens

<400> SEQUENCE: 100

```
Gly Phe Thr Val Ser Arg Ile Tyr Met Ser
1               5                   10
```

<210> SEQ ID NO 101
<211> LENGTH: 16
<212> TYPE: PRT
<213> ORGANISM: Homo Sapiens

<400> SEQUENCE: 101

```
Val Ile Tyr Ser Gly Gly Ser Ile Tyr Tyr Ala Asp Ser Val Lys Gly
1               5                   10                  15
```

<210> SEQ ID NO 102
<211> LENGTH: 11
<212> TYPE: PRT
<213> ORGANISM: Homo Sapiens

<400> SEQUENCE: 102

```
Ala Val Pro His Ala Pro Ser Asn Phe Asp Lys
1               5                   10
```

<210> SEQ ID NO 103
<211> LENGTH: 1116
<212> TYPE: DNA
<213> ORGANISM: Homo Sapiens

<400> SEQUENCE: 103

| | | | | | |
|---|---|---|---|---|---|
| atggagaccg | acaccctgct | gctgtgggtg | ctgctgctgt | gggtgcccgg | atccaccggc | 60 |
| tctgaggtgc | agctggcgga | gactggagga | ggcttgatcc | agcctggggg | gtccctgaga | 120 |
| ctctcctgtg | cagtctctgg | gttcaccgtc | agtaagaatt | acatgagctg | ggtccgccag | 180 |
| gttccaggga | aggggctgga | gtgggtcgca | gttgtttata | gcggtggtag | caaaacctac | 240 |
| gcagactccg | tgaagggccg | attcatcctc | tccagagaca | attccgacaa | cacactgtat | 300 |
| cttcaaatga | acaacctgag | agccgaggac | acggccgtgt | attactgtgc | gagagccgtt | 360 |
| cctcattccc | ccagttcttt | tgatatctgg | ggccaaggga | caatggtcac | cgtctcttca | 420 |

```
gagcccaaat cttgtgacaa aactcacaca tgcccaccgt gcccagcacc tgaactcctg      480
gggggaccgt cagtcttcct cttccccca aaacccaagg acaccctcat gatctcccgg       540 accctgagg tcacatgcgt ggtggtggac gtgagccacg aagaccctga ggtcaagttc       600
aactggtacg tggacggcgt ggaggtgcat aatgccaaga caaagccgcg ggaggagcag      660
tacaacagca cgtaccgggt ggtcagcgtc ctcaccgtcc tgcaccagga ctggctgaat      720
ggcaaggagt acaagtgcaa ggtctccaac aaagcctcc cagcccccat cgagaaaacc       780
atctccaaag ccaaagggca gccccgagaa ccacaggtgt acaccctgcc cccatcccgg      840
gaggagatga ccaagaacca ggtcagcctg acctgcctgg tcaaaggctt ctatcccagc      900
gacatcgccg tggagtggga gagcaatggg cagccggaga acaactacaa gaccacgcct      960
cccgtgctgg actccgacgg ctccttcttc ctctacagca agctcaccgt ggacaagagc     1020
aggtggcagc aggggaacgt cttctcatgc tccgtgatgc atgaggctct gcacaaccac     1080
tacacgcaga agagcctctc cctgtctccg ggtaaa                               1116
```

<210> SEQ ID NO 104
<211> LENGTH: 372
<212> TYPE: PRT
<213> ORGANISM: Homo Sapiens

<400> SEQUENCE: 104

```
Met Glu Thr Asp Thr Leu Leu Leu Trp Val Leu Leu Leu Trp Val Pro
1               5                   10                  15

Gly Ser Thr Gly Ser Glu Val Gln Leu Ala Glu Thr Gly Gly Gly Leu
            20                  25                  30

Ile Gln Pro Gly Gly Ser Leu Arg Leu Ser Cys Ala Val Ser Gly Phe
        35                  40                  45

Thr Val Ser Lys Asn Tyr Met Ser Trp Val Arg Gln Val Pro Gly Lys
    50                  55                  60

Gly Leu Glu Trp Val Ala Val Tyr Ser Gly Gly Ser Lys Thr Tyr
65                  70                  75                  80

Ala Asp Ser Val Lys Gly Arg Phe Ile Leu Ser Arg Asp Asn Ser Asp
                85                  90                  95

Asn Thr Leu Tyr Leu Gln Met Asn Asn Leu Arg Ala Glu Asp Thr Ala
            100                 105                 110

Val Tyr Tyr Cys Ala Arg Ala Val Pro His Ser Pro Ser Ser Phe Asp
        115                 120                 125

Ile Trp Gly Gln Gly Thr Met Val Thr Val Ser Glu Pro Lys Ser
    130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
```

```
                    245                 250                 255
Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
        370

<210> SEQ ID NO 105
<211> LENGTH: 119
<212> TYPE: PRT
<213> ORGANISM: Homo Sapiens

<400> SEQUENCE: 105

Glu Val Gln Leu Ala Glu Thr Gly Gly Gly Leu Ile Gln Pro Gly Gly
1               5                   10                  15

Ser Leu Arg Leu Ser Cys Ala Val Ser Gly Phe Thr Val Ser Lys Asn
            20                  25                  30

Tyr Met Ser Trp Val Arg Gln Val Pro Gly Lys Gly Leu Glu Trp Val
        35                  40                  45

Ala Val Val Tyr Ser Gly Gly Ser Lys Thr Tyr Ala Asp Ser Val Lys
    50                  55                  60

Gly Arg Phe Ile Leu Ser Arg Asp Asn Ser Asp Asn Thr Leu Tyr Leu
65                  70                  75                  80

Gln Met Asn Asn Leu Arg Ala Glu Asp Thr Ala Val Tyr Tyr Cys Ala
                85                  90                  95

Arg Ala Val Pro His Ser Pro Ser Ser Phe Asp Ile Trp Gly Gln Gly
            100                 105                 110

Thr Met Val Thr Val Ser Ser
        115

<210> SEQ ID NO 106
<211> LENGTH: 10
<212> TYPE: PRT
<213> ORGANISM: Homo Sapiens

<400> SEQUENCE: 106

Gly Phe Thr Val Ser Lys Asn Tyr Met Ser
1               5                   10

<210> SEQ ID NO 107
<211> LENGTH: 16
<212> TYPE: PRT
<213> ORGANISM: Homo Sapiens

<400> SEQUENCE: 107

Val Val Tyr Ser Gly Gly Ser Lys Thr Tyr Ala Asp Ser Val Lys Gly
1               5                   10                  15
```

<210> SEQ ID NO 108
<211> LENGTH: 11
<212> TYPE: PRT
<213> ORGANISM: Homo Sapiens

<400> SEQUENCE: 108

Ala Val Pro His Ser Pro Ser Ser Phe Asp Ile
1               5                   10

<210> SEQ ID NO 109
<211> LENGTH: 1116
<212> TYPE: DNA
<213> ORGANISM: Homo Sapiens

<400> SEQUENCE: 109

```
atggagaccg acaccctgct gctgtgggtg ctgctgctgt gggtgcccgg atccaccggc      60
tctgaggtgc agctggtgga gagcggagga ggcttgatcc agcctggggg gtccctgaga     120
ctctcctgtg cagtctctgg gttcaccgtc agtaagaatt acatgagctg ggtccgccag     180
gccccaggga aggggctgga gtgggtcagc gttgtttata gcggtggtag caaaacctac     240
gcagactccg tgaagggccg attcaccatc tccagagaca attccaagaa cactctgtat     300
cttcaaatga acagcctgag agccgaggac acggccgtgt attactgtgc gagagccgtt     360
cctcattccc ccagttcttt tgatatctgg ggccaaggga caatggtcac cgtctcttca     420
gagcccaaat cttgtgacaa aactcacaca tgcccaccgt gcccagcacc tgaactcctg     480
gggggaccgt cagtcttcct cttccccccca aaacccaagg acaccctcat gatctcccgg     540
acccctgagg tcacatgcgt ggtggtggac gtgagccacg aagaccctga ggtcaagttc     600
aactggtacg tggacggcgt ggaggtgcat aatgccaaga caaagccgcg ggaggagcag     660
tacaacagca cgtaccgggt ggtcagcgtc ctcaccgtcc tgcaccagga ctggctgaat     720
ggcaaggagt acaagtgcaa ggtctccaac aaagccctcc cagcccccat cgagaaaacc     780
atctccaaag ccaaagggca gccccgagaa ccacaggtgt acaccctgcc cccatcccgg     840
gaggagatga ccaagaacca ggtcagcctg acctgcctgg tcaaaggctt ctatcccagc     900
gacatcgccg tggagtggga gagcaatggg cagccggaga caactacaa gaccacgcct     960
cccgtgctgg actccgacgg ctccttcttc ctctacagca agctcaccgt ggacaagagc    1020
aggtggcagc aggggaacgt cttctcatgc tccgtgatgc atgaggctct gcacaaccac    1080
tacacgcaga agagcctctc cctgtctccg ggtaaa                               1116
```

<210> SEQ ID NO 110
<211> LENGTH: 372
<212> TYPE: PRT
<213> ORGANISM: Homo Sapiens

<400> SEQUENCE: 110

Met Glu Thr Asp Thr Leu Leu Leu Trp Val Leu Leu Leu Trp Val Pro
1               5                   10                  15

Gly Ser Thr Gly Ser Glu Val Gln Leu Val Glu Ser Gly Gly Gly Leu
            20                  25                  30

Ile Gln Pro Gly Gly Ser Leu Arg Leu Ser Cys Ala Val Ser Gly Phe
        35                  40                  45

Thr Val Ser Lys Asn Tyr Met Ser Trp Val Arg Gln Ala Pro Gly Lys
    50                  55                  60

Gly Leu Glu Trp Val Ser Val Val Tyr Ser Gly Gly Ser Lys Thr Tyr

```
                65                  70                  75                  80
Ala Asp Ser Val Lys Gly Arg Phe Thr Ile Ser Arg Asp Asn Ser Lys
                    85                  90                  95

Asn Thr Leu Tyr Leu Gln Met Asn Ser Leu Arg Ala Glu Asp Thr Ala
                100                 105                 110

Val Tyr Tyr Cys Ala Arg Ala Val Pro His Ser Pro Ser Ser Phe Asp
                115                 120                 125

Ile Trp Gly Gln Gly Thr Met Val Thr Val Ser Ser Glu Pro Lys Ser
            130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                    165                 170                 175

Met Ile Ser Arg Thr Pro Glu Val Thr Cys Val Val Val Asp Val Ser
                180                 185                 190

His Glu Asp Pro Glu Val Lys Phe Asn Trp Tyr Val Asp Gly Val Glu
                195                 200                 205

Val His Asn Ala Lys Thr Lys Pro Arg Glu Glu Gln Tyr Asn Ser Thr
            210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                    245                 250                 255

Ile Glu Lys Thr Ile Ser Lys Ala Lys Gly Gln Pro Arg Glu Pro Gln
                260                 265                 270

Val Tyr Thr Leu Pro Pro Ser Arg Glu Glu Met Thr Lys Asn Gln Val
                275                 280                 285

Ser Leu Thr Cys Leu Val Lys Gly Phe Tyr Pro Ser Asp Ile Ala Val
            290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                    325                 330                 335

Val Asp Lys Ser Arg Trp Gln Gln Gly Asn Val Phe Ser Cys Ser Val
                340                 345                 350

Met His Glu Ala Leu His Asn His Tyr Thr Gln Lys Ser Leu Ser Leu
                355                 360                 365

Ser Pro Gly Lys
            370

<210> SEQ ID NO 111
<211> LENGTH: 119
<212> TYPE: PRT
<213> ORGANISM: Homo Sapiens

<400> SEQUENCE: 111

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Thr Val Ser Lys Asn
                20                  25                  30

Tyr Met Ser Trp Val Arg Gln Ala Pro Gly Lys Gly Leu Glu Trp Val
            35                  40                  45

Ser Val Val Tyr Ser Gly Gly Ser Lys Thr Tyr Ala Asp Ser Val Lys
        50                  55                  60
```

```
Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ala Val Pro His Ser Pro Ser Ser Phe Asp Ile Trp Gly Gln Gly
            100                 105                 110

Thr Met Val Thr Val Ser Ser
            115

<210> SEQ ID NO 112
<211> LENGTH: 10
<212> TYPE: PRT
<213> ORGANISM: Homo Sapiens

<400> SEQUENCE: 112

Gly Phe Thr Val Ser Lys Asn Tyr Met Ser
1               5                   10

<210> SEQ ID NO 113
<211> LENGTH: 16
<212> TYPE: PRT
<213> ORGANISM: Homo Sapiens

<400> SEQUENCE: 113

Val Val Tyr Ser Gly Gly Ser Lys Thr Tyr Ala Asp Ser Val Lys Gly
1               5                   10                  15

<210> SEQ ID NO 114
<211> LENGTH: 11
<212> TYPE: PRT
<213> ORGANISM: Homo Sapiens

<400> SEQUENCE: 114

Ala Val Pro His Ser Pro Ser Ser Phe Asp Ile
1               5                   10

<210> SEQ ID NO 115
<211> LENGTH: 1116
<212> TYPE: DNA
<213> ORGANISM: Homo Sapiens

<400> SEQUENCE: 115
atggagaccg acaccctgct gctgtgggtg ctgctgctgt gggtgcccgg atccaccggc     60
tctgaggtgc agctggagga gactggagga gacttgatcc agccgggggg gtccctgaga    120
ctctcctgta cagcctctgg gtttaacgtc agtagaatct acatgagctg ggtccgccag    180
gctccaggga aggggctgga gtgggtctca gtgatttata gcggtggaag tatatattac    240
gcagattccg tgaggggccg atttaccatc tccagagaca gttccacgaa cacggtgttt    300
cttcaaatga acagcctgag agccgaggac tcggccgtgt attactgtgc gagagccgtc    360
ccaagtgccc ctagttcttt tgatatctgg ggccaaggga caatggtcac cgtctcttca    420
gagcccaaat cttgtgacaa aactcacaca tgcccaccgt gcccagcacc tgaactcctg    480
gggggaccgg acgtcttcct cttcccccca aaacccaagg acaccctcat gatctcccgg    540
acccctgagg tcacatgcgt ggtggtggac gtgagccacg aagaccctga ggtcaagttc    600
aactggtacg tggacggcgt ggaggtgcat aatgccaaga caaagccgcg ggaggagcag    660
tacaacagca cgtaccgggt ggtcagcgtc ctcaccgtcc tgcaccagga ctggctgaat    720
ggcaaggagt acaagtgcaa ggtctccaac aaagccctcc cagcccccga ggagaaaacc    780
```

```
atctccaaag ccaaagggca gccccgagaa ccacaggtgt acaccctgcc cccatcccgg    840
gaggagatga ccaagaacca ggtcagcctg acctgcctgg tcaaaggctt ctatcccagc    900
gacatcgccg tggagtggga gagcaatggg cagccggaga caactacaa gaccacgcct    960 cccgtgctgg actccgacgg ctccttcttc ctctacagca agctcaccgt ggacaagagc   1020
aggtggcagc aggggaacgt cttctcatgc tccgtgatgc atgaggctct gcacaaccac   1080
tacacgcaga gagcctctc cctgtctccg ggtaaa                              1116
```

<210> SEQ ID NO 116
<211> LENGTH: 372
<212> TYPE: PRT
<213> ORGANISM: Homo Sapiens

<400> SEQUENCE: 116

```
Met Glu Thr Asp Thr Leu Leu Leu Trp Val Leu Leu Leu Trp Val Pro
1               5                   10                  15

Gly Ser Thr Gly Ser Glu Val Gln Leu Glu Glu Thr Gly Gly Asp Leu
            20                  25                  30

Ile Gln Pro Gly Gly Ser Leu Arg Leu Ser Cys Thr Ala Ser Gly Phe
        35                  40                  45

Asn Val Ser Arg Ile Tyr Met Ser Trp Val Arg Gln Ala Pro Gly Lys
    50                  55                  60

Gly Leu Glu Trp Val Ser Val Ile Tyr Ser Gly Gly Ser Ile Tyr Tyr
65                  70                  75                  80

Ala Asp Ser Val Arg Gly Arg Phe Thr Ile Ser Arg Asp Ser Ser Thr
                85                  90                  95

Asn Thr Val Phe Leu Gln Met Asn Ser Leu Arg Ala Glu Asp Ser Ala
            100                 105                 110

Val Tyr Tyr Cys Ala Arg Ala Val Pro Ser Ala Pro Ser Ser Phe Asp
        115                 120                 125

Ile Trp Gly Gln Gly Thr Met Val Thr Val Ser Ser Glu Pro Lys Ser
    130                 135                 140

Cys Asp Lys Thr His Thr Cys Pro Pro Cys Pro Ala Pro Glu Leu Leu
145                 150                 155                 160

Gly Gly Pro Asp Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Glu Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320
```

```
Pro Val Leu Asp Ser Asp Gly Ser Phe Phe Leu Tyr Ser Lys Leu Thr
            325                 330                 335

Val Asp Lys Ser Arg Trp Gln Gln Gly Asn Val Phe Ser Cys Ser Val
        340                 345                 350

Met His Glu Ala Leu His Asn His Tyr Thr Gln Lys Ser Leu Ser Leu
        355                 360                 365

Ser Pro Gly Lys
        370

<210> SEQ ID NO 117
<211> LENGTH: 119
<212> TYPE: PRT
<213> ORGANISM: Homo Sapiens

<400> SEQUENCE: 117

Glu Val Gln Leu Glu Glu Thr Gly Gly Asp Leu Ile Gln Pro Gly Gly
1               5                   10                  15

Ser Leu Arg Leu Ser Cys Thr Ala Ser Gly Phe Asn Val Ser Arg Ile
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Ile Tyr Tyr Ala Asp Ser Val Arg
    50                  55                  60

Gly Arg Phe Thr Ile Ser Arg Asp Ser Ser Thr Asn Thr Val Phe Leu
65                  70                  75                  80

Gln Met Asn Ser Leu Arg Ala Glu Asp Ser Ala Val Tyr Tyr Cys Ala
                85                  90                  95

Arg Ala Val Pro Ser Ala Pro Ser Ser Phe Asp Ile Trp Gly Gln Gly
            100                 105                 110

Thr Met Val Thr Val Ser Ser
        115

<210> SEQ ID NO 118
<211> LENGTH: 10
<212> TYPE: PRT
<213> ORGANISM: Homo Sapiens

<400> SEQUENCE: 118

Gly Phe Asn Val Ser Arg Ile Tyr Met Ser
1               5                   10

<210> SEQ ID NO 119
<211> LENGTH: 16
<212> TYPE: PRT
<213> ORGANISM: Homo Sapiens

<400> SEQUENCE: 119

Val Ile Tyr Ser Gly Gly Ser Ile Tyr Tyr Ala Asp Ser Val Arg Gly
1               5                   10                  15

<210> SEQ ID NO 120
<211> LENGTH: 11
<212> TYPE: PRT
<213> ORGANISM: Homo Sapiens

<400> SEQUENCE: 120

Ala Val Pro Ser Ala Pro Ser Ser Phe Asp Ile
1               5                   10
```

<210> SEQ ID NO 121
<211> LENGTH: 1116
<212> TYPE: DNA
<213> ORGANISM: Homo Sapiens

<400> SEQUENCE: 121

```
atggagaccg acaccctgct gctgtgggtg ctgctgctgt gggtgcccgg atccaccggc    60
tctgaggtgc agctggtgga gactggagga gggctgatcc agccgggggg gtccctgaga   120
ctctcctgtg cagtctctgg gttcaccgtc agaaacaact acatgagctg ggcccgccag   180
gttccaggga agggactgga gtgggtctca gttatttata gcggtgggag tataacctac   240
gcagactccg tgaagggccg attcatcatc tccagagaca attccaacaa cacgctatat   300
cttcaaatga acggtctgag agccgaggac acggccgtat attactgtgc gagagccgtc   360
ccacatgccc caagtgcttt tgacatctgg ggccagggga caatggtcac cgtctcttca   420
gagcccaaat cttgtgacaa aactcacaca tgcccaccgt gcccagcacc tgaactcctg   480
gggggaccgg acgtcttcct cttcccccca aaacccaagg acaccctcat gatctcccgg   540
acccctgagg tcacatgcgt ggtggtggac gtgagccacg aagaccctga ggtcaagttc   600
aactggtacg tggacggcgt ggaggtgcat aatgccaaga caaagccgcg ggaggagcag   660
tacaacagca cgtaccgggt ggtcagcgtc ctcaccgtcc tgcaccagga ctggctgaat   720
ggcaaggagt acaagtgcaa ggtctccaac aaagccctcc cagcccccga ggagaaaacc   780
atctccaaag ccaaagggca gccccgagaa ccacaggtgt acaccctgcc cccatcccgg   840
gaggagatga ccaagaacca ggtcagcctg acctgcctgg tcaaaggctt ctatcccagc   900
gacatcgccg tggagtggga gagcaatggg cagccggaga caactacaa gaccacgcct   960
cccgtgctgg actccgacgg ctccttcttc ctctacagca agctcaccgt ggacaagagc  1020
aggtggcagc aggggaacgt cttctcatgc tccgtgatgc atgaggctct gcacaaccac  1080
tacacgcaga agagcctctc cctgtctccg ggtaaa                            1116
```

<210> SEQ ID NO 122
<211> LENGTH: 372
<212> TYPE: PRT
<213> ORGANISM: Homo Sapiens

<400> SEQUENCE: 122

```
Met Glu Thr Asp Thr Leu Leu Leu Trp Val Leu Leu Leu Trp Val Pro
1               5                   10                  15

Gly Ser Thr Gly Ser Glu Val Gln Leu Val Glu Thr Gly Gly Gly Leu
            20                  25                  30

Ile Gln Pro Gly Gly Ser Leu Arg Leu Ser Cys Ala Val Ser Gly Phe
        35                  40                  45

Thr Val Arg Asn Asn Tyr Met Ser Trp Ala Arg Gln Val Pro Gly Lys
    50                  55                  60

Gly Leu Glu Trp Val Ser Val Ile Tyr Ser Gly Gly Ser Ile Thr Tyr
65                  70                  75                  80

Ala Asp Ser Val Lys Gly Arg Phe Ile Ile Ser Arg Asp Asn Ser Asn
                85                  90                  95

Asn Thr Leu Tyr Leu Gln Met Asn Gly Leu Arg Ala Glu Asp Thr Ala
            100                 105                 110

Val Tyr Tyr Cys Ala Arg Ala Val Pro His Ala Pro Ser Ala Phe Asp
        115                 120                 125

Ile Trp Gly Gln Gly Thr Met Val Thr Val Ser Ser Glu Pro Lys Ser
    130                 135                 140
```

Cys Asp Lys Thr His Thr Cys Pro Pro Cys Pro Ala Pro Glu Leu Leu
145                 150                 155                 160

Gly Gly Pro Asp Val Phe Leu Phe Pro Pro Lys Pro Lys Asp Thr Leu
            165                 170                 175

Met Ile Ser Arg Thr Pro Glu Val Thr Cys Val Val Val Asp Val Ser
        180                 185                 190

His Glu Asp Pro Glu Val Lys Phe Asn Trp Tyr Val Asp Gly Val Glu
            195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
            245                 250                 255

Glu Glu Lys Thr Ile Ser Lys Ala Lys Gly Gln Pro Arg Glu Pro Gln
        260                 265                 270

Val Tyr Thr Leu Pro Pro Ser Arg Glu Glu Met Thr Lys Asn Gln Val
    275                 280                 285

Ser Leu Thr Cys Leu Val Lys Gly Phe Tyr Pro Ser Asp Ile Ala Val
290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
            325                 330                 335

Val Asp Lys Ser Arg Trp Gln Gln Gly Asn Val Phe Ser Cys Ser Val
        340                 345                 350

Met His Glu Ala Leu His Asn His Tyr Thr Gln Lys Ser Leu Ser Leu
    355                 360                 365

Ser Pro Gly Lys
    370

<210> SEQ ID NO 123
<211> LENGTH: 119
<212> TYPE: PRT
<213> ORGANISM: Homo Sapiens

<400> SEQUENCE: 123

Glu Val Gln Leu Val Glu Thr Gly Gly Gly Leu Ile Gln Pro Gly Gly
1               5                   10                  15

Ser Leu Arg Leu Ser Cys Ala Val Ser Gly Phe Thr Val Arg Asn Asn
            20                  25                  30

Tyr Met Ser Trp Ala Arg Gln Val Pro Gly Lys Gly Leu Glu Trp Val
        35                  40                  45

Ser Val Ile Tyr Ser Gly Gly Ser Ile Thr Tyr Ala Asp Ser Val Lys
    50                  55                  60

Gly Arg Phe Ile Ile Ser Arg Asp Asn Ser Asn Thr Leu Tyr Leu
65                  70                  75                  80

Gln Met Asn Gly Leu Arg Ala Glu Asp Thr Ala Val Tyr Tyr Cys Ala
            85                  90                  95

Arg Ala Val Pro His Ala Pro Ser Ala Phe Asp Ile Trp Gly Gln Gly
            100                 105                 110

Thr Met Val Thr Val Ser Ser
        115

<210> SEQ ID NO 124
<211> LENGTH: 10
<212> TYPE: PRT
<213> ORGANISM: Homo Sapiens

<400> SEQUENCE: 124

Gly Phe Thr Val Arg Asn Asn Tyr Met Ser
1               5                   10

<210> SEQ ID NO 125
<211> LENGTH: 16
<212> TYPE: PRT
<213> ORGANISM: Homo Sapiens

<400> SEQUENCE: 125

Val Ile Tyr Ser Gly Gly Ser Ile Thr Tyr Ala Asp Ser Val Lys Gly
1               5                   10                  15

<210> SEQ ID NO 126
<211> LENGTH: 11
<212> TYPE: PRT
<213> ORGANISM: Homo Sapiens

<400> SEQUENCE: 126

Ala Val Pro His Ala Pro Ser Ala Phe Asp Ile
1               5                   10

<210> SEQ ID NO 127
<211> LENGTH: 1116
<212> TYPE: DNA
<213> ORGANISM: Homo Sapiens

<400> SEQUENCE: 127

```
atggagaccg acaccctgct gctgtgggtg ctgctgctgt gggtgcccgg atccaccggc    60
tctgaggtgc agctggtgga gactggagga ggcttgatcc agcctggggg gtccctgaga   120
ctctcctgtg cagcctctgg gttcaccgtc agtagcaact acatgagctg ggtccgccag   180
gctccaggga aggggctgga gtgggtctca gttatttata gcggtggtag cacatactac   240
gcagactccg tgaagggccg attcaccatc tccagagaca attccaagaa cacgctgtat   300
cttcaaatga gcaacctgac cgccgaggac acggccgtgt attactgtgc gagagccgtt   360
ccccactccc ccagtgcttt tgataggtgg ggccagggaa ccctggtcac cgtctcttca   420
gagcccaaat cttgtgacaa aactcacaca tgcccaccgt gcccagcacc tgaactcctg   480
gggggaccgg acgtcttcct cttcccccca aaacccaagg acaccctcat gatctcccgg   540
acccctgagg tcacatgcgt ggtggtggac gtgagccacg aagaccctga ggtcaagttc   600
aactggtacg tggacggcgt ggaggtgcat aatgccaaga caaagccgcg ggaggagcag   660
tacaacagca cgtaccgggt ggtcagcgtc ctcaccgtcc tgcaccagga ctggctgaat   720
ggcaaggagt acaagtgcaa ggtctccaac aaagccctcc cagcccccga ggagaaaacc   780
atctccaaag ccaaagggca gccccgagaa ccacaggtgt acaccctgcc cccatcccgg   840
gaggagatga ccaagaacca ggtcagcctg acctgcctgg tcaaaggctt ctatcccagc   900
gacatcgccg tggagtggga gagcaatggg cagccggaga caactacaa gaccacgcct   960
cccgtgctgg actccgacgg ctccttcttc ctctacagca agctcaccgt ggacaagagc  1020
aggtggcagc aggggaacgt cttctcatgc tccgtgatgc atgaggctct gcacaaccac  1080
tacacgcaga agagcctctc cctgtctccg ggtaaa                           1116
```

<210> SEQ ID NO 128
<211> LENGTH: 372
<212> TYPE: PRT
<213> ORGANISM: Homo Sapiens

<400> SEQUENCE: 128

```
Met Glu Thr Asp Thr Leu Leu Leu Trp Val Leu Leu Trp Val Pro
1               5                   10                  15

Gly Ser Thr Gly Ser Glu Val Gln Leu Val Glu Thr Gly Gly Leu
                20                  25                  30

Ile Gln Pro Gly Gly Ser Leu Arg Leu Ser Cys Ala Ala Ser Gly Phe
            35                  40                  45

Thr Val Ser Ser Asn Tyr Met Ser Trp Val Arg Gln Ala Pro Gly Lys
    50                  55                  60

Gly Leu Glu Trp Val Ser Val Ile Tyr Ser Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Ser Asn Leu Thr Ala Glu Asp Thr Ala
                100                 105                 110

Val Tyr Tyr Cys Ala Arg Ala Val Pro His Ser Pro Ser Ala Phe Asp
                115                 120                 125

Arg Trp Gly Gln Gly Thr Leu Val Thr Val Ser Ser Glu Pro Lys Ser
130                 135                 140

Cys Asp Lys Thr His Thr Cys Pro Pro Cys Pro Ala Pro Glu Leu Leu
145                 150                 155                 160

Gly Gly Pro Asp Val Phe Leu Phe Pro Pro Lys Pro Lys Asp Thr Leu
                165                 170                 175

Met Ile Ser Arg Thr Pro Glu Val Thr Cys Val Val Val Asp Val Ser
                180                 185                 190

His Glu Asp Pro Glu Val Lys Phe Asn Trp Tyr Val Asp Gly Val Glu
                195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Glu Glu Lys Thr Ile Ser Lys Ala Lys Gly Gln Pro Arg Glu Pro Gln
                260                 265                 270

Val Tyr Thr Leu Pro Pro Ser Arg Glu Glu Met Thr Lys Asn Gln Val
                275                 280                 285

Ser Leu Thr Cys Leu Val Lys Gly Phe Tyr Pro Ser Asp Ile Ala Val
                290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
                340                 345                 350

Met His Glu Ala Leu His Asn His Tyr Thr Gln Lys Ser Leu Ser Leu
                355                 360                 365

Ser Pro Gly Lys
    370
```

<210> SEQ ID NO 129
<211> LENGTH: 119
<212> TYPE: PRT
<213> ORGANISM: Homo Sapiens

<400> SEQUENCE: 129

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Ser Asn Leu Thr Ala Glu Asp Thr Ala Val Tyr Tyr Cys Ala
                85                  90                  95

Arg Ala Val Pro His Ser Pro Ser Ala Phe Asp Arg Trp Gly Gln Gly
            100                 105                 110

Thr Leu Val Thr Val Ser Ser
        115

<210> SEQ ID NO 130
<211> LENGTH: 10
<212> TYPE: PRT
<213> ORGANISM: Homo Sapiens

<400> SEQUENCE: 130

Gly Phe Thr Val Ser Ser Asn Tyr Met Ser
1               5                   10

<210> SEQ ID NO 131
<211> LENGTH: 16
<212> TYPE: PRT
<213> ORGANISM: Homo Sapiens

<400> SEQUENCE: 131

Val Ile Tyr Ser Gly Gly Ser Thr Tyr Tyr Ala Asp Ser Val Lys Gly
1               5                   10                  15

<210> SEQ ID NO 132
<211> LENGTH: 11
<212> TYPE: PRT
<213> ORGANISM: Homo Sapiens

<400> SEQUENCE: 132

Ala Val Pro His Ser Pro Ser Ala Phe Asp Arg
1               5                   10

<210> SEQ ID NO 133
<211> LENGTH: 1116
<212> TYPE: DNA
<213> ORGANISM: Homo Sapiens

<400> SEQUENCE: 133
atggagaccg acaccctgct gctgtgggtg ctgctgctgt gggtgccgg  atccaccggc      60 tctgaggtgc agctggagga gactggagga gacttgatcc agccgggggg gtccctgaga     120
ctctcctgta cagcctctgg gtttaacgtc agtagaatct acatgagctg ggtccgccag     180

```
gctccaggga aggggctgga gtgggtctca gtgatttata gcggtggaag tatatattac      240
gcagattccg tgaggggccg atttaccatc tccagagaca gttccacgaa cacggtgtat      300
cttcaaatga acagcctgag agccgaggac tcggccgtgt attactgtgc gagagccgtc      360
ccacatgccc ctagtaattt tgataaatgg ggccaaggga caagggtcac cgtctcttca      420
gagcccaaat cttgtgacaa aactcacaca tgcccaccgt gcccagcacc tgaactcctg      480 ggggaccgg acgtcttcct cttcccccca aaacccaagg acaccctcat gatctcccgg       540 accctgagg tcacatgcgt ggtggtggac gtgagccacg aagaccctga ggtcaagttc       600
aactggtacg tggacggcgt ggaggtgcat aatgccaaga caaagccgcg ggaggagcag      660
tacaacagca cgtaccgggt ggtcagcgtc ctcaccgtcc tgcaccagga ctggctgaat      720
ggcaaggagt acaagtgcaa ggtctccaac aaagccctcc cagcccccga ggagaaaacc      780
atctccaaag ccaaagggca gccccgagaa ccacaggtgt acaccctgcc cccatcccgg      840
gaggagatga ccaagaacca ggtcagcctg acctgcctgg tcaaaggctt ctatcccagc      900
gacatcgccg tggagtggga gagcaatggg cagccggaga caactacaa gaccacgcct       960 cccgtgctgg actccgacgg ctccttcttc ctctacagca agctcaccgt ggacaagagc     1020
aggtggcagc aggggaacgt cttctcatgc tccgtgatgc atgaggctct gcacaaccac     1080
tacacgcaga gagcctctc cctgtctccg ggtaaa                                1116
```

<210> SEQ ID NO 134
<211> LENGTH: 372
<212> TYPE: PRT
<213> ORGANISM: Homo Sapiens

<400> SEQUENCE: 134

```
Met Glu Thr Asp Thr Leu Leu Leu Trp Val Leu Leu Leu Trp Val Pro
1               5                   10                  15

Gly Ser Thr Gly Ser Glu Val Gln Leu Glu Glu Thr Gly Gly Asp Leu
            20                  25                  30

Ile Gln Pro Gly Gly Ser Leu Arg Leu Ser Cys Thr Ala Ser Gly Phe
        35                  40                  45

Asn Val Ser Arg Ile Tyr Met Ser Trp Val Arg Gln Ala Pro Gly Lys
    50                  55                  60

Gly Leu Glu Trp Val Ser Val Ile Tyr Ser Gly Gly Ser Ile Tyr Tyr
65                  70                  75                  80

Ala Asp Ser Val Arg Gly Arg Phe Thr Ile Ser Arg Asp Ser Ser Thr
                85                  90                  95

Asn Thr Val Tyr Leu Gln Met Asn Ser Leu Arg Ala Glu Asp Ser Ala
            100                 105                 110

Val Tyr Tyr Cys Ala Arg Ala Val Pro His Ala Pro Ser Asn Phe Asp
        115                 120                 125

Lys Trp Gly Gln Gly Thr Arg Val Thr Val Ser Ser Glu Pro Lys Ser
    130                 135                 140

Cys Asp Lys Thr His Thr Cys Pro Pro Cys Pro Ala Pro Glu Leu Leu
145                 150                 155                 160

Gly Gly Pro Asp Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205
```

```
Val His Asn Ala Lys Thr Lys Pro Arg Glu Glu Gln Tyr Asn Ser Thr
    210                 215                 220
Tyr Arg Val Val Ser Val Leu Thr Val Leu His Gln Asp Trp Leu Asn
225                 230                 235                 240
Gly Lys Glu Tyr Lys Cys Lys Val Ser Asn Lys Ala Leu Pro Ala Pro
                245                 250                 255
Glu Glu Lys Thr Ile Ser Lys Ala Lys Gly Gln Pro Arg Glu Pro Gln
            260                 265                 270
Val Tyr Thr Leu Pro Pro Ser Arg Glu Glu Met Thr Lys Asn Gln Val
        275                 280                 285
Ser Leu Thr Cys Leu Val Lys Gly Phe Tyr Pro Ser Asp Ile Ala Val
    290                 295                 300
Glu Trp Glu Ser Asn Gly Gln Pro Glu Asn Asn Tyr Lys Thr Thr Pro
305                 310                 315                 320
Pro Val Leu Asp Ser Asp Gly Ser Phe Phe Leu Tyr Ser Lys Leu Thr
                325                 330                 335
Val Asp Lys Ser Arg Trp Gln Gln Gly Asn Val Phe Ser Cys Ser Val
            340                 345                 350
Met His Glu Ala Leu His Asn His Tyr Thr Gln Lys Ser Leu Ser Leu
        355                 360                 365
Ser Pro Gly Lys
    370

<210> SEQ ID NO 135
<211> LENGTH: 119
<212> TYPE: PRT
<213> ORGANISM: Homo Sapiens

<400> SEQUENCE: 135

Glu Val Gln Leu Glu Glu Thr Gly Gly Asp Leu Ile Gln Pro Gly Gly
1               5                   10                  15
Ser Leu Arg Leu Ser Cys Thr Ala Ser Gly Phe Asn Val Ser Arg Ile
            20                  25                  30
Tyr Met Ser Trp Val Arg Gln Ala Pro Gly Lys Gly Leu Glu Trp Val
        35                  40                  45
Ser Val Ile Tyr Ser Gly Gly Ser Ile Tyr Tyr Ala Asp Ser Val Arg
    50                  55                  60
Gly Arg Phe Thr Ile Ser Arg Asp Ser Ser Thr Asn Thr Val Tyr Leu
65                  70                  75                  80
Gln Met Asn Ser Leu Arg Ala Glu Asp Ser Ala Val Tyr Tyr Cys Ala
                85                  90                  95
Arg Ala Val Pro His Ala Pro Ser Asn Phe Asp Lys Trp Gly Gln Gly
            100                 105                 110
Thr Arg Val Thr Val Ser Ser
        115

<210> SEQ ID NO 136
<211> LENGTH: 10
<212> TYPE: PRT
<213> ORGANISM: Homo Sapiens

<400> SEQUENCE: 136

Gly Phe Asn Val Ser Arg Ile Tyr Met Ser
1               5                   10

<210> SEQ ID NO 137
<211> LENGTH: 16
```

-continued

<212> TYPE: PRT
<213> ORGANISM: Homo Sapiens

<400> SEQUENCE: 137

Val Ile Tyr Ser Gly Gly Ser Ile Tyr Tyr Ala Asp Ser Val Arg Gly
1               5                   10                  15

<210> SEQ ID NO 138
<211> LENGTH: 11
<212> TYPE: PRT
<213> ORGANISM: Homo Sapiens

<400> SEQUENCE: 138

Ala Val Pro His Ala Pro Ser Asn Phe Asp Lys
1               5                   10

<210> SEQ ID NO 139
<211> LENGTH: 1116
<212> TYPE: DNA
<213> ORGANISM: Homo Sapiens

<400> SEQUENCE: 139

```
atggagaccg acaccctgct gctgtgggtg ctgctgctgt gggtgcccgg atccaccggc      60
tctgaggtgc agctggcgga gactggagga ggcttgatcc agcctggggg gtccctgaga     120
ctctcctgtg cagtctctgg gttcaatgtc agtaagaatt acatgagctg ggtccgccag     180
gttccaggga aggggctgga gtgggtcgca gttgtttata gcggtggtag caaaacctac     240
gcagactccg tgaagggccg attcatcctc tccagagaca attccgacaa cacactgtat     300
cttcaaatga caacctgag agccgaggac acggccgtgt attactgtgc gagagccgtt     360
cctcattccc ccagttcttt tgatatctgg ggccaaggga caatggtcac cgtctcttca     420
gagcccaaat cttgtgacaa aactcacaca tgcccaccgt gcccagcacc tgaactcctg     480
gggggaccgg acgtcttcct cttccccca aaacccaagg acaccctcat gatctcccgg     540
acccctgagg tcacatgcgt ggtggtggac gtgagccacg aagaccctga ggtcaagttc     600
aactggtacg tggacggcgt ggaggtgcat aatgccaaga caaagccgcg ggaggagcag     660
tacaacagca cgtaccgggt ggtcagcgtc ctcaccgtcc tgcaccagga ctggctgaat     720
ggcaaggagt acaagtgcaa ggtctccaac aaagccctcc cagccccga ggagaaaacc     780
atctccaaag ccaagggca gccccgagaa ccacaggtgt acaccctgcc cccatcccgg     840
gaggagatga ccaagaacca ggtcagcctg acctgcctgg tcaaaggctt ctatcccagc     900
gacatcgccg tggagtggga gagcaatggg cagccggaga caactacaa gaccacgcct     960
cccgtgctgg actccgacgg ctccttcttc ctctacagca agctcaccgt ggacaagagc    1020
aggtggcagc aggggaacgt cttctcatgc tccgtgatgc atgaggctct gcacaaccac    1080
tacacgcaga agagcctctc cctgtctccg ggtaaa                              1116
```

<210> SEQ ID NO 140
<211> LENGTH: 372
<212> TYPE: PRT
<213> ORGANISM: Homo Sapiens

<400> SEQUENCE: 140

Met Glu Thr Asp Thr Leu Leu Leu Trp Val Leu Leu Leu Trp Val Pro
1               5                   10                  15

Gly Ser Thr Gly Ser Glu Val Gln Leu Ala Glu Thr Gly Gly Gly Leu
                20                  25                  30

Ile Gln Pro Gly Gly Ser Leu Arg Leu Ser Cys Ala Val Ser Gly Phe
        35                  40                  45

Asn Val Ser Lys Asn Tyr Met Ser Trp Val Arg Gln Val Pro Gly Lys
 50                  55                  60

Gly Leu Glu Trp Val Ala Val Tyr Ser Gly Gly Ser Lys Thr Tyr
 65                  70                  75                  80

Ala Asp Ser Val Lys Gly Arg Phe Ile Leu Ser Arg Asp Asn Ser Asp
                 85                  90                  95

Asn Thr Leu Tyr Leu Gln Met Asn Asn Leu Arg Ala Glu Asp Thr Ala
             100                 105                 110

Val Tyr Tyr Cys Ala Arg Ala Val Pro His Ser Pro Ser Ser Phe Asp
         115                 120                 125

Ile Trp Gly Gln Gly Thr Met Val Thr Val Ser Ser Glu Pro Lys Ser
 130                 135                 140

Cys Asp Lys Thr His Thr Cys Pro Pro Cys Pro Ala Pro Glu Leu Leu
145                 150                 155                 160

Gly Gly Pro Asp Val Phe Leu Phe Pro Pro Lys Pro Lys Asp Thr Leu
                 165                 170                 175

Met Ile Ser Arg Thr Pro Glu Val Thr Cys Val Val Val Asp Val Ser
             180                 185                 190

His Glu Asp Pro Glu Val Lys Phe Asn Trp Tyr Val Asp Gly Val Glu
         195                 200                 205

Val His Asn Ala Lys Thr Lys Pro Arg Glu Glu Gln Tyr Asn Ser Thr
 210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                 245                 250                 255

Glu Glu Lys Thr Ile Ser Lys Ala Lys Gly Gln Pro Arg Glu Pro Gln
             260                 265                 270

Val Tyr Thr Leu Pro Pro Ser Arg Glu Glu Met Thr Lys Asn Gln Val
         275                 280                 285

Ser Leu Thr Cys Leu Val Lys Gly Phe Tyr Pro Ser Asp Ile Ala Val
 290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                 325                 330                 335

Val Asp Lys Ser Arg Trp Gln Gln Gly Asn Val Phe Ser Cys Ser Val
             340                 345                 350

Met His Glu Ala Leu His Asn His Tyr Thr Gln Lys Ser Leu Ser Leu
         355                 360                 365

Ser Pro Gly Lys
 370

<210> SEQ ID NO 141
<211> LENGTH: 119
<212> TYPE: PRT
<213> ORGANISM: Homo Sapiens

<400> SEQUENCE: 141

Glu Val Gln Leu Ala Glu Thr Gly Gly Gly Leu Ile Gln Pro Gly Gly
1               5                   10                  15

Ser Leu Arg Leu Ser Cys Ala Val Ser Gly Phe Asn Val Ser Lys Asn
             20                  25                  30

```
Tyr Met Ser Trp Val Arg Gln Val Pro Gly Lys Gly Leu Glu Trp Val
         35                  40                  45
Ala Val Val Tyr Ser Gly Gly Ser Lys Thr Tyr Ala Asp Ser Val Lys
     50                  55                  60
Gly Arg Phe Ile Leu Ser Arg Asp Asn Ser Asn Thr Leu Tyr Leu
 65              70                  75                  80
Gln Met Asn Asn Leu Arg Ala Glu Asp Thr Ala Val Tyr Tyr Cys Ala
                 85                  90                  95
Arg Ala Val Pro His Ser Pro Ser Ser Phe Asp Ile Trp Gly Gln Gly
             100                 105                 110
Thr Met Val Thr Val Ser Ser
         115

<210> SEQ ID NO 142
<211> LENGTH: 10
<212> TYPE: PRT
<213> ORGANISM: Homo Sapiens

<400> SEQUENCE: 142

Gly Phe Asn Val Ser Lys Asn Tyr Met Ser
1               5                   10

<210> SEQ ID NO 143
<211> LENGTH: 16
<212> TYPE: PRT
<213> ORGANISM: Homo Sapiens

<400> SEQUENCE: 143

Val Val Tyr Ser Gly Gly Ser Lys Thr Tyr Ala Asp Ser Val Lys Gly
1               5                   10                  15

<210> SEQ ID NO 144
<211> LENGTH: 11
<212> TYPE: PRT
<213> ORGANISM: Homo Sapiens

<400> SEQUENCE: 144

Ala Val Pro His Ser Pro Ser Ser Phe Asp Ile
1               5                   10

<210> SEQ ID NO 145
<211> LENGTH: 1116
<212> TYPE: DNA
<213> ORGANISM: Homo Sapiens

<400> SEQUENCE: 145
atggagaccg acaccctgct gctgtgggtg ctgctgctgt gggtgcccgg atccaccggc      60
tctgaggtgc agctggcgga gactggagga ggcttgatcc agcctggggg gtccctgaga     120
ctctcctgtg cagtctctgg gttcaccgtc agtaagaatt acatgagctg ggtccgccag     180
gttccaggga aggggctgga gtgggtcgca gttgtttata gcggtggtag caaaacctac     240
gcagactccg tgaagggccg attcatcctc tccagagaca attccgacaa cacactgtat     300
cttcaaatga acaacctgag agccgaggac acggccgtgt attactgtgc gagagccgtt     360
cctcattccc ccagttcttt tgatatctgg ggccaaggga caatggtcac cgtctcttca     420
gagcccaaat cttgtgacaa aactcacaca tgcccaccgt gcccagcacc tgaactcctg     480
gggggaccgg acgtcttcct cttcccccca aaacccaagg acaccctcat gatctcccgg     540
acccctgagg tcacatgcgt ggtggtggac gtgagccacg aagaccctga ggtcaagttc     600
```

```
aactggtacg tggacggcgt ggaggtgcat aatgccaaga caaagccgcg ggaggagcag    660
tacaacagca cgtaccgggt ggtcagcgtc ctcaccgtcc tgcaccagga ctggctgaat    720
ggcaaggagt acaagtgcaa ggtctccaac aaagccctcc cagccccga ggagaaaacc    780 atctccaaag ccaagggca gccccgagaa ccacaggtgt acaccctgcc cccatcccgg    840
gaggagatga ccaagaacca ggtcagcctg acctgcctgg tcaaaggctt ctatcccagc    900
gacatcgccg tggagtggga gagcaatggg cagccggaga caactacaa gaccacgcct    960 cccgtgctgg actccgacgg ctccttcttc ctctacagca agctcaccgt ggacaagagc   1020
aggtggcagc aggggaacgt cttctcatgc tccgtgatgc atgaggctct gcacaaccac   1080
tacacgcaga agagcctctc cctgtctccg ggtaaa                              1116
```

<210> SEQ ID NO 146
<211> LENGTH: 372
<212> TYPE: PRT
<213> ORGANISM: Homo Sapiens

<400> SEQUENCE: 146

```
Met Glu Thr Asp Thr Leu Leu Leu Trp Val Leu Leu Leu Trp Val Pro
1               5                   10                  15

Gly Ser Thr Gly Ser Glu Val Gln Leu Ala Glu Thr Gly Gly Gly Leu
            20                  25                  30

Ile Gln Pro Gly Gly Ser Leu Arg Leu Ser Cys Ala Val Ser Gly Phe
        35                  40                  45

Thr Val Ser Lys Asn Tyr Met Ser Trp Val Arg Gln Val Pro Gly Lys
    50                  55                  60

Gly Leu Glu Trp Val Ala Val Val Tyr Ser Gly Gly Ser Lys Thr Tyr
65                  70                  75                  80

Ala Asp Ser Val Lys Gly Arg Phe Ile Leu Ser Arg Asp Asn Ser Asp
                85                  90                  95

Asn Thr Leu Tyr Leu Gln Met Asn Asn Leu Arg Ala Glu Asp Thr Ala
            100                 105                 110

Val Tyr Tyr Cys Ala Arg Ala Val Pro His Ser Pro Ser Ser Phe Asp
        115                 120                 125

Ile Trp Gly Gln Gly Thr Met Val Thr Val Ser Ser Glu Pro Lys Ser
    130                 135                 140

Cys Asp Lys Thr His Thr Cys Pro Pro Cys Pro Ala Pro Glu Leu Leu
145                 150                 155                 160

Gly Gly Pro Asp Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Glu Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
```

```
                 275                 280                 285
    Ser Leu Thr Cys Leu Val Lys Gly Phe Tyr Pro Ser Asp Ile Ala Val
        290                 295                 300

Glu Trp Glu Ser Asn Gly Gln Pro Glu Asn Asn Tyr Lys Thr Thr Pro
    305                 310                 315                 320

Pro Val Leu Asp Ser Asp Gly Ser Phe Phe Leu Tyr Ser Lys Leu Thr
                    325                 330                 335

Val Asp Lys Ser Arg Trp Gln Gln Gly Asn Val Phe Ser Cys Ser Val
                340                 345                 350

Met His Glu Ala Leu His Asn His Tyr Thr Gln Lys Ser Leu Ser Leu
                355                 360                 365

Ser Pro Gly Lys
        370

<210> SEQ ID NO 147
<211> LENGTH: 119
<212> TYPE: PRT
<213> ORGANISM: Homo Sapiens

<400> SEQUENCE: 147

Glu Val Gln Leu Ala Glu Thr Gly Gly Gly Leu Ile Gln Pro Gly Gly
    1               5                   10                  15

Ser Leu Arg Leu Ser Cys Ala Val Ser Gly Phe Thr Val Ser Lys Asn
                20                  25                  30

Tyr Met Ser Trp Val Arg Gln Val Pro Gly Lys Gly Leu Glu Trp Val
                35                  40                  45

Ala Val Val Tyr Ser Gly Gly Ser Lys Thr Tyr Ala Asp Ser Val Lys
        50                  55                  60

Gly Arg Phe Ile Leu Ser Arg Asp Asn Ser Asp Asn Thr Leu Tyr Leu
    65                  70                  75                  80

Gln Met Asn Asn Leu Arg Ala Glu Asp Thr Ala Val Tyr Tyr Cys Ala
                    85                  90                  95

Arg Ala Val Pro His Ser Pro Ser Ser Phe Asp Ile Trp Gly Gln Gly
                100                 105                 110

Thr Met Val Thr Val Ser Ser
            115

<210> SEQ ID NO 148
<211> LENGTH: 10
<212> TYPE: PRT
<213> ORGANISM: Homo Sapiens

<400> SEQUENCE: 148

Gly Phe Thr Val Ser Lys Asn Tyr Met Ser
    1               5                   10

<210> SEQ ID NO 149
<211> LENGTH: 16
<212> TYPE: PRT
<213> ORGANISM: Homo Sapiens

<400> SEQUENCE: 149

Val Val Tyr Ser Gly Gly Ser Lys Thr Tyr Ala Asp Ser Val Lys Gly
    1               5                   10                  15

<210> SEQ ID NO 150
<211> LENGTH: 11
<212> TYPE: PRT
<213> ORGANISM: Homo Sapiens
```

<400> SEQUENCE: 150

Ala Val Pro His Ser Pro Ser Ser Phe Asp Ile
1               5                   10

<210> SEQ ID NO 151
<211> LENGTH: 1116
<212> TYPE: DNA
<213> ORGANISM: Homo Sapiens

<400> SEQUENCE: 151

```
atggagaccg acaccctgct gctgtgggtg ctgctgctgt gggtgcccgg atccaccggc      60
tctgaggtgc agctggtgga gagcggagga ggcttgatcc agcctggggg gtccctgaga     120
ctctcctgtg cagtctctgg gttcaccgtc agtaagaatt acatgagctg ggtccgccag     180
gccccaggga aggggctgga gtgggtcagc gttgtttata gcggtggtag caaaacctac     240
gcagactccg tgaagggccg attcaccatc tccagagaca attccaagaa cacactgtat     300
cttcaaatga acagcctgag agccgaggac acggccgtgt attactgtgc gagagccgtt     360
cctcattccc ccagttcttt tgatatctgg ggccaaggga caatggtcac cgtctcttca     420
gagcccaaat cttgtgacaa aactcacaca tgcccaccgt gcccagcacc tgaactcctg     480
gggggaccgg acgtcttcct cttcccccca aaacccaagg acaccctcat gatctcccgg     540
acccctgagg tcacatgcgt ggtggtggac gtgagccacg aagaccctga ggtcaagttc     600
aactggtacg tggacggcgt ggaggtgcat aatgccaaga caaagccgcg ggaggagcag     660
tacaacagca cgtaccgggt ggtcagcgtc ctcaccgtcc tgcaccagga ctggctgaat     720
ggcaaggagt acaagtgcaa ggtctccaac aaagccctcc cagccccga ggagaaaacc     780
atctccaaag ccaagggca gccccgagaa ccacaggtgt acaccctgcc cccatcccgg     840
gaggagatga ccaagaacca ggtcagcctg acctgcctgg tcaaaggctt ctatcccagc     900
gacatcgccg tggagtggga gagcaatggg cagccggaga acaactacaa gaccacgcct     960
cccgtgctgg actccgacgg ctccttcttc ctctacagca agctcaccgt ggacaagagc    1020
aggtggcagc aggggaacgt cttctcatgc tccgtgatgc atgaggctct gcacaaccac    1080
tacacgcaga agagcctctc cctgtctccg ggtaaa                              1116
```

<210> SEQ ID NO 152
<211> LENGTH: 372
<212> TYPE: PRT
<213> ORGANISM: Homo Sapiens

<400> SEQUENCE: 152

Met Glu Thr Asp Thr Leu Leu Leu Trp Val Leu Leu Leu Trp Val Pro
1               5                   10                  15

Gly Ser Thr Gly Ser Glu Val Gln Leu Val Glu Ser Gly Gly Gly Leu
            20                  25                  30

Ile Gln Pro Gly Gly Ser Leu Arg Leu Ser Cys Ala Val Ser Gly Phe
        35                  40                  45

Thr Val Ser Lys Asn Tyr Met Ser Trp Val Arg Gln Ala Pro Gly Lys
    50                  55                  60

Gly Leu Glu Trp Val Ser Val Val Tyr Ser Gly Gly Ser Lys Thr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala

```
                100             105             110
Val Tyr Tyr Cys Ala Arg Ala Val Pro His Ser Pro Ser Ser Phe Asp
            115                 120             125

Ile Trp Gly Gln Gly Thr Met Val Thr Val Ser Ser Glu Pro Lys Ser
130                 135                 140

Cys Asp Lys Thr His Thr Cys Pro Pro Cys Pro Ala Pro Glu Leu Leu
145                 150                 155                 160

Gly Gly Pro Asp Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Glu Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
        355                 360                 365

Ser Pro Gly Lys
    370

<210> SEQ ID NO 153
<211> LENGTH: 119
<212> TYPE: PRT
<213> ORGANISM: Homo Sapiens

<400> SEQUENCE: 153

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Thr Val Ser Lys Asn
            20                  25                  30

Tyr Met Ser Trp Val Arg Gln Ala Pro Gly Lys Gly Leu Glu Trp Val
        35                  40                  45

Ser Val Val Tyr Ser Gly Gly Ser Lys Thr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

Arg Ala Val Pro His Ser Pro Ser Ser Phe Asp Ile Trp Gly Gln Gly
            100                 105                 110
Thr Met Val Thr Val Ser Ser
        115

<210> SEQ ID NO 154
<211> LENGTH: 10
<212> TYPE: PRT
<213> ORGANISM: Homo Sapiens

<400> SEQUENCE: 154

Gly Phe Thr Val Ser Lys Asn Tyr Met Ser
1               5                   10

<210> SEQ ID NO 155
<211> LENGTH: 16
<212> TYPE: PRT
<213> ORGANISM: Homo Sapiens

<400> SEQUENCE: 155

Val Val Tyr Ser Gly Gly Ser Lys Thr Tyr Ala Asp Ser Val Lys Gly
1               5                   10                  15

<210> SEQ ID NO 156
<211> LENGTH: 11
<212> TYPE: PRT
<213> ORGANISM: Homo Sapiens

<400> SEQUENCE: 156

Ala Val Pro His Ser Pro Ser Ser Phe Asp Ile
1               5                   10

<210> SEQ ID NO 157
<211> LENGTH: 1116
<212> TYPE: DNA
<213> ORGANISM: Homo Sapiens

<400> SEQUENCE: 157
atggagaccg acaccctgct gctgtgggtg ctgctgctgt gggtgcccgg atccaccggc      60
gaggtgcagc tggtggagtc cgggggaggc ttagttcagc ctggggggtc cctgagactc     120
tcctgtgcag cctctggatt caccttcagt aactactgga tgcactgggt ccgccaagct     180
ccagggaagg ggctggtgtg ggtctcacgt attaatagtg atgggagtaa cacaacctac     240
gcggactccg tgaagggccg attcaccatc tccagagaca acgccaagaa cacgctgtat     300
ctgcaaatga acagtctgag agccgaggac acggctgtgt attactgtgc aagatggttc     360
ggggagcact actacggaat ggacgtctgg ggccaaggga ccacggtcac cgtctcttca     420
gagcccaaat cttgtgacaa aactcacaca tgcccaccgt gcccagcacc tgaactcctg     480
gggggaccgt cagtcttcct cttccccccca aaacccaagg acaccctcat gatctcccgg     540
acccctgagg tcacatgcgt ggtggtggac gtgagccacg aagaccctga ggtcaagttc     600
aactggtacg tggacggcgt ggaggtgcat aatgccaaga caaagccgcg ggaggagcag     660
tacaacagca cgtaccgggt ggtcagcgtc ctcaccgtcc tgcaccagga ctggctgaat     720
ggcaaggagt acaagtgcaa ggtctccaac aaagccctcc cagcccccat cgagaaaacc     780
atctccaaag ccaaagggca gccccgagaa ccacaggtgt acaccctgcc cccatcccgg     840
gaggagatga ccaagaacca ggtcagcctg acctgcctgg tcaaaggctt ctatcccagc     900
gacatcgccg tggagtggga gagcaatggg cagccggaga caactacaa gaccacgcct     960

```
cccgtgctgg actccgacgg ctccttcttc ctctacagca agctcaccgt ggacaagagc    1020
aggtggcagc aggggaacgt cttctcatgc tccgtgatgc atgaggctct gcacaaccac    1080
tacacgcaga agagcctctc cctgtctccg ggtaaa                              1116
```

<210> SEQ ID NO 158
<211> LENGTH: 372
<212> TYPE: PRT
<213> ORGANISM: Homo Sapiens

<400> SEQUENCE: 158

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asn Tyr Trp Met His Trp Val Arg Gln Ala Pro Gly Lys Gly
    50                  55                  60

Leu Val Trp Val Ser Arg Ile Asn Ser Asp Gly Ser Asn Thr Thr Tyr
65                  70                  75                  80

Ala Asp Ser Val Lys Gly Arg Phe Thr Ile Ser Arg Asp Asn Ala Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Trp Phe Gly Glu His Tyr Tyr Gly Met Asp
        115                 120                 125

Val Trp Gly Gln Gly Thr Thr Val Thr Val Ser Ser Glu Pro Lys Ser
130                 135                 140

Cys Asp Lys Thr His Thr Cys Pro Pro Cys Pro Ala Pro Glu Leu Leu
145                 150                 155                 160

Gly Gly Pro Ser Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Ile Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300

Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350
```

```
Met His Glu Ala Leu His Asn His Tyr Thr Gln Lys Ser Leu Ser Leu
        355                 360                 365
Ser Pro Gly Lys
    370

<210> SEQ ID NO 159
<211> LENGTH: 120
<212> TYPE: PRT
<213> ORGANISM: Homo Sapiens

<400> SEQUENCE: 159

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Asn Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Phe Gly Glu His Tyr Tyr Gly Met Asp Val Trp Gly Gln
            100                 105                 110

Gly Thr Thr Val Thr Val Ser Ser
        115                 120

<210> SEQ ID NO 160
<211> LENGTH: 10
<212> TYPE: PRT
<213> ORGANISM: Homo Sapiens

<400> SEQUENCE: 160

Gly Phe Thr Phe Ser Asn Tyr Trp Met His
1               5                   10

<210> SEQ ID NO 161
<211> LENGTH: 17
<212> TYPE: PRT
<213> ORGANISM: Homo Sapiens

<400> SEQUENCE: 161

Arg Ile Asn Ser Asp Gly Ser Asn Thr Thr Tyr Ala Asp Ser Val Lys
1               5                   10                  15

Gly

<210> SEQ ID NO 162
<211> LENGTH: 11
<212> TYPE: PRT
<213> ORGANISM: Homo Sapiens

<400> SEQUENCE: 162

Trp Phe Gly Glu His Tyr Tyr Gly Met Asp Val
1               5                   10

<210> SEQ ID NO 163
<211> LENGTH: 1113
<212> TYPE: DNA
<213> ORGANISM: Homo Sapiens
```

-continued

<400> SEQUENCE: 163

```
atggagaccg acaccctgct gctgtgggtg ctgctgctgt gggtgcccgg atccaccggc    60
gaggtgcagc tggtggagag cggaggaggc ttgatccagc cggggggggtc cctgagactc   120
tcctgtgccg cctctgggtt taccgtcagt agaatctaca tgagctgggt ccgccaggct   180
ccagggaagg ggctggagtg ggtctcagtg atttatagcg gtggaagtat atattacgca   240
gattccgtga agggccgatt taccatctcc agagacagtt ccaagaacac ggtgtacctt   300
caaatgaaca gcctgagagc cgaggacacc gccgtgtatt actgtgcgag agccgtccca   360
agtgccccta gttcttttga tatctggggc caagggacaa tggtcaccgt ctcttcagag   420
cccaaatctt gtgacaaaac tcacacatgc ccaccgtgcc cagcacctga actcctgggg   480
ggaccgtcag tcttcctctt ccccccaaaa cccaaggaca ccctcatgat ctcccggacc   540
cctgaggtca catgcgtggt ggtggacgtg agccacgaag accctgaggt caagttcaac   600
tggtacgtgg acggcgtgga ggtgcataat gccaagacaa agccgcggga ggagcagtac   660
aacagcacgt accgggtggt cagcgtcctc accgtcctgc accaggactg gctgaatggc   720
aaggagtaca agtgcaaggt ctccaacaaa gccctcccag cccccatcga gaaaaccatc   780
tccaaagcca agggcagccc cgagaaccag gtgtacaccc tgcccccatc ccgggag     840
gagatgacca gaaccaggt cagcctgacc tgcctggtca aaggcttcta tcccagcgac   900
atcgccgtgg agtgggagag caatgggcag ccggagaaca actacaagac cacgcctccc   960
gtgctggact ccgacggctc cttcttcctc tacagcaagc tcaccgtgga caagagcagg  1020
tggcagcagg ggaacgtctt ctcatgctcc gtgatgcatg aggctctgca caaccactac  1080
acgcagaaga gcctctccct gtctccgggt aaa                               1113
```

<210> SEQ ID NO 164
<211> LENGTH: 371
<212> TYPE: PRT
<213> ORGANISM: Homo Sapiens

<400> SEQUENCE: 164

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Ile
            20                  25                  30

Gln Pro Gly Gly Ser Leu Arg Leu Ser Cys Ala Ala Ser Gly Phe Thr
        35                  40                  45

Val Ser Arg Ile Tyr Met Ser Trp Val Arg Gln Ala Pro Gly Lys Gly
    50                  55                  60

Leu Glu Trp Val Ser Val Ile Tyr Ser Gly Gly Ser Ile Tyr Tyr Ala
65                  70                  75                  80

Asp Ser Val Lys Gly Arg Phe Thr Ile Ser Arg Asp Ser Ser Lys Asn
                85                  90                  95

Thr Val Tyr Leu Gln Met Asn Ser Leu Arg Ala Glu Asp Thr Ala Val
            100                 105                 110

Tyr Tyr Cys Ala Arg Ala Val Pro Ser Ala Pro Ser Ser Phe Asp Ile
        115                 120                 125

Trp Gly Gln Gly Thr Met Val Thr Val Ser Ser Glu Pro Lys Ser Cys
    130                 135                 140

Asp Lys Thr His Thr Cys Pro Pro Cys Pro Ala Pro Glu Leu Leu Gly
145                 150                 155                 160
```

```
Gly Pro Ser Val Phe Leu Phe Pro Pro Lys Pro Lys Asp Thr Leu Met
            165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
            195                 200                 205

His Asn Ala Lys Thr Lys Pro Arg Glu Glu Gln Tyr Asn Ser Thr Tyr
            210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ala Pro Ile
            245                 250                 255

Glu Lys Thr Ile Ser Lys Ala Lys Gly Gln Pro Arg Glu Pro Gln Val
            260                 265                 270

Tyr Thr Leu Pro Pro Ser Arg Glu Glu Met Thr Lys Asn Gln Val Ser
            275                 280                 285

Leu Thr Cys Leu Val Lys Gly Phe Tyr Pro Ser Asp Ile Ala Val Glu
            290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
            325                 330                 335

Asp Lys Ser Arg Trp Gln Gln Gly Asn Val Phe Ser Cys Ser Val Met
            340                 345                 350

His Glu Ala Leu His Asn His Tyr Thr Gln Lys Ser Leu Ser Leu Ser
            355                 360                 365

Pro Gly Lys
    370

<210> SEQ ID NO 165
<211> LENGTH: 119
<212> TYPE: PRT
<213> ORGANISM: Homo Sapiens

<400> SEQUENCE: 165

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Arg Ile
            20                  25                  30

Tyr Met Ser Trp Val Arg Gln Ala Pro Gly Lys Gly Leu Glu Trp Val
            35                  40                  45

Ser Val Ile Tyr Ser Gly Gly Ser Ile Tyr Tyr Ala Asp Ser Val Lys
        50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
            85                  90                  95

Arg Ala Val Pro Ser Ala Pro Ser Ser Phe Asp Ile Trp Gly Gln Gly
            100                 105                 110

Thr Met Val Thr Val Ser Ser
        115

<210> SEQ ID NO 166
<211> LENGTH: 10
<212> TYPE: PRT
<213> ORGANISM: Homo Sapiens
```

<400> SEQUENCE: 166

Gly Phe Thr Val Ser Arg Ile Tyr Met Ser
1               5                   10

<210> SEQ ID NO 167
<211> LENGTH: 16
<212> TYPE: PRT
<213> ORGANISM: Homo Sapiens

<400> SEQUENCE: 167

Val Ile Tyr Ser Gly Gly Ser Ile Tyr Tyr Ala Asp Ser Val Lys Gly
1               5                   10                  15

<210> SEQ ID NO 168
<211> LENGTH: 11
<212> TYPE: PRT
<213> ORGANISM: Homo Sapiens

<400> SEQUENCE: 168

Ala Val Pro Ser Ala Pro Ser Ser Phe Asp Ile
1               5                   10

<210> SEQ ID NO 169
<211> LENGTH: 1113
<212> TYPE: DNA
<213> ORGANISM: Homo Sapiens

<400> SEQUENCE: 169

| | |
|---|---|
| atggagaccg acaccctgct gctgtgggtg ctgctgctgt gggtgcccgg atccaccggc | 60 |
| gaggtgcagc tggtggagag cggaggaggc ttgatccagc ctggggggtc cctgagactc | 120 |
| tcctgtgcag tctctgggtt caccgtcagt aagaattaca tgagctgggt ccgccaggcc | 180 |
| ccagggaagg ggctggagtg ggtcagcgtt gtttatagcg gtggtagcaa aacctacgca | 240 |
| gactccgtga agggccgatt caccatctcc agagacaatt ccaagaacac actgtatctt | 300 |
| caaatgaaca gcctgagagc cgaggacacg gccgtgtatt actgtgcgag agccgttcct | 360 |
| cattccccca gttcttttga tatctggggc caagggacaa tggtcaccgt ctcttcagag | 420 |
| cccaaatctt gtgacaaaac tcacacatgc ccaccgtgcc cagcacctga actcctgggg | 480 |
| ggaccgtcag tcttcctctt ccccccaaaa cccaaggaca cccctcatga tctcccggacc | 540 |
| cctgaggtca catgcgtggt ggtggacgtg agccacgaag accctgaggt caagttcaac | 600 |
| tggtacgtgg acggcgtgga ggtgcataat gccaagacaa agccgcggga ggagcagtac | 660 |
| aacagcacgt accgggtggt cagcgtcctc accgtcctgc accaggactg gctgaatggc | 720 |
| aaggagtaca agtgcaaggt ctccaacaaa gccctcccag cccccatcga gaaaaccatc | 780 |
| tccaaagcca aagggcagcc ccgagaacca caggtgtaca ccctgccccc atcccgggag | 840 |
| gagatgacca agaaccaggt cagcctgacc tgcctggtca aaggcttcta tcccagcgac | 900 |
| atcgccgtgg agtgggagag caatgggcag ccggagaaca actacaagac cacgcctccc | 960 |
| gtgctggact ccgacggctc cttcttcctc tacagcaagc tcaccgtgga caagagcagg | 1020 |
| tggcagcagg ggaacgtctt ctcatgctcc gtgatgcatg aggctctgca caaccactac | 1080 |
| acgcagaaga gcctctccct gtctccgggt aaa | 1113 |

<210> SEQ ID NO 170
<211> LENGTH: 371
<212> TYPE: PRT
<213> ORGANISM: Homo Sapiens

<400> SEQUENCE: 170

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Ile
            20                  25                  30

Gln Pro Gly Gly Ser Leu Arg Leu Ser Cys Ala Val Ser Gly Phe Thr
        35                  40                  45

Val Ser Lys Asn Tyr Met Ser Trp Val Arg Gln Ala Pro Gly Lys Gly
    50                  55                  60

Leu Glu Trp Val Ser Val Val Tyr Ser Gly Gly Ser Lys Thr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Val Pro His Ser Pro Ser Ser Phe Asp Ile
        115                 120                 125

Trp Gly Gln Gly Thr Met Val Thr Val Ser Ser Glu Pro Lys Ser Cys
130                 135                 140

Asp Lys Thr His Thr Cys Pro Pro Cys Pro Ala Pro Glu Leu Leu Gly
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
        195                 200                 205

His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ala Pro Ile
                245                 250                 255

Glu Lys Thr Ile Ser Lys Ala Lys Gly Gln Pro Arg Glu Pro Gln Val
            260                 265                 270

Tyr Thr Leu Pro Pro Ser Arg Glu Glu Met Thr Lys Asn Gln Val Ser
        275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
            340                 345                 350

His Glu Ala Leu His Asn His Tyr Thr Gln Lys Ser Leu Ser Leu Ser
        355                 360                 365

Pro Gly Lys
        370

<210> SEQ ID NO 171
<211> LENGTH: 119
<212> TYPE: PRT
```

-continued

<213> ORGANISM: Homo Sapiens

<400> SEQUENCE: 171

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Thr Val Ser Lys Asn
            20                  25                  30

Tyr Met Ser Trp Val Arg Gln Ala Pro Gly Lys Gly Leu Glu Trp Val
        35                  40                  45

Ser Val Val Tyr Ser Gly Gly Ser Lys Thr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Val Pro His Ser Pro Ser Ser Phe Asp Ile Trp Gly Gln Gly
            100                 105                 110

Thr Met Val Thr Val Ser Ser
        115

<210> SEQ ID NO 172
<211> LENGTH: 10
<212> TYPE: PRT
<213> ORGANISM: Homo Sapiens

<400> SEQUENCE: 172

Gly Phe Thr Val Ser Lys Asn Tyr Met Ser
1               5                   10

<210> SEQ ID NO 173
<211> LENGTH: 16
<212> TYPE: PRT
<213> ORGANISM: Homo Sapiens

<400> SEQUENCE: 173

Val Val Tyr Ser Gly Gly Ser Lys Thr Tyr Ala Asp Ser Val Lys Gly
1               5                   10                  15

<210> SEQ ID NO 174
<211> LENGTH: 11
<212> TYPE: PRT
<213> ORGANISM: Homo Sapiens

<400> SEQUENCE: 174

Ala Val Pro His Ser Pro Ser Ser Phe Asp Ile
1               5                   10

<210> SEQ ID NO 175
<211> LENGTH: 1113
<212> TYPE: DNA
<213> ORGANISM: Homo Sapiens

<400> SEQUENCE: 175
atggagaccg acaccctgct gctgtgggtg ctgctgctgt gggtgcccgg atccaccggc      60
gaggtgcagc tggtggagag cggaggaggc ttgatccagc cggggggtc cctgagactc     120 tcctgtgccg cctctgggtt taccgtcagt agaatctaca tgagctgggt ccgccaggct     180
ccagggaagg ggctggagtg gtctcagtg atttatagcg gtggaagtat atattacgca     240
gattccgtga agggccgatt taccatctcc agagacagtt ccaagaacac ggtgtacctt     300

```
caaatgaaca gcctgagagc cgaggacacc gccgtgtatt actgtgcgag agccgtccca    360
agtgccccta gttcttttga tatctggggc caagggacaa tggtcaccgt ctcttcagag    420
cccaaatctt gtgacaaaac tcacacatgc ccaccgtgcc cagcacctga actcctgggg    480
ggaccggacg tcttcctctt ccccccaaaa cccaaggaca ccctcatgat ctcccggacc    540
cctgaggtca catgcgtggt ggtggacgtg agccacgaag accctgaggt caagttcaac    600
tggtacgtgg acggcgtgga ggtgcataat gccaagacaa agccgcggga ggagcagtac    660
aacagcacgt accgggtggt cagcgtcctc accgtcctgc accaggactg gctgaatggc    720
aaggagtaca agtgcaaggt ctccaacaaa gccctcccag cccccgagga gaaaaccatc    780
tccaaagcca aagggcagcc ccgagaacca caggtgtaca ccctgccccc atcccgggag    840
gagatgacca agaaccaggt cagcctgacc tgcctggtca aaggcttcta tcccagcgac    900
atcgccgtgg agtgggagag caatgggcag ccggagaaca actacaagac cacgcctccc    960
gtgctggact ccgacggctc cttcttcctc tacagcaagc tcaccgtgga caagagcagg   1020
tggcagcagg ggaacgtctt ctcatgctcc gtgatgcatg aggctctgca caaccactac   1080
acgcagaaga gcctctccct gtctccgggt aaa                                1113
```

<210> SEQ ID NO 176
<211> LENGTH: 371
<212> TYPE: PRT
<213> ORGANISM: Homo Sapiens

<400> SEQUENCE: 176

```
Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Ile
            20                  25                  30

Gln Pro Gly Gly Ser Leu Arg Leu Ser Cys Ala Ala Ser Gly Phe Thr
        35                  40                  45

Val Ser Arg Ile Tyr Met Ser Trp Val Arg Gln Ala Pro Gly Lys Gly
    50                  55                  60

Leu Glu Trp Val Ser Val Ile Tyr Ser Gly Gly Ser Ile Tyr Tyr Ala
65                  70                  75                  80

Asp Ser Val Lys Gly Arg Phe Thr Ile Ser Arg Asp Ser Ser Lys Asn
                85                  90                  95

Thr Val Tyr Leu Gln Met Asn Ser Leu Arg Ala Glu Asp Thr Ala Val
            100                 105                 110

Tyr Tyr Cys Ala Arg Ala Val Pro Ser Ala Pro Ser Ser Phe Asp Ile
        115                 120                 125

Trp Gly Gln Gly Thr Met Val Thr Val Ser Ser Glu Pro Lys Ser Cys
    130                 135                 140

Asp Lys Thr His Thr Cys Pro Pro Cys Pro Ala Pro Glu Leu Leu Gly
145                 150                 155                 160

Gly Pro Asp Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
        195                 200                 205

His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
```

```
                225                 230                 235                 240
Lys Glu Tyr Lys Cys Lys Val Ser Asn Lys Ala Leu Pro Ala Pro Glu
                245                 250                 255

Glu Lys Thr Ile Ser Lys Ala Lys Gly Gln Pro Arg Glu Pro Gln Val
                260                 265                 270

Tyr Thr Leu Pro Pro Ser Arg Glu Glu Met Thr Lys Asn Gln Val Ser
                275                 280                 285

Leu Thr Cys Leu Val Lys Gly Phe Tyr Pro Ser Asp Ile Ala Val Glu
                290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
                340                 345                 350

His Glu Ala Leu His Asn His Tyr Thr Gln Lys Ser Leu Ser Leu Ser
                355                 360                 365

Pro Gly Lys
        370

<210> SEQ ID NO 177
<211> LENGTH: 119
<212> TYPE: PRT
<213> ORGANISM: Homo Sapiens

<400> SEQUENCE: 177

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Arg Ile
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Ile Tyr Tyr Ala Asp Ser Val Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ala Val Pro Ser Ala Pro Ser Ser Phe Asp Ile Trp Gly Gln Gly
                100                 105                 110

Thr Met Val Thr Val Ser Ser
        115

<210> SEQ ID NO 178
<211> LENGTH: 10
<212> TYPE: PRT
<213> ORGANISM: Homo Sapiens

<400> SEQUENCE: 178

Gly Phe Thr Val Ser Arg Ile Tyr Met Ser
1               5                   10

<210> SEQ ID NO 179
<211> LENGTH: 16
<212> TYPE: PRT
<213> ORGANISM: Homo Sapiens

<400> SEQUENCE: 179
```

Val Ile Tyr Ser Gly Gly Ser Ile Tyr Tyr Ala Asp Ser Val Lys Gly
1               5                   10                  15

<210> SEQ ID NO 180
<211> LENGTH: 11
<212> TYPE: PRT
<213> ORGANISM: Homo Sapiens

<400> SEQUENCE: 180

Ala Val Pro Ser Ala Pro Ser Ser Phe Asp Ile
1               5                   10

<210> SEQ ID NO 181
<211> LENGTH: 1113
<212> TYPE: DNA
<213> ORGANISM: Homo Sapiens

<400> SEQUENCE: 181

| | |
|---|---|
| atggagaccg acaccctgct gctgtgggtg ctgctgctgt gggtgcccgg atccaccggc | 60 |
| gaggtgcagc tggtggagag cggaggaggc ttgatccagc ctgggggtc cctgagactc | 120 |
| tcctgtgcag tctctgggtt caccgtcagt aagaattaca tgagctgggt ccgccaggcc | 180 |
| ccagggaagg gctggagtg gtcagcgtt gtttatagcg gtggtagcaa aacctacgca | 240 |
| gactccgtga aggccgatt caccatctcc agagacaatt ccaagaacac actgtatctt | 300 |
| caaatgaaca gcctgagagc cgaggacacg gccgtgtatt actgtgcgag agccgttcct | 360 |
| cattccccca gttcttttga tatctggggc caagggacaa tggtcaccgt ctcttcagag | 420 |
| cccaaatctt gtgacaaaac tcacacatgc ccaccgtgcc cagcacctga actcctgggg | 480 |
| ggaccggacg tcttcctctt ccccccaaaa cccaaggaca cccctcatga tctcccggac c| 540 |
| cctgaggtca catgcgtggt ggtggacgtg agccacgaag accctgaggt caagttcaac | 600 |
| tggtacgtgg acggcgtgga ggtgcataat gccaagacaa agccgcggga ggagcagtac | 660 |
| aacagcacgt accgggtggt cagcgtcctc accgtcctgc accaggactg gctgaatggc | 720 |
| aaggagtaca agtgcaaggt ctccaacaaa gccctcccag cccccgagga aaaaccatc | 780 |
| tccaaagcca agggcagcc ccgagaacca caggtgtaca ccctgccccc atcccgggag | 840 |
| gagatgacca gaaccaggt cagcctgacc tgcctggtca aaggcttcta tcccagcgac | 900 |
| atcgccgtgg agtgggagag caatgggcag ccggagaaca actacaagac cacgcctccc | 960 |
| gtgctggact ccgacggctc cttcttcctc tacagcaagc tcaccgtgga caagagcagg | 1020 |
| tggcagcagg ggaacgtctt ctcatgctcc gtgatgcatg aggctctgca caaccactac | 1080 |
| acgcagaaga gcctctccct gtctccgggt aaa | 1113 |

<210> SEQ ID NO 182
<211> LENGTH: 371
<212> TYPE: PRT
<213> ORGANISM: Homo Sapiens

<400> SEQUENCE: 182

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Ile
                20                  25                  30

Gln Pro Gly Gly Ser Leu Arg Leu Ser Cys Ala Val Ser Gly Phe Thr
            35                  40                  45

Val Ser Lys Asn Tyr Met Ser Trp Val Arg Gln Ala Pro Gly Lys Gly

```
            50                  55                  60
Leu Glu Trp Val Ser Val Val Tyr Ser Gly Gly Ser Lys Thr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Ala Val Pro His Ser Pro Ser Ser Phe Asp Ile
        115                 120                 125

Trp Gly Gln Gly Thr Met Val Thr Val Ser Ser Glu Pro Lys Ser Cys
    130                 135                 140

Asp Lys Thr His Thr Cys Pro Pro Cys Pro Ala Pro Glu Leu Leu Gly
145                 150                 155                 160

Gly Pro Asp Val Phe Leu Phe Pro Pro Lys Pro Lys Asp Thr Leu Met
                165                 170                 175

Ile Ser Arg Thr Pro Glu Val Thr Cys Val Val Val Asp Val Ser His
            180                 185                 190

Glu Asp Pro Glu Val Lys Phe Asn Trp Tyr Val Asp Gly Val Glu Val
        195                 200                 205

His Asn Ala Lys Thr Lys Pro Arg Glu Glu Gln Tyr Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Ala Leu Pro Ala Pro Glu
                245                 250                 255

Glu Lys Thr Ile Ser Lys Ala Lys Gly Gln Pro Arg Glu Pro Gln Val
            260                 265                 270

Tyr Thr Leu Pro Pro Ser Arg Glu Glu Met Thr Lys Asn Gln Val Ser
        275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Lys Leu Thr Val
                325                 330                 335

Asp Lys Ser Arg Trp Gln Gln Gly Asn Val Phe Ser Cys Ser Val Met
            340                 345                 350

His Glu Ala Leu His Asn His Tyr Thr Gln Lys Ser Leu Ser Leu Ser
        355                 360                 365

Pro Gly Lys
    370

<210> SEQ ID NO 183
<211> LENGTH: 119
<212> TYPE: PRT
<213> ORGANISM: Homo Sapiens

<400> SEQUENCE: 183

Glu Val Gln Leu Val Glu Ser Gly Gly Gly Leu Ile Gln Pro Gly Gly
  1               5                  10                  15

Ser Leu Arg Leu Ser Cys Ala Val Ser Gly Phe Thr Val Ser Lys Asn
                 20                  25                  30

Tyr Met Ser Trp Val Arg Gln Ala Pro Gly Lys Gly Leu Glu Trp Val
             35                  40                  45
```

Ser Val Val Tyr Ser Gly Gly Ser Lys Thr Tyr Ala Asp Ser Val Lys
            50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ala Val Pro His Ser Pro Ser Ser Phe Asp Ile Trp Gly Gln Gly
            100                 105                 110

Thr Met Val Thr Val Ser Ser
        115

<210> SEQ ID NO 184
<211> LENGTH: 10
<212> TYPE: PRT
<213> ORGANISM: Homo Sapiens

<400> SEQUENCE: 184

Gly Phe Thr Val Ser Lys Asn Tyr Met Ser
1               5                   10

<210> SEQ ID NO 185
<211> LENGTH: 16
<212> TYPE: PRT
<213> ORGANISM: Homo Sapiens

<400> SEQUENCE: 185

Val Val Tyr Ser Gly Gly Ser Lys Thr Tyr Ala Asp Ser Val Lys Gly
1               5                   10                  15

<210> SEQ ID NO 186
<211> LENGTH: 11
<212> TYPE: PRT
<213> ORGANISM: Homo Sapiens

<400> SEQUENCE: 186

Ala Val Pro His Ser Pro Ser Ser Phe Asp Ile
1               5                   10

<210> SEQ ID NO 187
<211> LENGTH: 1116
<212> TYPE: DNA
<213> ORGANISM: Homo Sapiens

<400> SEQUENCE: 187

```
atggagaccg acaccctgct gctgtgggtg ctgctgctgt gggtgcccgg atccaccggc      60
gaggtgcagc tggtggagtc cggggggaggc ttagttcagc ctggggggtc cctgagactc     120
tcctgtgcag cctctggatt caccttcagt aactactgga tgcactgggt ccgccaagct     180
ccagggaagg ggctggtgtg ggtctcacgt attaatagtg atgggagtaa cacaacctac     240
gcggactccg tgaagggccg attcaccatc tccagagaca acgccaagaa cacgctgtat     300
ctgcaaatga acagtctgag agccgaggac acggctgtgt attactgtgc aagatggttc     360
ggggagcact actacggaat ggacgtctgg ggccaaggga ccacggtcac cgtctcttca     420
gagcccaaat cttgtgacaa aactcacaca tgcccaccgt gcccagcacc tgaactcctg     480
gggggaccgg acgtcttcct cttccccccca aaacccaagg acaccctcat gatctcccgg     540
acccctgagg tcacatgcgt ggtggtggac gtgagccacg aagaccctga ggtcaagttc     600
aactggtacg tggacggcgt ggaggtgcat aatgccaaga caaagccgcg ggaggagcag     660
tacaacagca cgtaccgggt ggtcagcgtc ctcaccgtcc tgcaccagga ctggctgaat     720
```

```
ggcaaggagt acaagtgcaa ggtctccaac aaagccctcc cagccccga  ggagaaaacc     780 atctccaaag ccaagggca gccccgagaa ccacaggtgt acaccctgcc cccatcccgg      840
gaggagatga ccaagaacca ggtcagcctg acctgcctgg tcaaaggctt ctatcccagc     900
gacatcgccg tggagtggga gagcaatggg cagccggaga caactacaa gaccacgcct     960 cccgtgctgg actccgacgg ctccttcttc ctctacagca agctcaccgt ggacaagagc    1020
aggtggcagc aggggaacgt cttctcatgc tccgtgatgc atgaggctct gcacaaccac    1080
tacacgcaga agagcctctc cctgtctccg ggtaaa                              1116
```

```
<210> SEQ ID NO 188
<211> LENGTH: 372
<212> TYPE: PRT
<213> ORGANISM: Homo Sapiens

<400> SEQUENCE: 188

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Thr
            35                  40                  45

Phe Ser Asn Tyr Trp Met His Trp Val Arg Gln Ala Pro Gly Lys Gly
        50                  55                  60

Leu Val Trp Val Ser Arg Ile Asn Ser Asp Gly Ser Asn Thr Thr Tyr
65                  70                  75                  80

Ala Asp Ser Val Lys Gly Arg Phe Thr Ile Ser Arg Asp Asn Ala Lys
                85                  90                  95

Asn Thr Leu Tyr Leu Gln Met Asn Ser Leu Arg Ala Glu Asp Thr Ala
            100                 105                 110

Val Tyr Tyr Cys Ala Arg Trp Phe Gly Glu His Tyr Tyr Gly Met Asp
        115                 120                 125

Val Trp Gly Gln Gly Thr Thr Val Thr Val Ser Ser Glu Pro Lys Ser
    130                 135                 140

Cys Asp Lys Thr His Thr Cys Pro Pro Cys Pro Ala Pro Glu Leu Leu
145                 150                 155                 160

Gly Gly Pro Asp Val Phe Leu Phe Pro Pro Lys Pro Lys Asp Thr Leu
                165                 170                 175

Met Ile Ser Arg Thr Pro Glu Val Thr Cys Val Val Val Asp Val Ser
            180                 185                 190

His Glu Asp Pro Glu Val Lys Phe Asn Trp Tyr Val Asp Gly Val Glu
        195                 200                 205

Val His Asn Ala Lys Thr Lys Pro Arg Glu Glu Gln Tyr Asn Ser Thr
    210                 215                 220

Tyr Arg Val Val Ser Val Leu Thr Val Leu His Gln Asp Trp Leu Asn
225                 230                 235                 240

Gly Lys Glu Tyr Lys Cys Lys Val Ser Asn Lys Ala Leu Pro Ala Pro
                245                 250                 255

Glu Glu Lys Thr Ile Ser Lys Ala Lys Gly Gln Pro Arg Glu Pro Gln
            260                 265                 270

Val Tyr Thr Leu Pro Pro Ser Arg Glu Glu Met Thr Lys Asn Gln Val
        275                 280                 285

Ser Leu Thr Cys Leu Val Lys Gly Phe Tyr Pro Ser Asp Ile Ala Val
    290                 295                 300
```

```
Glu Trp Glu Ser Asn Gly Gln Pro Glu Asn Asn Tyr Lys Thr Thr Pro
305                 310                 315                 320

Pro Val Leu Asp Ser Asp Gly Ser Phe Phe Leu Tyr Ser Lys Leu Thr
                325                 330                 335

Val Asp Lys Ser Arg Trp Gln Gln Gly Asn Val Phe Ser Cys Ser Val
            340                 345                 350

Met His Glu Ala Leu His Asn His Tyr Thr Gln Lys Ser Leu Ser Leu
            355                 360                 365

Ser Pro Gly Lys
    370

<210> SEQ ID NO 189
<211> LENGTH: 120
<212> TYPE: PRT
<213> ORGANISM: Homo Sapiens

<400> SEQUENCE: 189

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Asn Thr Thr Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Phe Gly Glu His Tyr Tyr Gly Met Asp Val Trp Gly Gln
            100                 105                 110

Gly Thr Thr Val Thr Val Ser Ser
        115                 120

<210> SEQ ID NO 190
<211> LENGTH: 10
<212> TYPE: PRT
<213> ORGANISM: Homo Sapiens

<400> SEQUENCE: 190

Gly Phe Thr Phe Ser Asn Tyr Trp Met His
1               5                   10

<210> SEQ ID NO 191
<211> LENGTH: 17
<212> TYPE: PRT
<213> ORGANISM: Homo Sapiens

<400> SEQUENCE: 191

Arg Ile Asn Ser Asp Gly Ser Asn Thr Thr Tyr Ala Asp Ser Val Lys
1               5                   10                  15

Gly

<210> SEQ ID NO 192
<211> LENGTH: 11
<212> TYPE: PRT
<213> ORGANISM: Homo Sapiens

<400> SEQUENCE: 192
```

Trp Phe Gly Glu His Tyr Tyr Gly Met Asp Val
1               5                   10

<210> SEQ ID NO 193
<211> LENGTH: 23
<212> TYPE: DNA
<213> ORGANISM: Artificial sequence
<220> FEATURE:
<223> OTHER INFORMATION: Primer

<400> SEQUENCE: 193
gtgtccagtg tgaggtgcag ctg                                          23

<210> SEQ ID NO 194
<211> LENGTH: 23
<212> TYPE: DNA
<213> ORGANISM: Artificial sequence
<220> FEATURE:
<223> OTHER INFORMATION: Primer

<400> SEQUENCE: 194
gtgtccagtg tcaggtgcag ctg                                          23

<210> SEQ ID NO 195
<211> LENGTH: 24
<212> TYPE: DNA
<213> ORGANISM: Artificial sequence
<220> FEATURE:
<223> OTHER INFORMATION: Primer

<400> SEQUENCE: 195
ggcttacaac cacaatccct gggc                                         24

<210> SEQ ID NO 196
<211> LENGTH: 672
<212> TYPE: DNA
<213> ORGANISM: Homo Sapiens

<400> SEQUENCE: 196
atggcttgcc ttggatttca gcggcacaag gctcagctga acctggctac caggacctgg    60
ccctgcactc tcctgttttt tcttctcttc atccctgtct ctgcaaagc aatgcacgtg    120
gcccagcctg ctgtggtact ggccagcagc cgaggcatcg ccagctttgt gtgtgagtat   180
gcatctccag gcaaagccac tgaggtccgg gtgacagtgc ttcggcaggc tgacagccag   240
gtgactgaag tctgtgcggc aacctacatg atggggaatg agttgacctt cctagatgat   300
tccatctgca cgggcaccct cagtggaaat caagtgaacc tcactatcca aggactgagg   360
gccatggaca cgggactcta catctgcaag gtggagctca tgtacccacc gccatactac   420
ctgggcatag caacggaac ccagatttat gtaattgatc cagaaccgtg cccagattct   480
gacttcctcc tctggatcct tgcagcagtt agttcggggt tgttttttta tagctttctc   540
ctcacagctg tttctttgag caaaatgcta aagaaaagaa gccctcttac aacagggtc    600
tatgtgaaaa tgcccccaac agagccagaa tgtgaaaagc aatttcagcc ttattttatt   660
cccatcaatt ga                                                      672

<210> SEQ ID NO 197
<211> LENGTH: 223
<212> TYPE: PRT
<213> ORGANISM: Homo Sapiens

<400> SEQUENCE: 197

```
Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65              70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
                210                 215                 220
```

<210> SEQ ID NO 198
<211> LENGTH: 672
<212> TYPE: DNA
<213> ORGANISM: Macaca mulatta

<400> SEQUENCE: 198

```
atggcttgcc ttggatttca gcggcacaag gctcggctca acctggctac caggacccgg      60
ccctacactc tcctgttttc tcttctcttc atccctgtct tctccaaagc aatgcacgtg     120
gcccagcctg ctgtggtgct ggccaacagc cgagggatcg ccagctttgt gtgtgagtat     180
gcatctccag gcaaagccac tgaggtccgg gtgacagtgc ttcggcaggc cgacagccag     240
gtgactgaag tctgtgcggc aacatacatg atggggaatg agttgacctt cctagatgat     300
tccatctgca cgggcacctc cagtggaaat caagtgaacc tcactatcca aggactgagg     360
gctatggaca caggactcta catctgcaag gtggagctca tgtacccacc accatactac     420
atgggcatag caatggaacc cagatttat gtaattgatc cagaaccgtg cccagattct      480
gacttcctcc tctggatcct tgcagcagtt agttcggggt tgttttttta tagctttctc     540
ctcacagctg tttctttgag caaaatgcta aagaaaagaa gccctctcac aacagggtc     600
tatgtgaaaa tgcccccaac agagccagaa tgtgaaaagc aatttcagcc ttatttatt      660
cccatcaatt ga                                                        672
```

<210> SEQ ID NO 199
<211> LENGTH: 448
<212> TYPE: PRT

<213> ORGANISM: Artificial sequence
<220> FEATURE:
<223> OTHER INFORMATION: heavy chain of Ipilimumab analogue

<400> SEQUENCE: 199

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

```
                385                 390                 395                 400
Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
                    420                 425                 430

Leu His Asn His Tyr Thr Gln Lys Ser Leu Ser Leu Ser Pro Gly Lys
                    435                 440                 445

<210> SEQ ID NO 200
<211> LENGTH: 215
<212> TYPE: PRT
<213> ORGANISM: Artificial sequence
<220> FEATURE:
<223> OTHER INFORMATION: light chain of Ipilimumab analogue

<400> SEQUENCE: 200

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Phe Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215
```

ANTIBODIES BINDING CTLA-4 AND USES THEREOF

RELATED APPLICATIONS

The present application is a divisional of, and claims the benefit of and priority to, U.S. patent application Ser. No. 16/224,825, filed Dec. 19, 2018, which claims the benefit of and priority to, U.S. Provisional Application No. 62/607,917, filed Dec. 20, 2017, both of which are hereby incorporated by reference for all purposes.

FIELD OF THE INVENTION

The invention relates to monoclonal anti-CTLA-4 antibodies, nucleic acids encoding the antibodies, expression vectors and recombinant cells containing the nucleic acids, and pharmaceutical compositions comprising the antibodies. Methods of making the antibodies, and methods of using the antibodies to treat diseases including cancers and autoimmune diseases are also provided.

SEQUENCE LISTING

The instant application contains a Sequence Listing which has been submitted electronically and is hereby incorporated by reference in its entirety. Said ASCII copy was created on Jul. 13, 2021, is named "20210713_112171-0039_Parent-SeqListing.TXT", and is 216,062 bytes in size.

BACKGROUND OF THE INVENTION

Cancer immunotherapy, a recent breakthrough in cancer treatment, employs a patient's own immune system to attack tumor cells. Promoting a robust CD8 T cell dependent cytotoxic response in the tumor microenvironment is important for the generation of an effective antitumor immune response. However, tumor tends to evade the immune surveillance by taking advantage of the T cell suppression machinery. The exhaustion of tumor-infiltrating lymphocytes (TIL) results in the anergy of cytotoxic T cells and escape of tumor cells (Wherry and Kurachi, 2015, *Nat Rev Immunol.*, 2015, 15: 486-499; Dyck and Mills, 2017, *Eur. J. Immunol.*, 47(5): 765-779).

Inhibitors of immune checkpoint proteins have the potential to treat a variety of tumors, such as metastatic melanoma, lung cancer, breast cancer, and renal cell carcinoma. CTLA-4 (CD152) is such an inhibitory checkpoint molecule on the surface of T cells. It was originally identified by differential screening of a murine cytolytic T cell cDNA library (Brunet et al., 1987, *Nature*, 328:267-270). It is suggested that CTLA-4 can function as a negative regulator of T cell activation (Walunas et al., 1994, *Immunity*, 1:405-413). CTLA-4 is expressed constitutively on the surfaces of regulatory T cells, but the amount is relatively low. It is upregulated upon T cell activation. Upon activation, CTLA-4 interacts with CD80 (B7.1) and CD86 (B7.2) which are also the ligands for CD28, with a much higher binding affinity than CD28 (van der Merwe et al., 1997, *J Exp Med.* 185:393-403; Alegre et al., 2001, *Nat Rev Immunol*, 1: 220-228). CD28 signaling promotes T cell activation, while the interaction of CTLA-4 with its ligands B7.1 and B7.2 prevents further activation of T cells.

CTLA-4 antagonists are attractive since the blockade of CTLA-4 with the antagonists was shown as an efficient therapy against tumors (U.S. Pat. No. 6,984,720). Inhibition of this surface receptor using an antagonist such as an anti CTLA-4 mAb augmented effector CD4 and CD8 T-cell responses and reduced the suppressive function of Treg cells. The CTLA-4 antagonist based treatments progressed fast in recent years. Ipilimumab (YERVOY®), is a humanized antibody and blocks the effects of CTLA-4, which augments T-cell responses to tumor cells. Ipilimumab was the first medicament to show an improvement in overall survival of patients with metastatic melanoma in a randomized, controlled phase 3 trial. It has a manageable safety profile at a dosage of 3 mg/kg as a monotherapy in patients previously treated with other therapies and at a dosage of 10 mg/kg in combination with dacarbazine in treatment-naive patients. In addition to malignant melanoma, Ipilimumab is also under development for prostate cancer and non-small cell lung cancer treatment.

However, despite the progresses mentioned above, CTLA-4 antagonists with improved affinity, specificity and developability are desired. Further, more effective therapeutics involving anti-CTLA-4 antibodies that effectively inhibit the CTLA-4 signaling activity while causing minimal adverse side effects in humans are also needed.

SUMMARY OF THE INVENTION

Disclosed is an isolated monoclonal antibody, comprising a CD152-binding domain, wherein the CD152-binding domain comprises an immunoglobulin heavy chain variable region comprising CDR1, CDR2, and CDR3, wherein the CDR1, CDR2, and CDR3 comprise amino acid sequences having at least 80%, 85%, 88%, 90%, 92%, 95%, 97%, 98%, 99%, or 100% identity to (1) SEQ ID NOs: 4, 5 and 6, respectively; (2) SEQ ID NOs: 10, 11 and 12, respectively; (3) SEQ ID NOs: 16, 17 and 18, respectively; (4) SEQ ID NOs: 22, 23 and 24, respectively; (5) SEQ ID NOs: 28, 29 and 30, respectively; (6) SEQ ID NOs: 34, 35 and 36, respectively; (7) SEQ ID NOs: 40, 41 and 42, respectively; (8) SEQ ID NOs: 46, 47 and 48, respectively; (9) SEQ ID NOs: 52, 53 and 54, respectively; (10) SEQ ID NOs: 58, 59 and 60, respectively; (11) SEQ ID NOs: 64, 65 and 66, respectively; (12) SEQ ID NOs: 70, 71 and 72, respectively; (13) SEQ ID NOs: 76, 77 and 78, respectively; (14) SEQ ID NOs: 82, 83 and 84, respectively; (15) SEQ ID NOs: 88, 89 and 90, respectively; (16) SEQ ID NOs: 94, 95 and 96, respectively; (17) SEQ ID NOs: 100, 101 and 102, respectively; (18) SEQ ID NOs: 106, 107 and 108, respectively; (19) SEQ ID NOs: 112, 113 and 114, respectively; (20) SEQ ID NOs: 118, 119 and 120, respectively; (21) SEQ ID NOs: 124, 125 and 126, respectively; (22) SEQ ID NOs: 130, 131 and 132, respectively; (23) SEQ ID NOs: 136, 137 and 138, respectively; (24) SEQ ID NOs: 142, 143 and 144, respectively; (25) SEQ ID NOs: 148, 149 and 150, respectively; (26) SEQ ID NOs: 154, 155 and 156, respectively; (27) SEQ ID NOs: 160, 161 and 162, respectively; (28) SEQ ID NOs: 166, 167 and 168, respectively; (29) SEQ ID NOs: 172, 173 and 174, respectively; (30) SEQ ID NOs: 178, 179 and 180, respectively; (31) SEQ ID NOs: 184, 185 and 186, respectively; or (32) SEQ ID NOs: 190, 191 and 192, respectively.

In some cases, the antibody is a heavy-chain-only antibody. In some cases, the antibody does not comprise an immunoglobulin light chain. In some cases, the antibody comprises one immunoglobulin heavy chain. In some cases, the antibody comprises two immunoglobulin heavy chains. In some cases, the antibody consists of two immunoglobulin heavy chains. In some cases, at least one of the two immunoglobulin heavy chains comprises an amino acid sequence having at least 80%, 85%, 88%, 90%, 92%, 95%, 97%, 98%, 99%, or 100% identity to SEQ ID NOs: 2, 8, 14, 20, 26, 32, 38, 44, 50, 56, 62, 68, 74, 80, 86, 92, 98, 104, 110, 116, 122, 128, 134, 140, 146, 152, 158, 164, 170, 176, 182, or 188.

In some cases, the immunoglobulin heavy chain variable region comprises an amino acid sequence having at least 80%, 85%, 88%, 90%, 92%, 95%, 97%, 98%, 99%, or 100% identity to SEQ ID NOs: 3, 9, 15, 21, 27, 33, 39, 45, 51, 57, 63, 69, 75, 81, 87, 93, 99, 105, 111, 117, 123, 129, 135, 141, 147, 153, 159, 165, 171, 177, 183, or 189.

In some cases, the antibody binds specifically to human CD152. In some cases, the antibody binds to human CD152 with high affinity. In some cases, the antibody binds to human CD152 with an affinity higher than an ipilimumab analogue. In some cases, the antibody binds to human CD152 with the affinity that is at least 2-fold, at least 5-fold, at least 10-fold, at least 20-fold, at least 30-fold, at least 50-fold, or at least 100-fold higher than an ipilimumab analogue.

In some cases, the antibody dissociates from human CD152 with a $K_d$ of $1.0*10^{-7}$ M or less. In some cases, the antibody dissociates from human CD152 with a $K_d$ of $1.0*10^{-8}$ M or less. In some cases, the antibody dissociates from human CD152 with a $K_d$ of $1.0*10^{-9}$ M or less. In some cases, the antibody dissociates from human CD152 with a $K_d$ of $1.0*10^{-10}$ M or less. In some cases, the antibody dissociates from human CD152 with a $K_d$ of $1.0*10^{-11}$ M or less. In some cases, the $K_d$ is $6.0*10^{-11}$ M or less. In some cases, the antibody dissociates from human CD152 with the $K_d$ that is lower than an ipilimumab analogue. In some cases, the antibody dissociates from human CD152 with the $K_d$ that is at least 2-fold, at least 5-fold, at least 10-fold, at least 20-fold, at least 30-fold, at least 50-fold, or at least 100-fold lower than an ipilimumab analogue. In some cases, the $K_d$ is determined by surface plasmon resonance.

In some cases, the antibody binds specifically to monkey CD152. In some cases, the antibody does not bind specifically to monkey CD152. In some cases, the antibody blocks the binding of CD152 to CD80, CD86, or both. In some cases, the antibody promotes secretion of IL-2 by immune cells. In some cases, the antibody induces T-cell activation. In some cases, the antibody stimulates an anti-tumor immune response by immune cells. In some cases, the antibody is a human, humanized, or chimeric antibody.

In another aspect, disclosed herein is an isolated monoclonal heavy-chain-only antibody, comprising a CD152-binding domain, wherein the antibody binds specifically to human CD152. In some cases, the antibody does not comprise an immunoglobulin light chain. In some cases, the antibody comprises one immunoglobulin heavy chain. In some cases, the antibody comprises two immunoglobulin heavy chains. In some cases, the antibody consists of two immunoglobulin heavy chains.

In some cases, the antibody binds to human CD152 with high affinity. In some cases, the antibody binds to human CD152 with an affinity higher than an ipilimumab analogue. In some cases, the antibody binds to human CD152 with the affinity that is at least 2-fold, at least 5-fold, at least 10-fold, at least 20-fold, at least 30-fold, at least 50-fold, or at least 100-fold higher than an ipilimumab analogue.

In some cases, the antibody dissociates from human CD152 with a $K_d$ of $1.0*10^{-7}$ M or less. In some cases, the antibody dissociates from human CD152 with a $K_d$ of $1.0*10^{-8}$ M or less. In some cases, the antibody dissociates from human CD152 with a $K_d$ of $1.0*10^{-9}$ M or less. In some cases, the antibody dissociates from human CD152 with a $K_d$ of $1.0*10^{-10}$ M or less. In some cases, the antibody dissociates from human CD152 with a $K_d$ of $1.0*10^{-11}$ M or less. In some cases, the $K_d$ is $6.0*10^{-11}$ M or less. In some cases, the antibody dissociates from human CD152 with the $K_d$ that is lower than an ipilimumab analogue. In some cases, the antibody dissociates from human CD152 with the $K_d$ that is at least 2-fold, at least 5-fold, at least 10-fold, at least 20-fold, at least 30-fold, at least 50-fold, or at least 100-fold lower than an ipilimumab analogue. In some cases, the $K_d$ is determined by surface plasmon resonance.

In some cases, the antibody binds specifically to monkey CD152. In some cases, the antibody does not bind specifically to monkey CD152. In some cases, the CD152-binding domain comprises an immunoglobulin heavy chain variable region comprising CDR1, CDR2, and CDR3, wherein the CDR1, CDR2, and CDR3 comprise amino acid sequences having at least 80%, 85%, 88%, 90%, 92%, 95%, 97%, 98%, 99%, or 100% identity to (1) SEQ ID NOs: 4, 5 and 6, respectively; (2) SEQ ID NOs: 10, 11 and 12, respectively; (3) SEQ ID NOs: 16, 17 and 18, respectively; (4) SEQ ID NOs: 22, 23 and 24, respectively; (5) SEQ ID NOs: 28, 29 and 30, respectively; (6) SEQ ID NOs: 34, 35 and 36, respectively; (7) SEQ ID NOs: 40, 41 and 42, respectively; (8) SEQ ID NOs: 46, 47 and 48, respectively; (9) SEQ ID NOs: 52, 53 and 54, respectively; (10) SEQ ID NOs: 58, 59 and 60, respectively; (11) SEQ ID NOs: 64, 65 and 66, respectively; (12) SEQ ID NOs: 70, 71 and 72, respectively; (13) SEQ ID NOs: 76, 77 and 78, respectively; (14) SEQ ID NOs: 82, 83 and 84, respectively; (15) SEQ ID NOs: 88, 89 and 90, respectively; (16) SEQ ID NOs: 94, 95 and 96, respectively; (17) SEQ ID NOs: 100, 101 and 102, respectively; (18) SEQ ID NOs: 106, 107 and 108, respectively; (19) SEQ ID NOs: 112, 113 and 114, respectively; (20) SEQ ID NOs: 118, 119 and 120, respectively; (21) SEQ ID NOs: 124, 125 and 126, respectively; (22) SEQ ID NOs: 130, 131 and 132, respectively; (23) SEQ ID NOs: 136, 137 and 138, respectively; (24) SEQ ID NOs: 142, 143 and 144, respectively; (25) SEQ ID NOs: 148, 149 and 150, respectively; (26) SEQ ID NOs: 154, 155 and 156, respectively; (27) SEQ ID NOs: 160, 161 and 162, respectively; (28) SEQ ID NOs: 166, 167 and 168, respectively; (29) SEQ ID NOs: 172, 173 and 174, respectively; (30) SEQ ID NOs: 178, 179 and 180, respectively; (31) SEQ ID NOs: 184, 185 and 186, respectively; or (32) SEQ ID NOs: 190, 191 and 192, respectively.

In some cases, the CD152-binding domain comprises at least one immunoglobulin heavy chain, wherein the immunoglobulin heavy chain comprises an amino acid sequence having at least 80%, 85%, 88%, 90%, 92%, 95%, 97%, 98%, 99%, or 100% identity to SEQ ID NOs: 2, 8, 14, 20, 26, 32, 38, 44, 50, 56, 62, 68, 74, 80, 86, 92, 98, 104, 110, 116, 122, 128, 134, 140, 146, 152, 158, 164, 170, 176, 182, or 188. In some cases, the immunoglobulin heavy chain variable region comprises an amino acid sequence having at least 80%, 85%, 88%, 90%, 92%, 95%, 97%, 98%, 99%, or 100% identity to SEQ ID NOs: 3, 9, 15, 21, 27, 33, 39, 45, 51, 57, 63, 69, 75, 81, 87, 93, 99, 105, 111, 117, 123, 129, 135, 141, 147, 153, 159, 165, 171, 177, 183, or 189.

In some cases, the antibody blocks the binding of CD152 to CD80, CD86, or both. In some cases, the antibody promotes secretion of IL-2 by immune cells. In some cases, the antibody induces T-cell activation. In some cases, the antibody stimulates an anti-tumor immune response by immune cells. In some cases, the antibody is a human, humanized, or chimeric antibody.

In another aspect, disclosed herein is a pharmaceutical composition, comprising any antibody disclosed herein, and a pharmaceutically acceptable excipient thereof. In some cases, the pharmaceutically acceptable excipient is selected from the group consisting of carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. In some cases, the pharmaceutical composition further comprises a second antibody, wherein the second antibody is an immunostimulatory antibody or costimulatory antibody. In some cases, the immunostimulatory antibody is selected from the group consisting of an anti-PD-1 antibody, an anti-PD-L1 antibody, an anti-LAG-3 antibody, an anti-TIM 3 antibody, an anti-STAT3 antibody, and an anti-ROR1 antibody. In some cases, the costimulatory antibody is an anti-CD137 antibody or an anti-GITR antibody.

In another aspect, disclosed herein is an isolated nucleic acid molecule encoding any antibody disclosed herein. In some cases, the nucleic acid molecule comprises a nucleotide sequence having at least 80%, 85%, 88%, 90%, 92%, 95%, 97%, 98%, 99%, or 100% identity to SEQ ID NO: 1, 7, 13, 19, 25, 31, 37, 43, 49, 55, 61, 67, 73, 79, 85, 91, 97, 103, 109, 115, 121, 127, 133, 139, 145, 151, 163, 169, 175, 181, or 187. In some cases, the nucleic acid molecule comprises the nucleotide sequence set forth in SEQ ID NO: 1, 7, 13, 19, 25, 31, 37, 43, 49, 55, 61, 67, 73, 79, 85, 91, 97, 103, 109, 115, 121, 127, 133, 139, 145, 151, 163, 169, 175, 181, or 187.

In another aspect, disclosed herein is an expression vector comprising a nucleic acid segment encoding any antibody disclosed herein, wherein the nucleic acid segment is operatively linked to regulatory sequences suitable for expression of the nucleic acid segment in a host cell. In some cases, the nucleic acid segment comprises a nucleotide sequence having at least 80%, 85%, 88%, 90%, 92%, 95%, 97%, 98%, 99%, or 100% identity to SEQ ID NO: 1, 7, 13, 19, 25, 31, 37, 43, 49, 55, 61, 67, 73, 79, 85, 91, 97, 103, 109, 115, 121, 127, 133, 139, 145, 151, 163, 169, 175, 181, or 187. In some cases, the nucleic acid segment comprises the nucleotide sequence set forth in SEQ ID NO: 1, 7, 13, 19, 25, 31, 37, 43, 49, 55, 61, 67, 73, 79, 85, 91, 97, 103, 109, 115, 121, 127, 133, 139, 145, 151, 163, 169, 175, 181, or 187.

In another aspect, disclosed herein is a host cell comprising any expression vector disclosed herein.

In another aspect, disclosed herein is a method for producing an CD152-binding monoclonal antibody, the method comprising: culturing a host cell comprising any expression vector under conditions whereby the nucleic acid segment is expressed, thereby producing the CD152-binding monoclonal antibody. In some cases, the host cell is a CHO, HEK293, or COS host cell line. In some cases, the CHO host cell line is CHO-K1 cell line. In some cases, the method further comprises recovering the CD152-binding monoclonal antibody.

In another aspect, disclosed herein is a method of inducing an antibody-dependent cell-mediated cytotoxicity (ADCC) against a cell expressing a tumor associated antigen, the method comprising: contacting a T-cell with any antibody disclosed herein, wherein said contacting is under conditions whereby the ADCC against the cell expressing the tumor associated antigen is induced.

In another aspect, disclosed herein is a method for treating a disorder in a subject, the method comprising administering to the subject a therapeutically effective amount of any antibody disclosed herein or any pharmaceutical composition disclosed herein. In some cases, the disorder is a cancer. In some cases, the cancer is selected from the group consisting of leukemia, lymphoma, CLL, small lymphocytic lymphoma, marginal cell B-Cell lymphoma, Burkett's Lymphoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, and head and neck cancer. In some cases, the method further comprises a therapeutic agent. In some cases, the therapeutic agent is an anti-cancer drug. In some cases, the therapeutic agent is ipilimumab, or an biosimilar product thereof. In some cases, the disorder is an autoimmune disease.

In another aspect, disclosed herein is use of any pharmaceutical composition disclosed herein in preparation of a medicament for treating a disorder. In some cases, the disorder is a cancer. In some cases, the cancer is selected from the group consisting of leukemia, lymphoma, CLL, small lymphocytic lymphoma, marginal cell B-Cell lymphoma, Burkett's Lymphoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, and head and neck cancer. In some cases, the disorder is an autoimmune disease.

In another aspect, the invention pertains to an isolated monoclonal antibody, or an antigen-binding portion thereof, having a heavy chain variable region that comprises a CDR1 region, a CDR2 region and a CDR3 region, wherein the CDR1 region, the CDR2 region and the CDR3 region comprise amino acid sequences having at least 80%, 85%, 90%, 95%, 98%, 99% or 100% identity to (1) SEQ ID NOs: 4, 5 and 6, respectively; (2) SEQ ID NOs: 10, 11 and 12, respectively; (3) SEQ ID NOs: 16, 17 and 18, respectively; (4) SEQ ID NOs: 22, 23 and 24, respectively; (5) SEQ ID NOs: 28, 29 and 30, respectively; (6) SEQ ID NOs: 34, 35 and 36, respectively; (7) SEQ ID NOs: 40, 41 and 42, respectively; (8) SEQ ID NOs: 46, 47 and 48, respectively; (9) SEQ ID NOs: 52, 53 and 54, respectively; (10) SEQ ID NOs: 58, 59 and 60, respectively; (11) SEQ ID NOs: 64, 65 and 66, respectively; (12) SEQ ID NOs: 70, 71 and 72, respectively; (13) SEQ ID NOs: 76, 77 and 78, respectively; (14) SEQ ID NOs: 82, 83 and 84, respectively; (15) SEQ ID NOs: 88, 89 and 90, respectively; (16) SEQ ID NOs: 94, 95 and 96, respectively; (17) SEQ ID NOs: 100, 101 and 102, respectively; (18) SEQ ID NOs: 106, 107 and 108, respectively; (19) SEQ ID NOs: 112, 113 and 114, respectively; (20) SEQ ID NOs: 118, 119 and 120, respectively; (21) SEQ ID NOs: 124, 125 and 126, respectively; (22) SEQ ID NOs: 130, 131 and 132, respectively; (23) SEQ ID NOs: 136, 137 and 138, respectively; (24) SEQ ID NOs: 142, 143 and 144, respectively; (25) SEQ ID NOs: 148, 149 and 150, respectively; (26) SEQ ID NOs: 154, 155 and 156, respectively; (27) SEQ ID NOs: 160, 161 and 162, respectively; (28) SEQ ID NOs: 166, 167 and 168, respectively; (29) SEQ ID NOs: 172, 173 and 174, respectively; (30) SEQ ID NOs: 178, 179 and 180, respectively; (31) SEQ ID NOs: 184, 185 and 186, respectively; or (32) SEQ ID NOs: 190, 191 and 192, respectively; wherein the antibody or antigen-binding fragment thereof binds CTLA-4.

In another aspect, an isolated monoclonal antibody, or an antigen-binding portion thereof, of the present invention comprises a heavy chain variable region comprising the amino acid sequence having at least 80%, 85%, 90%, 95%, 98%, 99% or 100% identity to SEQ ID NOs: 3, 9, 15, 21, 27, 33, 39, 45, 51, 57, 63, 69, 75, 81, 87, 93, 99, 105, 111, 117, 123, 129, 135, 141, 147, 153, 159, 165, 171, 177, 183 or 189.

In one embodiment, the antibody of the present invention comprises a heavy chain comprising the amino acid sequence having at least 80%, 85%, 90%, 95%, 98%, 99% or 100% identity to SEQ ID NOs:2, 8, 14, 20, 26, 32, 38, 44, 50, 56, 62, 68, 74, 80, 86, 92, 98, 104, 110, 116, 122, 128, 134, 140, 146, 152, 158, 164, 170, 176, 182 or 188, which may be encoded by the nucleic acid sequence having at least 80%, 85%, 90%, 95%, 98%, 99% or 100% identity to SEQ ID No: 1, 7, 13, 19, 25, 31, 37, 43, 49, 55, 61, 67, 73, 79, 85, 91, 97, 103, 109, 115, 121, 127, 133, 139, 145, 151, 157, 163, 169, 175, 181 or 187.

In some embodiments, the antibody of the present invention consists substantially of or consists of two heavy chains described above.

In another aspect of the invention, the antibody or an antigen-binding portion thereof is part of an immunoconjugate which comprises a therapeutic agent, e.g., a cytotoxin or a radioactive isotope, linked to the antibody. In another aspect, the antibody is part of a bispecific molecule which comprises a second functional moiety (e.g., a second antibody) having a different binding specificity from said antibody, or the antigen binding portion thereof. In another aspect, the antibody or an antigen binding portions thereof of the present invention can be made into part of a chimeric antigen receptor (CAR) or an engineered T cell receptor. The antibody or an antigen binding portions thereof of the present invention can also be encoded by or used in conjunction with an oncolytic virus.

A pharmaceutical composition comprising an antibody, or an antigen-binding portion thereof, an immunoconjugate, a bispecific molecule, a chimeric antigen receptor, an engineered T cell receptor, or an oncolytic virus of the invention, optionally formulated in a pharmaceutically acceptable carrier, is also provided.

The pharmaceutical composition may further comprise other anticancer agents. The pharmaceutical composition may further comprise at least one additional immunostimulatory antibody selected from the group consisting of an anti-PD-1 antibody, an anti-PD-L1 antibody, an anti-LAG-3 antibody, an anti-TIM 3 antibody, an anti-STAT3 antibody, and an anti-ROR1 antibody, and/or an costimulatory antibody which can be an anti-CD137 antibody or an anti-GITR antibody.

A nucleic acid molecule encoding the antibody, or the antigen-binding portion (e.g., variable regions and/or CDRs) thereof, of the invention is also provided, as well as an expression vector comprising the nucleic acid and a host cell comprising the expression vector. A method for preparing an anti-CTLA-4 antibody using the host cell comprising the expression vector is also provided, and comprises steps of (i) expressing the antibody in the host cell and (ii) isolating the antibody from the host cell.

In yet another embodiment, the invention provides a method for inhibiting growth of tumor cells in a subject, comprising administering to the subject an therapeutically effective amount of an antibody, or an antigen-binding portion thereof, of the invention. The tumor may be a solid or non-solid tumor, selected form the group consisting of leukemia, lymphoma, CLL, small lymphocytic lymphoma, marginal cell B-Cell lymphoma, Burkett's Lymphoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, and head and neck cancer. Preferably, the tumor is melanoma, prostate cancer or non-small cell lung cancer. In yet another embodiment, the invention provides a method for treating autoimmune disease in a subject, comprising administering to the subject an therapeutically effective amount of an antibody, or an antigen-binding portion thereof, of the invention. In still another embodiment, the invention provides a method for treating viral infection in a subject, comprising administering to the subject an therapeutically effective amount of an antibody, or an antigen-binding portion thereof, of the invention. In another embodiment, the method comprises administering a pharmaceutical composition, a bispecific, or an immunoconjugate of the invention.

In another aspect, the invention provides an anti-CTLA-4 antibody and a composition of the invention for use in the foregoing methods, or for the manufacture of a medicament for use in the foregoing methods (e.g., for treatment).

Other features and advantages of the instant disclosure will be apparent from the following detailed description and examples, which should not be construed as limiting. The contents of all references, Genbank entries, patents and published patent applications cited throughout this application are expressly incorporated herein by reference.

BRIEF DESCRIPTION OF THE DRAWINGS

The foregoing summary, as well as the following detailed description of the invention, will be better understood when construed in conjunction with the drawings. It should be understood that the invention is not limited to the embodiments as shown in the drawings.

In the drawings.

DETAILED DESCRIPTION OF THE INVENTION

General Overview

Figure 1:
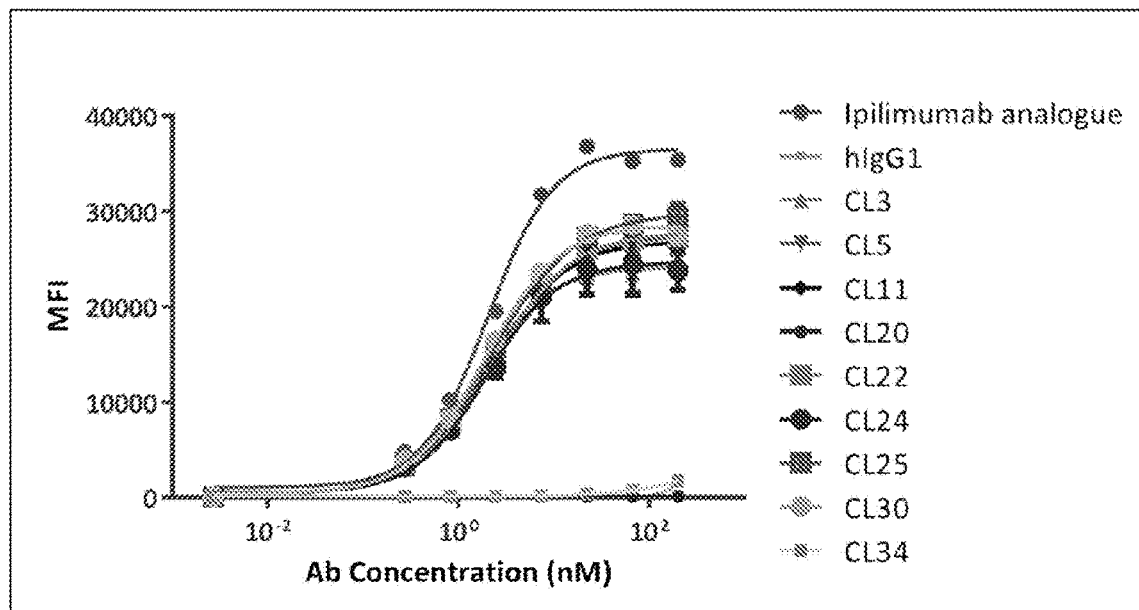
FIG. 1 shows the binding activity of the anti-CTLA-4 antibodies of the present invention to human CTLA-4 expressed on 293 cells.

The disclosure provides antibodies that specifically bind to CD152. These binding molecules may bind specifically to CD152 and to another target. Administration of a therapeutically effective amount of a CD152-binding antibody to a patient in need thereof is useful for treatment of certain disorders, including certain cancers. The binding of the antibody to a T-cell expressing CD152 induces an antibody-dependent cell-mediated cytotoxicity against a cell expressing a tumor associated antigen. The CD152-binding therapeutics of the disclosure offer various advantages in treating patients, for example, effective binding to CD152, efficient induction of the antibody-dependent cell-mediated cytotoxicity and/or a lower risk of adverse events (e.g., toxicity). In certain aspects, the CD152-binding antibodies bind to CD152 more effectively in certain formats (e.g., heavy-chain-only antibody compared to typical full-length antibody), leading to higher potency and improved utility in treating disorders associated with CD152.

Definitions

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously. In addition, it should be understood that the polypeptides comprising the various combinations of the components (e.g., domains or regions) and substituents described herein, are disclosed by the present application to the same extent as if each polypeptide was set forth individually. Thus, selection of particular components of individual polypeptides is within the scope of the present disclosure.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

As used herein, a "polypeptide" or "polypeptide chain" is a single, linear and contiguous arrangement of covalently linked amino acids. It does not include two polypeptide chains that link together in a non-linear fashion, such as via an interchain disulfide bond (e.g., a half immunoglobulin molecule in which a light chain links with a heavy chain via a disulfide bond). Polypeptides can have or form one or more intrachain disulfide bonds. With regard to polypeptides as described herein, reference to amino acid residues corresponding to those specified by SEQ ID NO includes post-translational modifications of such residues.

A "protein" is a macromolecule comprising one or more polypeptide chains. A protein can also comprise non-peptidic components, such as carbohydrate groups. Carbohydrates and other non-peptidic substituents can be added to a protein by the cell in which the protein is produced, and will vary with the type of cell. Proteins are defined herein in terms of their amino acid backbone structures; substituents such as carbohydrate groups are generally not specified, but may be present nonetheless.

The term "antibody", "immunoglobulin" or "Ig" may be used interchangeably herein and means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and F fragments), single chain F (scFv) mutants, multispecific antibodies such as bispecific antibodies (including dual binding antibodies), chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. The term "antibody" can also refer to a Y-shaped glycoprotein with a molecular weight of approximately 150 kDa that is made up of four polypeptide chains: two light (L) chains and two heavy (H) chains. There are five types of mammalian Ig heavy chain isotypes denoted by the Greek letters alpha (α), delta (δ), epsilon (ε), gamma (γ), and mu (μ). The type of heavy chain defines the class of antibody, i.e., IgA, IgD, IgE, IgG, and IgM, respectively. The γ and α classes are further divided into subclasses on the basis of differences in the constant domain sequence and function, e.g., IgG1, IgG2A, IgG2B, IgG3, IgG4, IgA1 and IgA2. In mammals there are two types of immunoglobulin light chains, λ and κ.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see. e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and U.S. Pat. No. 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

As used herein, the term "heavy-chain-only antibody" (HCAb) refers to an antibody which consists only of two heavy chains and lacks the two light chains usually found in full-length antibodies.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For a review of methods for assessment of antibody purity, see, e.g., Flatman et al., J. Chromatogr. B 848:79-87 (2007). In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term an "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The terms "light chain variable region" (also referred to as "light chain variable domain" or "VL" or $V_L$) and "heavy chain variable region" (also referred to as "heavy chain variable domain" or "VH" or $V_H$) refer to the variable binding region from an antibody light and heavy chain, respectively. The variable binding regions are made up of discrete, well-defined sub-regions known as "complementarity determining regions" (CDRs) and "framework regions" (FRs), generally comprising in order FR1-CDR1-FR2-CDR2-FR3-CDR3-FR4 from amino-terminus to carboxyl-terminus. In one embodiment, the FRs are humanized. The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 domain of the heavy chain linked to the light chain via an inter-chain disulfide bond.

As used herein, the term "binding domain" or "binding region" refers to the domain, region, portion, or site of a protein, polypeptide, oligopeptide, or peptide or antibody or binding domain derived from an antibody that possesses the ability to specifically recognize and bind to a target molecule, such as an antigen, ligand, receptor, substrate, or inhibitor (e.g., CD152). Exemplary binding domains include single-chain antibody variable regions (e.g., domain antibodies, sFv, scFv, scFab), receptor ectodomains, and ligands (e.g., cytokines, chemokines). In certain embodiments, the binding domain comprises or consists of an antigen binding site (e.g., comprising a variable heavy chain sequence and variable light chain sequence or three light chain complementary determining regions (CDRs) and three heavy chain CDRs from an antibody placed into alternative framework regions (FRs) (e.g., human FRs optionally comprising one or more amino acid substitutions). A variety of assays are known for identifying binding domains of the present disclosure that specifically bind a particular target, including Western blot, ELISA, phage display library screening, and BIACORE® interaction analysis. As used herein, a "CD152-binding domain" can have an immunoglobulin heavy chain variable regions comprising three heavy chain CDRs: CDR1, CDR2, and CDR3.

An antibody or binding domain "specifically binds" a target if it binds the target with an affinity or $K_a$ (i.e., an equilibrium association constant of a particular binding interaction with units of 1/M) equal to or greater than $10^5$ M$^{-1}$, while not significantly binding other components present in a test sample. Antibodies or binding domains can be classified as "high affinity" antibodies or binding domains and "low affinity" antibodies or binding domains. "High affinity" antibodies or binding domains refer to those antibodies or binding domains with a K$_a$ of at least 10$^7$ M$^{-1}$, at least 10$^8$ M$^{-1}$, at least 10$^9$ M$^{-1}$, at least 10$^{10}$ M$^{-1}$, at least 10$^{11}$ M$^{-1}$, at least 10$^{12}$ M$^{-1}$, or at least 10$^{13}$ M$^{-1}$. "Low affinity" antibodies or binding domains refer to those antibodies or binding domains with a K$_a$ of up to 10$^7$ M$^{-1}$, up to 10$^6$ M$^{-1}$, up to 10$^5$ M$^{-1}$. Alternatively, affinity can be defined as an equilibrium dissociation constant (K$_d$) of a particular binding interaction with units of M (e.g., 10$^{-5}$ M to 10$^{-13}$ M). In the case of an antibody binding to an antigen, K$_a$=1/K$_d$. Affinities of antibodies or binding domains according to the present disclosure can be readily determined using conventional techniques, such as surface plasmon resonance (see, e.g., Scatchard et al. (1949) Ann. N.Y. Acad. Sci. 51:660; and U.S. Pat. Nos. 5,283,173, 5,468,614, or the equivalent).

As used herein, "CD152" refers to cluster of differentiation 152, which is also known as cytotoxic T-lymphocyte-associated protein 4 (CTLA-4). The terms, "CD152," "CTLA-4," and "CTLA4" are used interchangeably herein. Similarly, "anti-CD152," "anti-CTLA-4," "anti-CTLA4" are also used interchangeably herein.

As used herein, "CD80" refers to cluster of differentiation 80, which is a protein found on dendritic cells, activated B cells and monocytes that provides a costimulatory signal necessary for T cell activation and survival. The terms, "CD80," "B7-1," and "B7.1" are used interchangeably herein.

As used herein, "CD86" refers to cluster of differentiation 86, which is a protein expressed on antigen-presenting cells that provides costimulatory signals necessary for T cell activation and survival. The terms, "CD86," "B7-2," and "B7.2" are used interchangeably herein.

As used herein, a "conservative substitution" is recognized in the art as a substitution of one amino acid for another amino acid that has similar properties. Exemplary conservative substitutions are well-known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, MA (1990), p. 8). In certain embodiments, a conservative substitution includes a leucine to serine substitution.

As used herein, "ipilimumab analogue" refers to a monoclonal antibody, which binds specifically to CTLA-4, comprising a heavy chain with an amino acid sequence of SEQ ID NO.: 199 and a light chain with an amino acid sequence of SEQ ID NO.: 200.

As used herein, unless otherwise indicated, any nonproprietary or generic name of a biological product includes the biological product and any biosimilar product thereof. For example, the nonproprietary name, ipilimumab, refers to the biological product sold under the trade name YERVOY; it also includes any biosimilar product of the biological product.

As used herein, unless otherwise indicated, the term "biosimilar product" refers to 1) a biological product having an amino acid sequence that is identical to a reference product; 2) a biological product having a different amino acid sequence (e.g., N- or C-terminal truncations) from a reference product; or 3) a biological product having a different posttranslational modification (e.g., glycosylation or phosphorylation) from a reference product, wherein the biosimilar product and the reference product utilize the same mechanism or mechanisms of action for the prevention, treatment, or cure of a disease or condition.

As used herein, the term "derivative" refers to a modification of one or more amino acid residues of a peptide by chemical or biological means, either with or without an enzyme, e.g., by glycosylation, alkylation, acylation, ester formation, or amide formation.

As used herein, a polypeptide or amino acid sequence "derived from" a designated polypeptide or protein refers to the origin of the polypeptide. In certain embodiments, the polypeptide or amino acid sequence which is derived from a particular sequence (sometimes referred to as the "starting" or "parent" or "parental" sequence) has an amino acid sequence that is essentially identical to the starting sequence or a portion thereof, wherein the portion consists of at least 10-20 amino acids, at least 20-30 amino acids, or at least 30-50 amino acids, or at least 50-150 amino acids, or which is otherwise identifiable to one of ordinary skill in the art as having its origin in the starting sequence. For example, a binding domain can be derived from an antibody, e.g., a Fab, F(ab')2, Fab', scFv, single domain antibody (sdAb), etc.

Polypeptides derived from another polypeptide can have one or more mutations relative to the starting polypeptide, e.g., one or more amino acid residues which have been substituted with another amino acid residue or which has one or more amino acid residue insertions or deletions. The polypeptide can comprise an amino acid sequence which is not naturally occurring. Such variations necessarily have less than 100% sequence identity or similarity with the starting polypeptide. In one embodiment, the variant will have an amino acid sequence from about 60% to less than 100% amino acid sequence identity or similarity with the amino acid sequence of the starting polypeptide. In another embodiment, the variant will have an amino acid sequence from about 75% to less than 100%, from about 80% to less than 100%, from about 85% to less than 100%, from about 90% to less than 100%, from about 95% to less than 100% amino acid sequence identity or similarity with the amino acid sequence of the starting polypeptide.

As used herein, unless otherwise provided, a position of an amino acid residue in a variable region of an immunoglobulin molecule is numbered according to the IMGT numbering convention (Brochet, X, et al, Nucl. Acids Res. (2008) 36, W503-508) and a position of an amino acid residue in a constant region of an immunoglobulin molecule is numbered according to EU nomenclature (Ward et al., 1995 Therap. Immunol. 2:77-94). Other numbering conventions are known in the art (e.g., the Kabat numbering convention (Kabat, Sequences of Proteins of Immunological Interest, 5$^{th}$ ed. Bethesda, MD: Public Health Service, National Institutes of Health (1991)).

As used herein, the term "human" antibody refers to an antibody of human origin or a humanized antibody.

As used herein, the term "humanized" refers to a process of making an antibody or immunoglobulin binding proteins and polypeptides derived from a non-human species (e.g., mouse or rat) less immunogenic to humans, while still retaining antigen-binding properties of the original antibody, using genetic engineering techniques. In some embodiments, the binding domain(s) of an antibody or immunoglobulin binding proteins and polypeptides (e.g., light and heavy chain variable regions, Fab, scFv) are humanized. Non-human binding domains can be humanized using techniques known as CDR grafting (Jones et al., Nature 321:522 (1986)) and variants thereof, including "reshaping" (Verhoeyen, et al., 1988 Science 239:1534-1536; Riechmann, et al., 1988 Nature 332:323-337; Tempest, et al., Bio/Technol 1991 9:266-271), "hyperchimerization" (Queen, et al., 1989 Proc Natl Acad Sci USA 86:10029-10033; Co, et al., 1991 Proc Natl Acad Sci USA 88:2869-2873; Co, et al., 1992 JImmunol 148:1149-1154), and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312). If derived from a non-human source, other regions of the antibody or immunoglobulin binding proteins and polypeptides, such as the hinge region and constant region domains, can also be humanized.

As used herein, the term "patient in need" or "subject in need" refers to a patient or a subject at risk of, or suffering from, a disease, disorder or condition that is amenable to treatment or amelioration with a CD152-binding antibody or a composition thereof provided herein.

As used herein, the term "pharmaceutically acceptable" refers to molecular entities and compositions that do not generally produce allergic or other serious adverse reactions when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable."

As used herein, the term "treatment," "treating," or "ameliorating" refers to either a therapeutic treatment or prophylactic/preventative treatment. A treatment is therapeutic if at least one symptom of disease in an individual receiving treatment improves or a treatment can delay worsening of a progressive disease in an individual, or prevent onset of additional associated diseases.

As used herein, the term "therapeutically effective amount (or dose)" or "effective amount (or dose)" of a specific binding molecule or compound refers to that amount of the compound sufficient to result in amelioration of one or more symptoms of the disease being treated in a statistically significant manner or a statistically significant improvement in organ function. When referring to an individual active ingredient, administered alone, a therapeutically effective dose refers to that ingredient alone. When referring to a combination, a therapeutically effective dose refers to combined amounts of the active ingredients that result in the therapeutic effect, whether administered serially or simultaneously (in the same formulation or concurrently in separate formulations).

As used herein, the terms, "Antibody-dependent cell-mediated cytotoxicity" and "ADCC," refer to a cell-mediated process in which nonspecific cytotoxic cells that express FcγRs (e.g., monocytic cells such as Natural Killer (NK) cells and macrophages) recognize bound antibody (or other protein capable of binding FcγRs) on a target cell and subsequently cause lysis of the target cell. In principle, any effector cell with an activating FcγR can be triggered to mediate ADCC. The primary cells for mediating ADCC are NK cells, which express only FcγRIII, whereas monocytes, depending on their state of activation, localization, or differentiation, can express FcγRI, FcγRII, and FcγRIII. For a review of FcγR expression on hematopoietic cells, see, e.g., Ravetch et al., 1991, Annu. Rev. Immunol., 9:457-92.

As used herein, the term "promoter" refers to a region of DNA involved in binding RNA polymerase to initiate transcription.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994)Mol. Cell. Probes 8:91-98). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

The term "expression" refers to the biosynthesis of a product encoded by a nucleic acid. For example, in the case of nucleic acid segment encoding a polypeptide of interest, expression involves transcription of the nucleic acid segment into mRNA and the translation of mRNA into one or more polypeptides.

The terms "expression unit" and "expression cassette" are used interchangeably herein and denote a nucleic acid segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. In addition to a transcriptional promoter and terminator, an expression unit can further include other nucleic acid segments such as, e.g., an enhancer or a polyadenylation signal.

The term "expression vector," as used herein, refers to a nucleic acid molecule, linear or circular, comprising one or more expression units. In addition to one or more expression units, an expression vector can also include additional nucleic acid segments such as, for example, one or more origins of replication or one or more selectable markers. Expression vectors are generally derived from plasmid or viral DNA, or can contain elements of both.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage "sequence identity" is calculated by determining the number of positions at which the identical nucleic acid base or amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. The comparison window for nucleic acid sequences can be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison window for polypeptide sequences can be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar sequence identity" or "substantial sequence identity" if the two sequences have at least 80%, at least 85%, at least 90%, at least 95%, at least 96%, at least 97%, at least 98%, or at least 99% sequence identity relative to each other.

Antibodies

Disclosed herein are human monoclonal antibodies comprising a CD152-binding domain. The antibodies can be heavy-chain-only antibodies. The antibodies can consist of only two heavy chains. The antibodies can comprise no light chains. The antibodies can bind specifically to CD152. The antibodies can be isolated monoclonal antibodies that bind specifically to CD152 with high affinity.

The anti-CD152 antibodies disclosed herein can bind specifically to human CD152. In some cases, the anti-CD152 antibodies can bind to human CD152 with high affinity (e.g., $K_D < 6.0*10^{-11}$ M). The anti-CD152 antibodies can have a comparable or higher affinity to CTLA-4 when compared to an ipilimumab analogue. The anti-CD152 antibodies can also block the binding of CD152 to its ligands B7.1. The anti-CD152 antibodies can have enhanced tumor/peripheral serum ratio than the ipilimumab analogue. The anti-CD152 antibodies can induce a higher ADCC, for example, the antibodies can induce at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, or at least about 20-fold increase of lysis activity by NK cells.

The anti-CD152 antibodies can comprise a CD152-binding domain, which comprises an immunoglobulin heavy chain variable region comprising CDR1, CDR2, and CDR3. The anti-CD152 antibodies can also comprise CDR1, CDR2, and CDR3 that differ from those of anti-CD152 antibodies disclosed herein by one or more conservative modifications. It is understood in the art that certain conservative sequence modification can be made which do not remove antigen binding. See, e.g., Brummell et al., 1993, *Biochem* 32:1180-8; de Wildt et al., 1997, *Prot. Eng.* 10:835-41; Komissarov et al., 1997, *J. Biol. Chem.* 272:26864-26870; Hall et al., 1992, *J. Immunol.* 149:1605-12; Kelley and O'Connell, 1993, *Biochem.* 32:6862-35; Adib-Conquy et al., 1998, *Int. Immunol.* 10:341-6 and Beers et al., 2000, *Clin. Can. Res.* 6:2835-43.

Pharmaceutical Compositions and Formulations

A pharmaceutical composition can comprise one or more anti-CD152 antibodies disclosed herein formulated together with a pharmaceutically acceptable excipient. An excipient is said to be a "pharmaceutically acceptable excipient" if its administration can be tolerated by a recipient patient. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy*, 20th Ed. (Lippincott Williams & Wilkins 2003), and in Gennaro, ed., *Remington's Pharmaceutical Sciences* (Mack Publishing Company, 19th ed. 1995). Sterile phosphate-buffered saline is one example of a pharmaceutically acceptable excipient. Formulations can further include one or more carriers, diluents, preservatives, solubilizers, buffering agents, albumin to prevent protein loss on vial surfaces, etc.

The amount of active ingredient which can be combined with a carrier material to produce a single dosage form can vary depending upon the subject being treated and the particular mode of administration and can generally be that amount of the pharmaceutical composition which produces a therapeutic effect. Generally, the amount of active ingredient can range from about 0.01% to about 99% (w/w) of the composition, for example, can be about 0.1%-1%, about 0.1%-5%, about 0.1%-10%, about 0.1%-20%, about 0.5%-1%, about 0.5%-5%, about 0.5%-10%, about 0.5%-20%, about 1%-5%, about 1%-10%, about 1%-20%, about 5%-10%, about 5%-20%, about 10%-20%, about 10%-30%, about 20%-30%, about 20%-40%, about 30%-40%, about 30%-50%, about 40%-50%, about 40%-60%, about 50%-60%, about 50%-70%, about 60%-70%, about 60%-80%, about 70%-80%, about 70%-90%, about 80%-90%, about 80%-95%, or 95%-99% of the pharmaceutical composition. Preferably, the amount of active ingredient can be from about 0.1% to about 70%, and most preferably from about 1% to about 30% of the pharmaceutical composition.

The pharmaceutical composition can be suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, e.g., intranasally, orally, vaginally, rectally, sublingually or topically. The pharmaceutical composition can be in the form of sterile aqueous solutions or dispersions. The pharmaceutical composition can also be formulated in a microemulsion, liposome, or other ordered structure suitable to high drug concentration.

The pharmaceutical composition may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form. The oral unit dosage form may be selected from the group consisting of: tablets, pills, pellets, capsules, powders, lozenges, granules, solutions, suspensions, emulsions, syrups, elixirs, sustained-release formulations, aerosols, and sprays.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

The monoclonal antibodies disclosed herein can be formulated to ensure proper distribution in vivo. For example, to ensure that the therapeutic antibody of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade, 1989, J. Clin. Pharmacol. 29:685; Umezawa et al., 1988, Biochem. Biophys. Res. Commun. 153:1038; Bloeman et al., 1995, FEBS Lett. 357:140; M. Owais et al., 1995, Antimicrob. Agents Chemother. 39:180; Briscoe et al., 1995, Am. J. Physiol. 1233:134; Schreier et al., 1994, J. Biol. Chem. 269:9090; Keinanen and Laukkanen, 1994, FEBS Lett. 346:123; and Killion and Fidler, 1994, Immunomethods 4:273.

The pharmaceutical composition may optionally contain one or more additional pharmaceutically active ingredients, such as another antibody or a drug. The pharmaceutical compositions of the invention also can be administered in a combination therapy with, for example, another anti-cancer agent, another anti-inflammatory agent, or a vaccine.

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

Methods of Treatment

Further disclosed herein is a method of treating a disorder by administering a subject a therapeutically effective amount of the antibody or the pharmaceutical composition disclosed herein. The anti-CD152 antibodies disclosed herein may be used in a method for treating a subject (for example, a human or a non-human primate) or for manufacture of a medicament for treating a subject. Generally, such methods include administering to a subject in need of such treatment an anti-CD152 antibodies as described herein.

The anti-CD152 antibodies disclosed herein may be used in a method for treating a subject (for example, a human or a non-human primate) or for manufacture of a medicament for treating a subject. Generally, such methods include administering to a subject in need of such treatment an anti-CD152 antibody as described herein. In some embodiments, the anti-CD152 antibody comprises at least one effector function selected from antibody-dependent cell-mediated cytotoxicity (ADCC) and/or complement-dependent cytotoxicity (CDC), such that the anti-CD152 antibody induces ADCC and/or CDC against CD152-expressing cells in the subject.

Also disclosed herein is a method for treating a disorder characterized by overexpression of a tumor antigen, such as cancer. Examples of tumor antigens that may be recognized by a bispecific anti-CD152 antibody may include PSMA, CD19, CD20, CD37, CD38, CD123, Her2, ROR1, RON, glycoprotein A33 antigen (gpA33) and CEA. Generally, such methods include administering to a subject in need of such treatment a therapeutically effective amount of an anti-CD152 antibody comprising a second binding domain that binds a tumor antigen as described herein. The anti-CD152 antibody can induce redirected T-cell cytotoxicity (RTCC) against tumor antigen-expressing cells in the subject.

The method can be used for treating cancers such as, prostate cancer, colorectal cancer, renal cell carcinoma, bladder cancer, salivary gland cancer, pancreatic cancer, ovarian cancer, non-small cell lung cancer, melanoma, breast cancer (e.g., triple negative breast cancer), adrenal cancer, mantle cell lymphoma, acute lymphoblastic leukemia, chronic lymphocytic leukemia, Non-Hodgkin's lymphoma, acute myeloid leukemia (AML), B-lymphoid leukemia, blastic plasmocytoid dendritic neoplasm (BPDCN), and hairy cell leukemia.

Also disclosed herein is a method for treating an autoimmune disorder comprising administering a therapeutically effective amount of the pharmaceutical compositions or anti-CD152 antibody described herein to a patient in need thereof.

Subjects for administration of the anti-CD152 antibodies as described herein include patients at high risk for developing a particular disorder as well as patients presenting with an existing such disorder. Typically, the subject has been diagnosed as having the disorder for which treatment is sought. Further, subjects can be monitored during the course of treatment for any change in the disorder (e.g., for an increase or decrease in clinical symptoms of the disorder). Also, in some variations, the subject does not suffer from another disorder requiring treatment that involves targeting CD152-expressing cells.

In prophylactic applications, pharmaceutical compositions can be administered to a patient susceptible to, or otherwise at risk of, a particular disorder in an amount sufficient to eliminate or reduce the risk or delay the onset of the disorder. In therapeutic applications, compositions can be administered to a patient suspected of, or already suffering from such a disorder in an amount sufficient to cure, or at least partially arrest, the symptoms of the disorder and its complications. An amount adequate to accomplish this is referred to as a therapeutically effective dose or amount. In both prophylactic and therapeutic regimes, agents can be administered in several dosages until a sufficient response has been achieved. Typically, the response is monitored and repeated dosages are given if the desired response starts to fade.

To identify subject patients for treatment according to the methods of the disclosure, accepted screening methods can be employed to determine risk factors associated with specific disorders or to determine the status of an existing disorder identified in a subject. Such methods can include, for example, determining whether an individual has relatives who have been diagnosed with a particular disorder. Screening methods can also include, for example, conventional work-ups to determine familial status for a particular disorder known to have a heritable component. For example, various cancers are also known to have certain inheritable components. Inheritable components of cancers include, for example, mutations in multiple genes that are transforming (e.g., Ras, Raf, EGFR, cMet, and others), the presence or absence of certain HLA and killer inhibitory receptor (KIR) molecules, or mechanisms by which cancer cells are able to modulate immune suppression of cells like NK cells and T-cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disorder of interest. In addition, a wide variety of immunological methods are known in the art that are useful to identify markers for specific disorder. For example, various ELISA immunoassay methods are available and well-known in the art that employ monoclonal antibody probes to detect antigens associated with specific tumors. Screening can be implemented as indicated by known patient symptomology, age factors, related risk factors, etc. These methods allow the clinician to routinely select patients in need of the methods described herein for treatment. In accordance with these methods, targeting pathological, tumor antigen-expressing cells can be implemented as an independent treatment program or as a follow-up, adjunct, or coordinate treatment regimen to other treatments.

Determination of effective dosages in this context is typically based on animal model studies followed up by human clinical trials and is guided by determining effective dosages and administration protocols that significantly reduce the occurrence or severity of the subject disorder in model subjects. Effective doses of the compositions of the present disclosure vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically effective amount is also one in which any undesired collateral effects are outweighed by the beneficial effects of administering an anti-CD152 antibody as described herein. For administration of an anti-CD152 antibody, a dosage may range from about 0.1 µg to 100 mg/kg or 1 µg/kg to about 50 mg/kg, and more usually 10 µg to 5 mg/kg of the subject's body weight. In more specific embodiments, an effective amount of the agent is between about 1 µg/kg and about 20 mg/kg, between about 10 µg/kg and about 10 mg/kg, or between about 0.1 mg/kg and about 5 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring clinical symptoms of the disorder.

Dosage of the pharmaceutical composition can be varied by the attending clinician to maintain a desired concentration at a target site. For example, if an intravenous mode of delivery is selected, local concentration of the agent in the bloodstream at the target tissue can be between about 0.01-50 nanomoles of the composition per liter, sometimes between about 1.0 nanomole per liter and 10, 15, or 25 nanomoles per liter depending on the subject's status and projected measured response. Higher or lower concentrations can be selected based on the mode of delivery, e.g., trans-epidermal delivery versus delivery to a mucosal surface. Dosage should also be adjusted based on the release rate of the administered formulation, e.g., nasal spray versus powder, sustained release oral or injected particles, transdermal formulations, etc. To achieve the same serum concentration level, for example, slow-release particles with a release rate of 5 nanomolar (under standard conditions) would be administered at about twice the dosage of particles with a release rate of 10 nanomolar.

The anti-CD152 therapeutic (e.g., anti-CD152 antibody) may also be administered at a daily dosage of from about 0.001 to about 10 milligrams (mg) per kilogram (mpk) of body weight, preferably given as a single daily dose or in divided doses about two to six times a day. For administration to a human adult patient, the therapeutically effective amount may be administered in doses in the range of 0.2 mg to 800 mg per dose, including but not limited to 0.2 mg per dose, 0.5 mg per dose, 1 mg per dose, 5 mg per dose, 10 mg per dose, 25 mg per dose, 100 mg per dose, 200 mg per dose, and 400 mg per dose, and multiple, usually consecutive daily doses may be administered in a course of treatment. The anti-CD152 therapeutic can be administered at different times of the day. In one embodiment the optimal therapeutic dose can be administered in the evening. In another embodiment the optimal therapeutic dose can be administered in the morning. The total daily dosage of the anti-CD152 therapeutic thus can in one embodiment range from about 1 mg to about 2 g, and often ranges from about 100 mg to about 1.5 g, and most often ranges from about 200 mg to about 1200 mg. In the case of a typical 70 kg adult human, the total daily dose of the anti-CD152 therapeutic can range from about 2 mg to about 1200 mg and will often range, as noted above, from about 0.2 mg to about 800 mg.

Dosage regimens can also be adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody, the dosage may range from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-CD152 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/ml and in some methods about 25-300 µg/ml.

A "therapeutically effective dosage" of an anti-CD152 antibody of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

With particular regard to treatment of solid tumors, protocols for assessing endpoints and anti-tumor activity are well-known in the art. While each protocol may define tumor response assessments differently, the RECIST (Response evaluation Criteria in solid tumors) criteria is currently considered to be the recommended guidelines for assessment of tumor response by the National Cancer Institute (see Therasse et al., *J. Natl. Cancer Inst.* 92:205-216, 2000). According to the RECIST criteria tumor response means a reduction or elimination of all measurable lesions or metastases. Disease is generally considered measurable if it comprises lesions that can be accurately measured in at least one dimension as ≥20 mm with conventional techniques or ≥10 mm with spiral CT scan with clearly defined margins by medical photograph or X-ray, computerized axial tomography (CT), magnetic resonance imaging (MRI), or clinical examination (if lesions are superficial). Non-measurable disease means the disease comprises of lesions <20 mm with conventional techniques or <10 mm with spiral CT scan, and truly non-measurable lesions (too small to accurately measure). Non-measureable disease includes pleural effusions, ascites, and disease documented by indirect evidence.

The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions (3) Progressive Disease (PD), defined as 20% increase in the sum of the longest diameter of target lesions or appearance of any new lesion; (4) Stable or No Response, defined as not qualifying for CR, PR, or Progressive Disease. (See Therasse et al., supra.)

Additional endpoints that are accepted within the oncology art include overall survival (OS), disease-free survival (DFS), objective response rate (ORR), time to progression (TTP), and progression-free survival (PFS) (see *Guidance for Industry: Clinical Trial Endpoints for the Approval of Cancer Drugs and Biologics*, April 2005, Center for Drug Evaluation and Research, FDA, Rockville, MD.)

The anti-CD152 antibodies can be used to suppress CTLA-4-mediated signaling pathways that negatively-regulate immune responses, and to therefore enhance tumor-specific immune responses, either as a monotherapy or in combination with anti-PD-L1 monoclonal antibodies or other anticancer drugs.

Methods of Preparing Antibodies

The antibodies disclosed herein can be a human heavy-chain-only antibody (HCAb) generated from Harbour humanized mice (U.S. Pat. Nos. 9,353,179, 9,346,877 and 8,921, 522, and European Patent Nos. 1776383 and 1864998). The molecules produced by the HCAb mice can be soluble and can have affinities, diversity and/or physico-chemical properties comparable to traditional human IgG antibodies.

The preparation of HCAbs from the HCAb mice can facilitate generation of soluble human VH domains, the minimal immunoglobulin recognition unit, and thus the construction of novel multi-functional molecules comprising either multiple VH domains or VH domain(s) coupled to other molecules, such as bi-specifics, Antibody Drug Conjugates or VH domain-derived diagnostic or therapeutic molecules.

The anti-CD152 antibodies can also be prepared using an antibody having one or more of the $V_H$ sequences of the anti-CD152 antibody disclosed herein as starting material to engineer a modified antibody. An antibody can be engineered by modifying one or more residues within the variable regions (i.e., $V_H$ and/or $V_L$), for example within one or more CDR regions and/or within one or more framework regions. Additionally or alternatively, an antibody can be engineered by modifying residues within the constant region (s), for example to alter the effector function(s) of the antibody.

Polynucleotide molecules comprising a desired polynucleotide sequence can be propagated by placing the molecule in a vector. Viral and non-viral vectors can be used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. To express a nucleic acid encoding a polypeptide disclosed herein, a nucleic acid molecule encoding the polypeptide, operably linked to regulatory sequences that control transcriptional expression in an expression vector, is introduced into a host cell. In addition to transcriptional regulatory sequences, such as promoters and enhancers, expression vectors can include translational regulatory sequences and a marker gene which is suitable for selection of cells that carry the expression vector. The gene product encoded by a polynucleotide of the disclosure is expressed in any convenient expression system, including, for example, bacterial, yeast, insect, amphibian and mammalian systems. In the expression vector, the polypeptide-encoding polynucleotide is linked to a regulatory sequence as appropriate to obtain the desired expression properties. These can include promoters, enhancers, terminators, operators, repressors, and inducers. The promoters can be regulated (e.g., the promoter from the steroid inducible pIND vector (Invitrogen)) or constitutive (e.g., promoters from CMV, SV40, Elongation Factor, or LTR sequences). These are linked to the desired nucleotide sequence using the techniques described above for linkage to vectors. Any techniques known in the art can be used. Accordingly, the expression vector will generally provide a transcriptional and translational initiation region, which can be inducible or constitutive, where the coding region is operably linked under the transcriptional control of the transcriptional initiation region, and a transcriptional and translational termination region.

An expression cassette can be introduced into a variety of vectors, e.g., plasmid, BAC, YAC, bacteriophage such as lambda, P1, M13, etc., plant or animal viral vectors (e.g., retroviral-based vectors, adenovirus vectors), and the like, where the vectors are normally characterized by the ability to provide selection of cells comprising the expression vectors. The vectors can provide for extrachromosomal maintenance, particularly as plasmids or viruses, or for integration into the host chromosome. Where extrachromosomal maintenance is desired, an origin sequence is provided for the replication of the plasmid, which can be low- or high copy-number. A wide variety of markers are available for selection, particularly those which protect against toxins, more particularly against antibiotics. The particular marker that is chosen is selected in accordance with the nature of the host, where, in some cases, complementation can be employed with auxotrophic hosts. Introduction of the DNA construct can use any convenient method, including, e.g., conjugation, bacterial transformation, calcium-precipitated DNA, electroporation, fusion, transfection, infection with viral vectors, biolistics, and the like. The disclosure relates to an expression vector comprising a nucleic acid segment, wherein said nucleic acid segment may comprise a nucleotide sequence set forth in SEQ ID NO: 1, 7, 13, 19, 25, 31, 37, 43, 49, 55, 61, 67, 73, 79, 85, 91, 97, 103, 109, 115, 121, 127, 133, 139, 145, 151, 163, 169, 175, 181, or 187.

Accordingly, proteins for use within the present disclosure can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook and Russell, *Molecular Cloning: A Laboratory Manual* (3rd ed., Cold Spring Harbor Laboratory Press, Cold Spring Harbor, NY, 2001), and Ausubel et al., *Short Protocols in Molecular Biology* (4th ed., John Wiley & Sons, 1999).

To direct a recombinant protein into the secretory pathway of a host cell, a secretory signal sequence (also known as a leader sequence) is provided in the expression vector. The secretory signal sequence can be that of the native form of the recombinant protein, or can be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences can be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts for production of recombinant proteins for use within the present disclosure. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., *supra*), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, UT); see also, e.g., Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Virginia. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." Exemplary selectable markers include a gene encoding resistance to the antibiotic neomycin, which allows selection to be carried out in the presence of a neomycin-type drug, such as G-418 or the like; the gpt gene for xanthine-guanine phosphoribosyl transferase, which permits host cell growth in the presence of mycophenolic acid/xanthine; and markers that provide resistance to zeocin, bleomycin, blastocidin, and hygromycin (see, e.g., Gatignol et al., *Mol. Gen. Genet.* 207:342, 1987; Drocourt et al., *Nucl. Acids Res.* 18:4009, 1990). Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci.* (Bangalore) 11:47-58, 1987. Transformation of insect cells and production of foreign polypeptides therein is disclosed by Guarino et al., U.S. Pat. No. 5,162,222 and WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide* (Chapman & Hall, London); O'Reilly et al., *Baculovirus Expression Vectors: A Laboratory Manual* (Oxford University Press., New York 1994); and *Baculovirus Expression Protocols. Methods in Molecular Biology* (Richardson ed., Humana Press, Totowa, NJ, 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, MD). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J Biol. Chem.* 270:1543-1549, 1995. In addition, transfer vectors can include an in-frame fusion with DNA encoding a polypeptide extension or affinity tag as disclosed above. Using techniques known in the art, a transfer vector containing a protein-encoding DNA sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the protein or interest is subsequently produced. Recombinant viral stocks are made by methods commonly used in the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, CA). See generally Glick and Pasternak, *Molecular Biotechnology, Principles & Applications of Recombinant DNA* (ASM Press, Washington, D.C., 1994). See also U.S. Pat. No. 5,300,435. Serum-free media are used to grow and maintain the cells. Suitable media formulations are known in the art and can be obtained from commercial suppliers. The cells are grown up from an inoculation density of approximately $2-5 \times 10^5$ cells to a density of $1-2 \times 10^6$ cells, at which time a recombinant viral stock is added at a multiplicity of infection (MOI) of 0.1 to 10, more typically near 3. Procedures used are generally described in available laboratory manuals (see, e.g., King and Possee, supra; O'Reilly et al., supra; Richardson, supra).

Fungal cells, including yeast cells, can also be used within the present disclosure. Yeast species of in this regard include, e.g., *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii,* and *Candida maltosa* are known in the art. See, e.g., Gleeson et al., *J Gen. Microbiol.* 132:3459-3465, 1986; Cregg, U.S. Pat. No. 4,882,279; and Raymond et al., *Yeast* 14:11-23, 1998. *Aspergillus* cells can be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus,* and other genera are also useful host cells within the present disclosure. Techniques for transforming these hosts and expressing foreign DNA sequences cloned therein are well-known in the art (see, e.g., Sambrook and Russell, supra). When expressing a recombinant protein in bacteria such as *E. coli,* the protein can be retained in the cytoplasm, typically as insoluble granules, or can be directed to the periplasmic space by a bacterial secretion sequence. In the former case, the cells are lysed, and the granules are recovered and denatured using, for example, guanidine isothiocyanate or urea. The denatured protein can then be refolded and dimerized by diluting the denaturant, such as by dialysis against a solution of urea and a combination of reduced and oxidized glutathione, followed by dialysis against a buffered saline solution. In the alternative, the protein can be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted proteins can be recovered from the periplasmic space in a soluble and functional form by disrupting the cells (by, for example, sonication or osmotic shock) to release the contents of the periplasmic space and recovering the protein, thereby obviating the need for denaturation and refolding. Antibodies, including single-chain antibodies, can be produced in bacterial host cells according to known methods. See, e.g., Bird et al., *Science* 242:423-426, 1988; Huston et al., *Proc. Natl. Acad. Sci. USA* 85:5879-5883, 1988; and Pantoliano et al., *Biochem.* 30:10117-10125, 1991.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Anti-CD152 antibodies may be purified by conventional protein purification methods, typically by a combination of chromatographic techniques. See generally *Affinity Chromatography: Principles* & Methods (Pharmacia LKB Biotechnology, Uppsala, Sweden, 1988); Scopes, *Protein Purification: Principles and Practice* (Springer-Verlag, New York 1994). Proteins comprising an immunoglobulin Fc region can be purified by affinity chromatography on immobilized protein A or protein G. Additional purification steps, such as gel filtration, can be used to obtain the desired level of purity or to provide for desalting, buffer exchange, and the like.

The following examples of the invention are to further illustrate the nature of the invention. It should be understood that the following examples do not limit the invention and that the scope of the invention is to be determined by the appended claims.

EXAMPLES

Example 1—Generation of Anti-CTLA-4 Antibodies

Human CTLA-4-ECD protein (Acro Bio) was used as an immunogen to generate anti-CTLA-4 antibodies. The uses of human immunoglobulin transgenic mouse technology for the development and preparation of human antibodies was first described by Abgenix (xeno mouse and Medarex (HuMab "mouse"); Lonberg et al., 1994, *Nature*, 368: 856-859; Lonberg and Huszar, 1995, *Internal Rev. Immunol.*, 13:65-93; Harding and Lonberg, 1995, *Ann. N.Y. Acad. Sci.*, 764:536-546).

HCAb mice were immunized with the human CTLA-4-ECD protein at 20 mg/per mouse every two weeks for three times, and six of them were immunized for additional five times at 44 mg/per mouse. Except for the first injection, where Stimune (Prionics) was used as an adjuvant, all boosts were done with the Ribi adjuvant (Sigma adjuvant system 56322-1VL). After immunization, single cell suspensions were isolated from the mouse bone marrow, spleen and lymph nodes. Then mouse plasma cells were isolated using plasma cell isolation kit (Miltenyi, Cat. No. 130-092-530). Briefly, total RNAs from mouse plasma cells were prepared, and reversely transcribed to cDNAs in a large pool. Human VH regions were amplified from the cDNAs using primers as follows.

```
Forward primer:
lib-3-23/53-S:
                              (SEQ ID NO: 193)
5'-GTGTCCAGTGTGAGGTGCAGCTG
and lib-3-11-S:
                              (SEQ ID NO: 194)
5'-GTGTCCAGTGTCAGGTGCAGCTG Reversed primer:
mG1hrv:
                              (SEQ ID NO: 195)
5'-GGCTTACAACCACAATCCCTGGGC
```

All of the amplified VH domain-containing PCR fragments were cloned into a mammalian expression vector pTT5. The obtained plasmids were transformed into bacteria (DH5α) by electroporation. Plasmids were duplicated and purified, and then transfected into HEK 293 cells for antibody production.

The 293 cells were incubated in 293 FreeStyle medium (12338018, Thermo) for 10 days, and supernatants were screened with an ELISA assay. Recombinant human CTLA4-his proteins (Acro Bio) were diluted in PBS with a concentration of 2 μg/mL, and 100 μL of the diluted CTLA-4-his proteins were added per well to ELISA microplates, which were incubated overnight at 4° C. to coat the plates with the recombinant proteins. The plates were then blocked with ELISA blocking solution (containing 2% BSA, 0.05% (v/v) Tween® 20, pH 7.4 PBS buffer, w/v) at 37° C. for two hours and then incubated with supernatants for 1 hour at 37° C. The plates were washed and incubated with horseradish peroxidase (HRP) conjugated goat anti-human IgG (H+L) antibody (A18805, Life technologies) at 37° C. for one hour. 100 μL of tetramethylbenzidine (TMB) were added, and the plates were incubated at room temperature for 15 minutes. 50 μL of 1N HCl were added to terminate the reaction. Thirty-five positive clones showing significant staining were picked out for further tests.

The 35 clones were sequenced, and 9 clones out of the 35 were chosen with unique CDR3 sequences. Nucletic acid and amino acid sequences of these 9 anti-CTLA-4 antibodies were summarized in Table 1. The HCAb antibodies contained two heavy chains only.

TABLE 1

Nucletic acid and amino acid sequences of human anti-CTLA-4 antibodies

| | SEQ ID Nos | | | | | |
|---|---|---|---|---|---|---|
| Clone ID | na-heavy chain | aa-heavy chain | aa-heavy chain variable region | aa-heavy chain CDR1 | aa-heavy chain CDR2 | aa-heavy chain CDR3 |
| CL3 | 1 | 2 | 3 | 4 | 5 | 6 |
| CL5 | 7 | 8 | 9 | 10 | 11 | 12 |
| CL11 | 13 | 14 | 15 | 16 | 17 | 18 |
| CL20 | 19 | 20 | 21 | 22 | 23 | 24 |
| CL22 | 25 | 26 | 27 | 28 | 29 | 30 |
| CL24 | 31 | 32 | 33 | 34 | 35 | 36 |
| CL25 | 37 | 38 | 39 | 40 | 41 | 42 |
| CL30 | 43 | 44 | 45 | 46 | 47 | 48 |
| CL34 | 49 | 50 | 51 | 52 | 53 | 54 | na: nucleic acid;
aa: amino acid

Example 2—Preparation and Purification of
Anti-CTLA-4 Antibodies

Step 1. Preparation of HEK 293F Cells
Overexpressing hCTLA-4

The nucleotide sequence encoding human CTLA-4 (SEQ ID NO: 196, encoding an amino acid sequence of SEQ ID NO: 197) was subcloned into a pcDNA3.1 vector (Clontech) to obtain a plasmid. HEK293 and CHO-K1 cells (Invitrogen) were transiently transfected with the plasmids using PEI, and transformants were cultured in DMEM culture media containing 0.5 g/mL penicillin/streptomycin and 10% (w/w) fetal bovine serum (FBS) for 2 weeks. A limited dilution into a 96-well culture plate was carried out, and the plate was incubated at 37° C. with 5% (v/v) $CO_2$ for approximately 2 weeks. Monoclones were expanded in 6-well plates, and the expanded clones were screened by flow cytometry using commercially available anti-hCTLA-4 antibodies (R&D Systems). Clones exhibiting higher growth rates and higher fluorescence intensity as measured by FACS were further expanded and cryopreserved in liquid nitrogen.

Step 2. Determining Binding Activity of
Anti-CTLA-4 Antibodies in HEK 293F Cell
Medium by ELISA and Cell Based FACS Binding
Assay Recombinant human CTLA4-his proteins (Acro Bio) were diluted in PBS with a concentration of 2 μg/mL, and 100 μL of the diluted CTLA-4-his proteins were added per well to ELISA microplates, which were incubated overnight at 4° C. to coat the plates with the recombinant proteins. The plates were then blocked with ELISA blocking solution (containing 2% BSA, 0.05% (v/v) Tween® 20, pH 7.4 PBS buffer, w/v) at 37° C. for two hours and then incubated with 293F cell medium containing anti-CTLA-4 antibodies (see Example 1) for 1 hour at 37° C. The plates were washed and incubated with horseradish peroxidase (HRP) conjugated goat anti-human IgG (H+L) antibody (A18805, Life technologies) at 37° C. for one hour. 100 μL of tetramethylbenzidine (TMB) were added, and the plates were incubated at room temperature for 15 minutes. 50 μL of iN HCl were added to terminate the reaction, and the OD450 nm was determined by an ELISA plate reader.

Meanwhile, 293-hCTLA-4 cells prepared in step 1 were cultured and used to measure the antibody binding activity. The cells were treated with enzyme-free cell dissociation solution (Versene solution, Invitrogen) and then collected. BSA was added to the cell suspension to a final concentration of 1%, and the cells were blocked for 30 minutes on ice and then washed twice with HBSS. The cells were collected after centrifugation and resuspended in FACS buffer (HBSS+1% BSA, v/v) at $2\times10^6$ cells/mL. 100 μL of the cell suspension was then added to each well of a 96-well plate. 100 μL of 293F cell medium containing anti-CTLA-4 antibodies (see Example 1) were added to each well of the 96-well plate and incubated for 1 hour on ice. Cells were washed twice with FACS buffer, and 100 μL of Alexa Fluor™ 488-labeled anti-human (H+L) antibody (Invitrogen) were added to the 96-well plate and incubated for 1 hour on ice. The samples were washed three times with FACS buffer, and 100 μL of fixation buffer (4% paraformaldehyde v/v) were added to each well and incubated for 10 minutes. The cells were then washed twice with FACS buffer and resuspended in 100 μL of FACS buffer. The mean fluorescence intensity (MFI) was determined using FACS Calibur (BD).

Step 3 Production and Purification of Leading
Candidate Antibodies

The concentration of antibodies from the HEK293 cells were about 1-10 μg/mL, and varied widely. In addition, the FBS and the components of the culture medium could interfere with the analysis. Therefore, it was necessary to perform small scale (1-5 mg) antibody production and purification.

The constructs containing nucleotide sequences encoding the anti-CTLA-4 antibodies (as listed in Table 1) were introduced into 293 cells. Supernatant containing target antibodies were harvested 6-7 days post transfection by centrifugation and filtration. Monoclonal antibodies were purified by passing them through 2 mL Protein G columns (GE Healthcare). Protein G columns were first equilibrated with PBS buffer (pH7.2), and the hybridoma culture supernatants were then applied to the equilibrated Protein G columns with a constant flow rate of 3 mL/minute. The columns were each then washed with PBS buffer having a volume 3 times larger than that of the column. The anti-CTLA-4 antibodies were then eluted with elution buffer (0.1M acetate buffer, pH2.5), and the UV absorbance of the eluates were monitored using a UV detector (A280 UV absorption peak). 10% of 1.0M Tris-HCL buffer was added to the eluates to neutralize the pH, and the samples were sterile-filtered by passing them through 0.22 micron filters. Sterile-filtered purified anti-CTLA-4 antibodies were obtained.

The concentrations of purified anti-CTLA-4 antibodies were determined by UV absorbance (A280/1.4), and the purity and endotoxin level (Lonza kit) were measured. The purified anti-CTLA-4 antibodies had endotoxin concentrations less than 1.0 EU/mg.

Example 3—Characterization of Leading Candidate
Antibodies 293 cells were stably transfected with pTT5 plasmids containing the nucleic acid sequence encoding human CTLA-4 (SEQ ID NO: 196) to generate 293F cells stably expressing human CTLA-4 (herein referred to as 293-hCTLA-4 cells). Additional 293 cells were stably transfected with pIRES plasmids containing the nucleic acid sequence encoding full length cyno CTLA-4 (SEQ ID NO: 198) to generate 293 cells stably expressing cyno CTLA-4 (herein referred to as 293-cynoCTLA-4 cells). 293-hCTLA-4 and 293-cynoCTLA-4 cells were cultured and expanded in T-75 culture flasks to 90% confluence. The culture medium was aspirated, and the cells were washed twice with HBSS (Hanks Balanced Salt Solution, Invitrogen). The cells were treated with enzyme-free cell dissociation solution (Versene solution, Invitrogen) and collected. The cells were then washed twice with HBSS, cell counts were determined, and cells were resuspended with HBSS at $2\times10^6$ cells/mL. BSA was added to the cell suspension to a final concentration of 1%, and the cells were blocked for 30 minutes on ice and then washed twice with HBSS. The cells were collected after centrifugation and resuspended in FACS buffer (HBSS+1% BSA, v/v) at $2\times10^6$ cells/mL. 100 μL of the cell suspension were then added to each well of a 96-well plate. 100 μL of purified anti-CTLA-4 antibodies from Example 2 or control antibodies were added to each well of the 96-well plate and incubated for 1 hour on ice, wherein the heavy chain and light chain of the Ipilimumab analogue had amino acid sequences of SEQ ID NO.: 199 and SEQ ID NO.: 200, respectively. Cells were washed twice with FACS buffer, and 100 µL of Alexa Fluor™ 488-labeled anti-human (H+L) antibody (Invitrogen) were added to the 96-well plate and incubated for 1 hour on ice. The samples were washed three times with FACS buffer, and 100 µL of fixation buffer (containing 4% paraformaldehyde, v/v) were added to each well and incubated for 10 minutes. The cells were then washed twice with FACS buffer and resuspended in 100 µL of FACS buffer.

Figure 2:
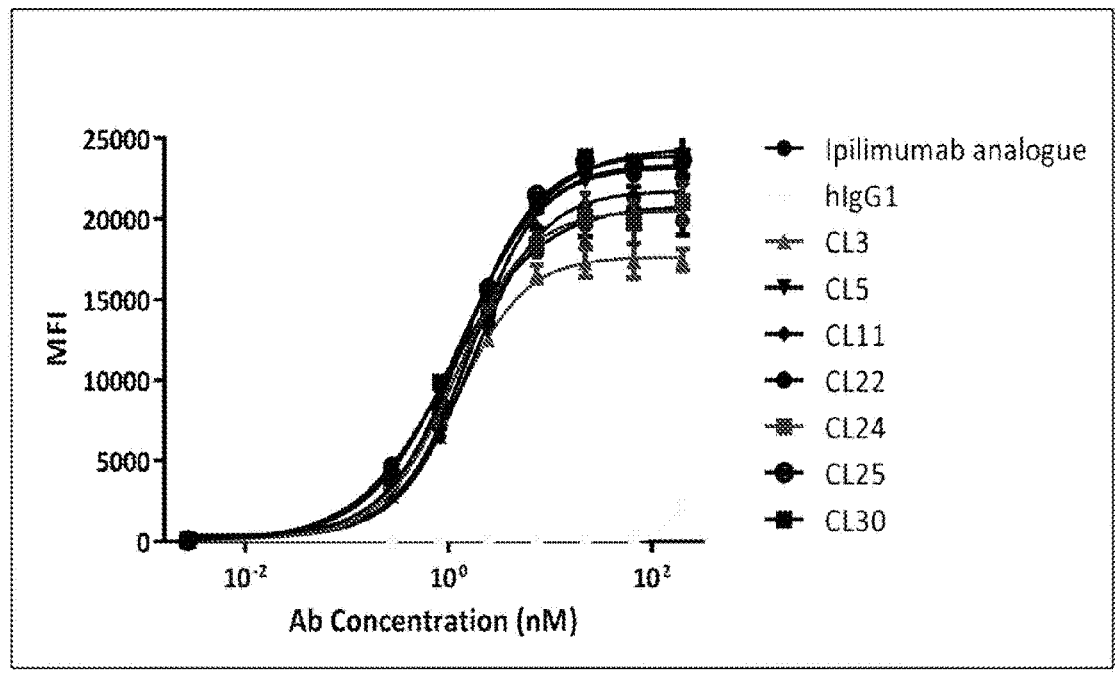
FIG. 2 shows the binding activity of the anti-CTLA-4 antibodies of the present invention to cynomolgus CTLA-4 expressed on 293 cells.

The mean fluorescence intensity (MFI) was determined using FACS Calibur (BD), and the results were shown in FIG. 1 and FIG. 2. The antibodies from Example 2 had binding activity to human or cyno CTLA on 293F cells comparable to the Ipilimumab analogue.

Example 4—Determination of Anti-CTLA-4 Antibodies' Ability to Block Binding of CTLA-4 to B7.1

Cell-based receptor-ligand binding assay was performed to determine the ability of the anti-CTLA-4 antibodies to block the binding of CTLA-4 to its ligands B7.1. Recombinant $B7.1^{ECD}$-Fc protein (B71-H5259, Acro Bio) was biotinylated using EZ-LINK NHS-PEG12-Biotin (Thermo Scientific #21312) according to the manufacturer's instruction. Biotinylated $B7.1^{ECD}$-Fc protein was concentrated and free label removed by using Amicon centrifugal filter (10 kDa cut off). The extracellular domain of B7.1 corresponded to amino acids Va135-Asn242 of Uniprot database protein P33681.

293-hCTLA-4 cells prepared in Example 3 were cultured and expanded in T-75 culture flasks to 60-80% confluence. The culture medium was aspirated, and the cells were washed twice with PBS. The cells were treated with enzyme-free cell dissociation solution (Versene solution, Invitrogen) and collected. Dissociation solution was neutralized by the addition of 8 mL of culture medium, and cell counts were determined. Cells were centrifuged at 300 g for 5 minutes and resuspended in blocking buffer (containing 2% BSA, pH 7.4 PBS buffer, w/v) at $1 \times 10^6$ cells/mL. The cells were blocked for 15 minutes at 37° C. Meanwhile, the wells of 96-well round-bottom plates were blocked with 200 µL of blocking buffer for 1 hour at 37° C. The blocking buffer was discarded, and 200 µL of cells were dispensed to each well of the 96-well plates ($2 \times 10^5$ cells/well). The plates were centrifuged at 500 g for 5 minutes, and the supernatants were discarded. The cells were resuspended in 100 µL of anti-CTLA-4 antibodies prepared in blocking buffer with varying concentrations. 100 µL of biotinylated $B7.1^{ECD}$-Fc (60 µg/mL in blocking buffer) were added to each well of 96-well plate and mixed by shaking gently. The plates were incubated at 4° C. for 90 minutes and washed twice with 200 µL blocking buffer. The blocking buffer was discarded, and the cells were resuspended in 100 µL of streptavidin-Alexa Fluor™ 488 solution (Invitrogen, 1:500 in blocking buffer) and incubated at 4° C. for 1 hour. The plates were washed three times with blocking buffer and added with 200 µL of blocking buffer.

Figure 3:
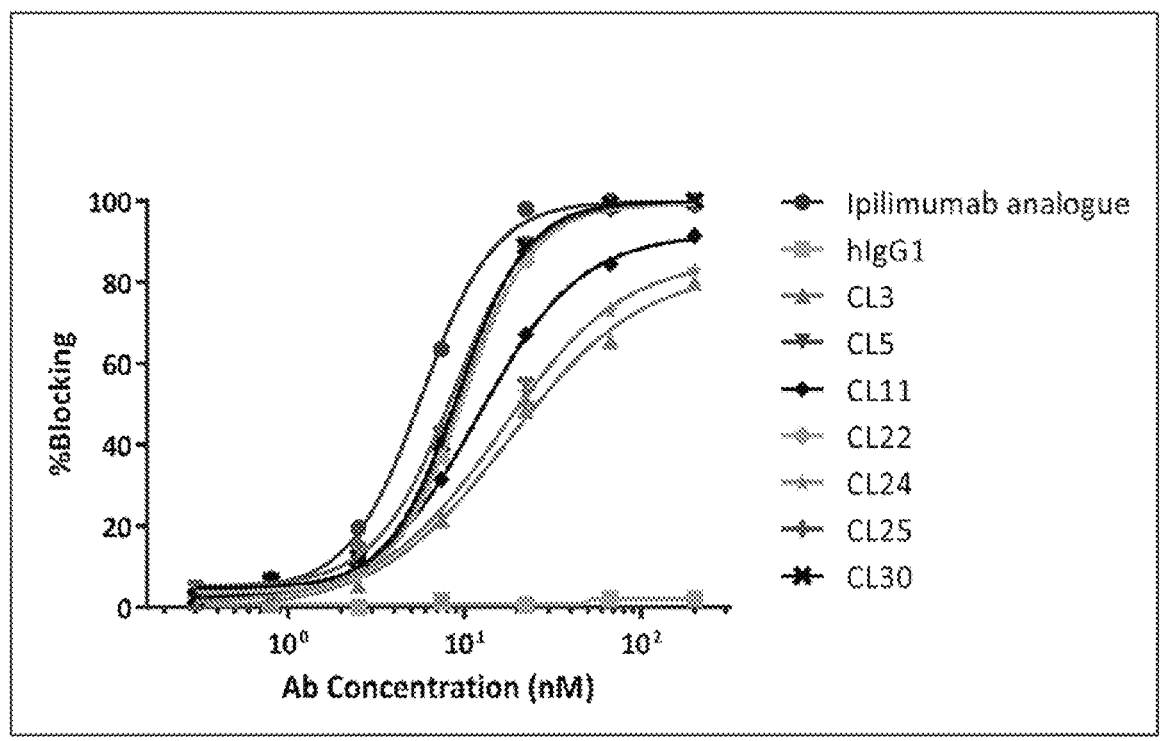
FIG. 3 shows the capacity of the anti-CTLA-4 antibodies of the present invention on blocking interaction between CTLA-4 and B7.1.

The mean fluorescence intensity (MFI) was determined using FACS Calibur (BD). The results, as shown in FIG. 3, demonstrated that the anti-CTLA-4 antibodies can block the binding of cell-expressed CTLA-4 to its ligand B7.1 at a level comparable to the Ipilimumab analogue.

Example 5—Anti-CLTA-4 HCAb Antibodies Promoted IL-20 Release

Step 1 PBMC Stimulation Test

100 µL of PBMC (containing $1 \times 10^5$ cells) were added to the wells of a 96-well plate, and 50 µL of each test antibody having various concentrations was then added to the 96-well plate and incubated for 15 minutes at room temperature. 50 µL of 100 ng/ml SEB were added to each well and cultured at 37° C., 5% $CO_2$ for 72 hours. The supernatants were collected and stored at −20° C. until analysis.

Step 2 Detection of Interleukin IL-2 Secretion by ELISA

Quantification of the levels of IL-2 in culture supernatant was carried out using Human IL-2 Quantikine® ELISA Kit (DY202, R&D Systems) following the manufacturer-provided operating instructions. Briefly, the anti-IL-2 polyclonal antibodies were coated onto the ELISA microplates, and 100 µL of the culture supernatant as well as the standard were added to each well and incubated at room temperature for 2 hours. The plates were washed 4 times with wash buffer, followed by the addition of HRP-conjugated anti-human IL-2 antibodies, and incubated at room temperature for 2 hours. After washes, a chromogenic substrate (5120-0077, SeraCare) was added and incubated in the dark at room temperature for 30 minutes, and the reaction was terminated by the addition of a stop solution (E661006-0200, BBI Life sciences).

Figure 4A:
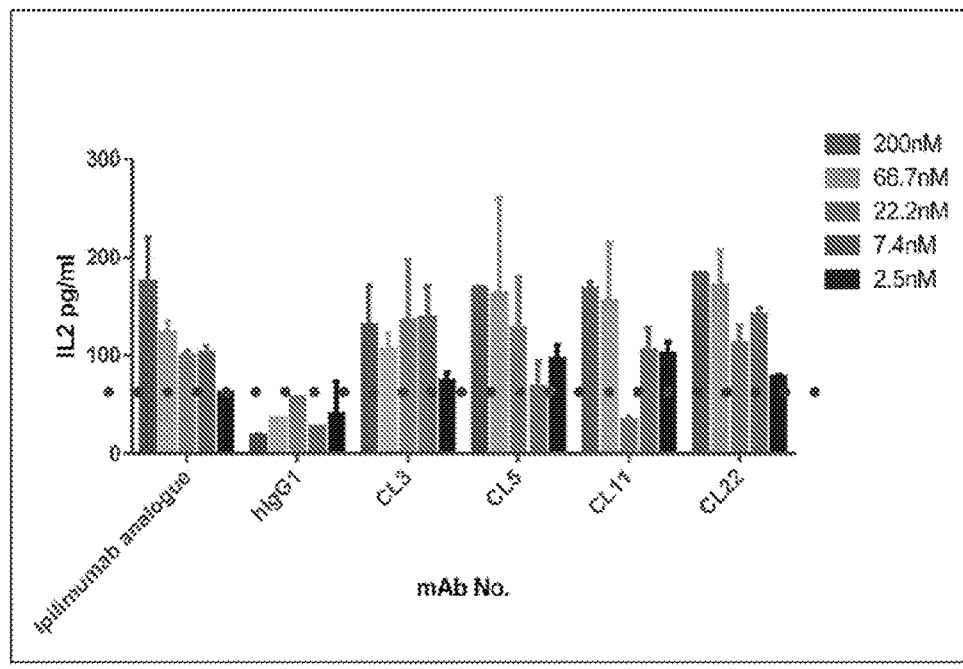
FIGS. 4A and 4B show the effect of the anti-CTLA-4 antibody CL3, CL5, CL11 and CL22 (A), and CL24, CL25 and CL30 (B) on IL-2 secretion in a SEB dependent T lymphocyte stimulation assay using PBMC's from donor 1.
Figure 4B:
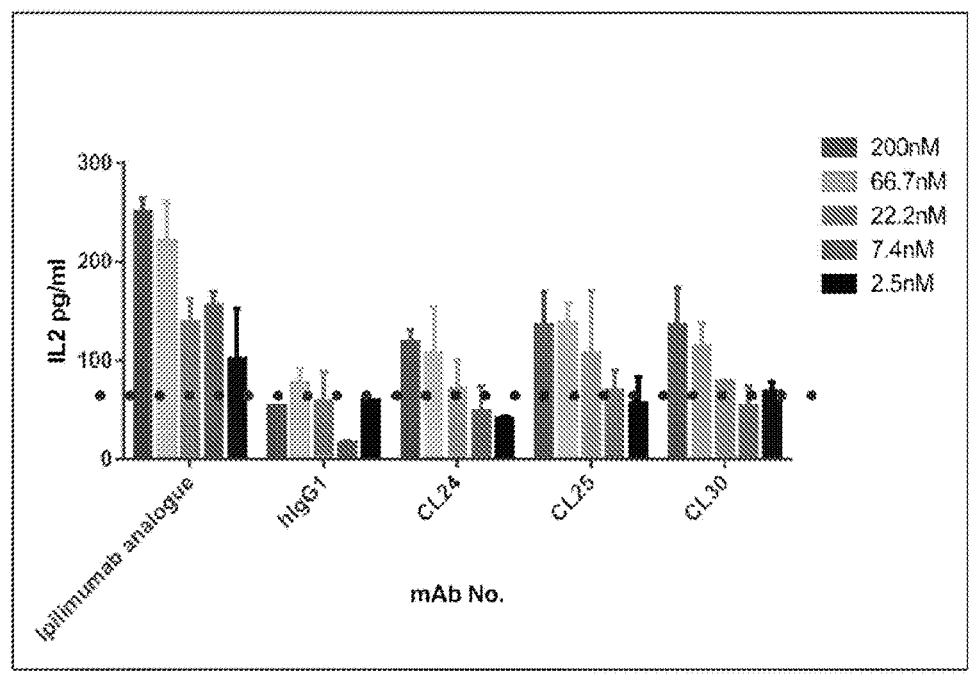

The absorbance at 450 nm was determined using an ELISA plate reader, and the results, as shown in FIGS. 4A and 4B, demonstrated that some of the anti-CTLA-4 antibodies can increase IL-2 secretion at low concentrations compared to human IgG (AB170090, Crown Bio) or the Ipilimumab analogue.

Example 6—Anti-CTLA-4 HCAb Antibodies Bound to Human CTLA-4 but not to Murine CTLA-4 in ELISA Assay Recombinant human or mouse CTLA4-his protein (CT4-H5229 for human protein, CT4-M52H5 for mouse protein, Acro Bio) was diluted in PBS to a concentration of 2 µg/mL, and 100 µL of the diluted CTLA-4-his protein was added per well to ELISA microplates, which were incubated overnight at 4° C. to coat the plates with the recombinant proteins. The plates were then blocked with ELISA blocking solution (containing 2% BSA, 0.05% (v/v) Tween®20, pH7.4 PBS buffer, w/v) at 37° C. for two hours and then incubated with anti-CTLA-4 antibodies with various concentrations for 1 hour at 37° C. The plates were washed and incubated with horseradish peroxidase (RP) conjugated goat anti-human IgG (H+L) antibody (A18805, Life technologies) at 37° C. for one hour. 100 µL of tetramethylbenzidine (TMB) were added, and the plates were incubated at room temperature for 15 minutes. 50 µL of iN HCl were added to terminate the reaction, and the OD450 nm was determined by an ELISA plate reader.

Figure 5A:
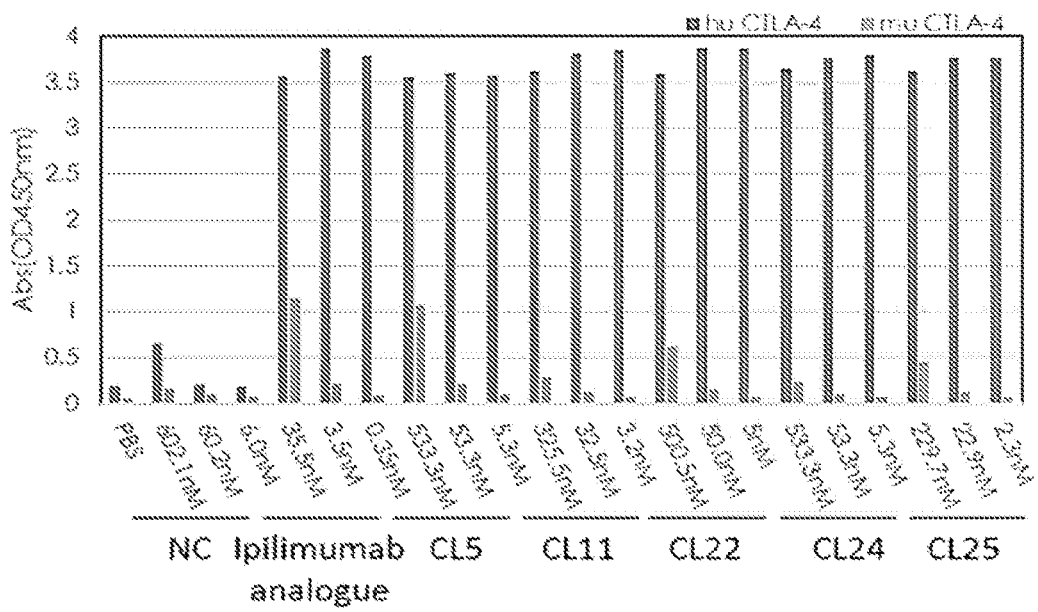
FIGS. 5A and 5B show the binding capacity of the anti-CTLA-4 antibodies antibody CL5, CL11, CL22, CL24 and CL25 (A) and CL5 (B) to human CTLA-4 or mouse CTLA-4.
Figure 5B:
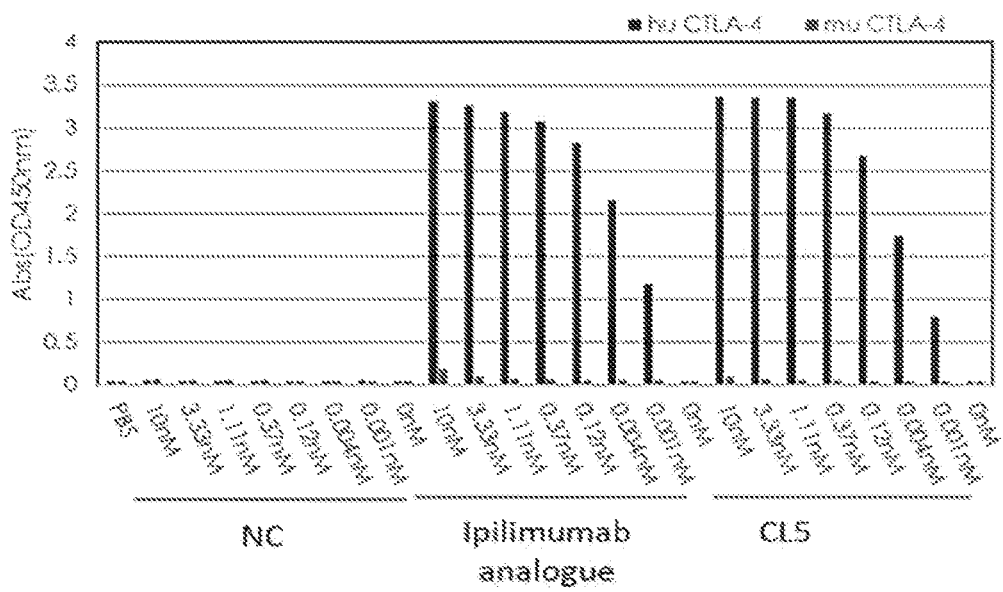

Data was shown in FIG. 5A and FIG. 5B, suggesting all clones bound to human CTLA-4 but almost did not bind to murine CTLA-4.

Example 7—Anti-CTLA-4 Antibody Mutants Promoted IL-20 Release

A T cell stimulation assay was performed on some antibodies mentioned above and their mutants to examine the effect of these antibodies on T cell stimulation by blocking the binding of CTLA-4 to its ligands B7.1 and B7.2.

The antibody mutants were prepared by applying S239D and 1332E mutations in the Fc constant domain of HCAb clone 5, clone 11, clone 22, clone 25 and clone 30 by PCR. The mutated antibodies were expressed in HEK293 cells and purified as described in Example 2. The nucleic acid and amino acid sequences of the antibody mutants were determined using standard molecular biology methods and are summarized in Table 2.

TABLE 2

Nucleic acid and amino acid sequences of anti-CTLA-4 antibody mutants

| Clone ID | na-heavy chain | aa-heavy chain | aa-heavy chain variable region | aa-heavy chain CDR1 | aa-heavy chain CDR2 | aa-heavy chain CDR3 |
|---|---|---|---|---|---|---|
| CL5-eA | 139 | 140 | 141 | 142 | 143 | 144 |
| CL11-eA | 115 | 116 | 117 | 118 | 119 | 120 |
| CL22-eA | 121 | 122 | 123 | 124 | 125 | 126 |
| CL25-eA | 127 | 128 | 129 | 130 | 131 | 132 |
| CL30-eA | 133 | 134 | 135 | 136 | 137 | 138 | na: nucleic acid;
aa: amino acid

PBMC stimulation test and Detection of interleukin IL-2 secretion by ELISA were performed as in Example 5.

Figure 6A:
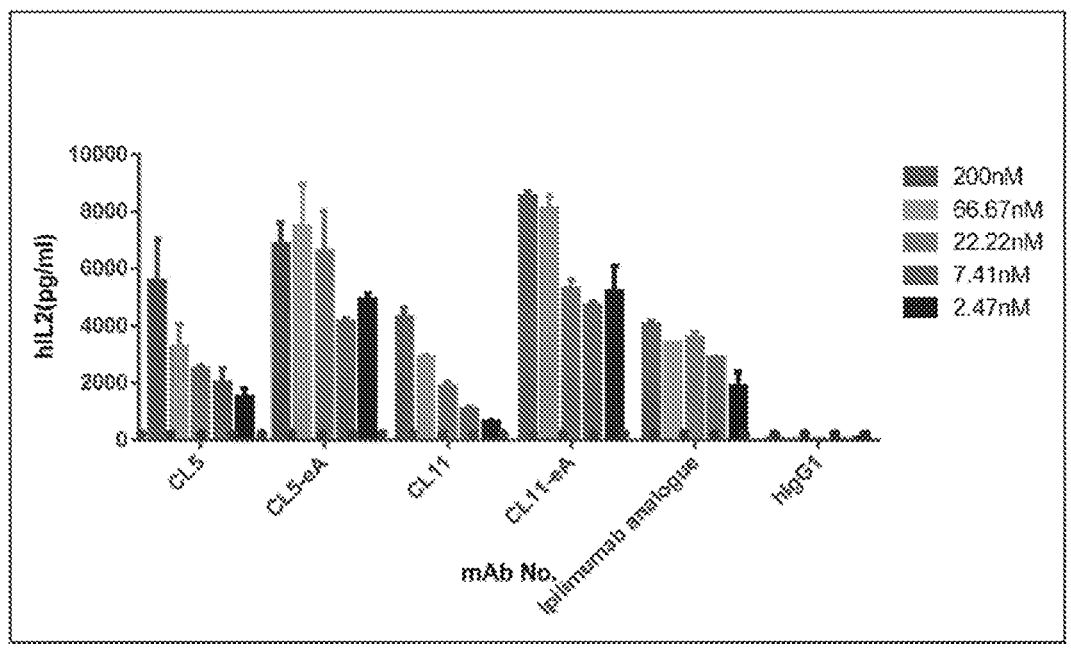
FIGS. 6A and 6B show the effect of anti-CTLA-4 antibody CL5, CL11 and their mutants (A), and CL22, CL25 and their mutants (B) on IL-2 secretion in a SEB dependent T lymphocyte stimulation assay using PBMC's from donor 2.
Figure 6B:
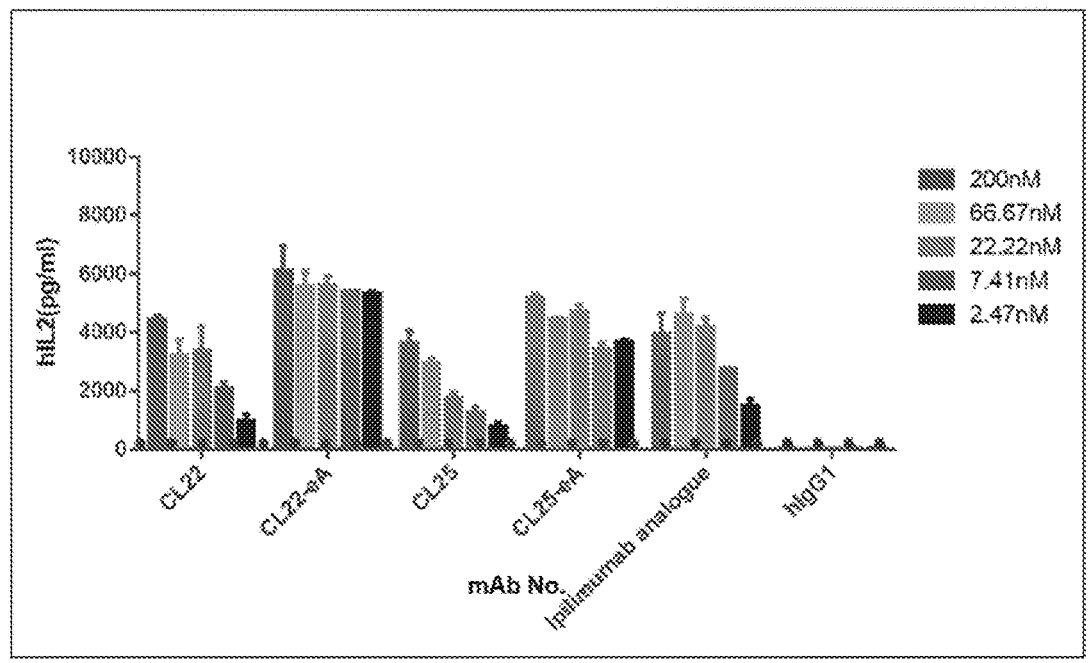

The results in FIGS. 6A and 6B demonstrated that the anti-CTLA-4 antibody mutants promoted more IL-2 secretion when compared to human IgG1 isotype control and their parental clones.

Example 8—Anti-CTLA-4 Antibody Variants with PTM Removed

The amino acid sequences of 7 HCAb clones (CL22, CL25, CL5, CL3, CL11, CL30, CL24) were aligned to gene IGHV3-53*01 and displayed in Table 3. The differences to germline gene and PTM sites were highlighted. The sequences were numbered in Chothia numbering scheme.

The germline gene IGHV3-53 does not have N-glycosylation motif natively, and those N-glycosylation motifs carried in the 7 HCAb clones were formed by somatic mutations. Therefore, one approach to remove this motif was to substitute it by the corresponding counterpart residues in germline, for example, to replace the NVS motif in CDR1 of CL11 by TVS of germline. Alternative approach was also explored by combining PTM removal with "germlining" based on the concept of CDR-grafting used for humanization. In the second approach, CDRs of each HCAb were grafted to germline IGHV3-53 frameworks and key framework residues from parental HCAb were also retained. For some antibodies, the amino acid mutations located in special residues, which may affect the binding activity between CTLA-4 and antibodies, were restored. The nucleic acid and amino acid sequences of human anti-CTLA-4 HCAb antibody variants with PTM removal were listed in Table 4.

TABLE 3

Differences of HCAb amino acid sequence compared to the germline sequence

| | Germline | | Critical PTM | | | | | | |
|---|---|---|---|---|---|---|---|---|---|
| Clone# | IGHV | Ident % | FR1 | CDR1 | FR2 | CDR2 | FR3 | CDR3 | FR4 |
| CL22 | IGHV3-53*02 | 89.7% | | | | | NxS/T | | |
| CL25 | IGHV3-53*02 | 96.9% | | | | | NxS/T | | |
| CL5 | IGHV3-53*02 | 86.6% | | NxS/T | | | | | |
| CL3 | IGHV3-53*02 | 88.7% | | NxS/T | | | NxS/T | | |
| CL11 | IGHV3-53*02 | 86.6% | | NxS/T | | | | | |
| CL30 | IGHV3-53*02 | 87.6% | | NxS/T | | | | | |
| CL24 | IGHV3-53*02 | 84.5% | | NxS/T | | | NxS/T | | |
| CL20 | IGHV3-74*03 | 98.0% | | | | NxS/T, NS, DG | | | |
| CL34 | IGHV3-74*03 | 88.8% | | | | NxS/T, NS, DG | | DG | |

TABLE 4

Nucleic acid and amino acid sequences of anti-CTLA-4 antibody variants with PTM removal

| | SEQ ID Nos | | | | | |
|---|---|---|---|---|---|---|
| Clone ID | na-heavy chain | aa-heavy chain | aa-heavy chain variable region | aa-heavy chain CDR1 | aa-heavy chain CDR2 | aa-heavy chain CDR3 |
| CL5-dPTM | 103 | 104 | 105 | 106 | 107 | 108 |
| CL5-dPTM' | 109 | 110 | 111 | 112 | 113 | 114 |
| CL5-eA-dPTM | 145 | 146 | 147 | 148 | 149 | 150 |
| CL5-eA-dPTM' | 151 | 152 | 153 | 154 | 155 | 156 |
| CL5'-dPTM' | 169 | 170 | 171 | 172 | 173 | 174 |
| CL5'-eA-dPTM' | 181 | 182 | 183 | 184 | 185 | 186 |
| CL11-dPTM | 55 | 56 | 57 | 58 | 59 | 60 |
| CL11-dPTM' | 61 | 62 | 63 | 64 | 65 | 66 |
| CL11'-dPTM' | 163 | 164 | 165 | 166 | 167 | 168 |
| CL11'-eA-dPTM' | 175 | 176 | 177 | 178 | 179 | 180 |
| CL20'-eA | 187 | 188 | 189 | 190 | 191 | 192 |
| CL22-dPTM | 67 | 68 | 69 | 70 | 71 | 72 |
| CL22-dPTM' | 73 | 74 | 75 | 76 | 77 | 78 |
| CL25-dPTM | 79 | 80 | 81 | 82 | 83 | 84 |
| CL25-dPTM' | 85 | 86 | 87 | 88 | 89 | 90 |
| CL30-dPTM | 91 | 92 | 93 | 94 | 95 | 96 |
| CL30-dPTM' | 97 | 98 | 99 | 100 | 101 | 102 | na: nucleic acid;
aa: amino acid

Example 9—Cell-Based Binding Activity of Anti-CTLA-4 Antibody Variants with PTM Removal Cell-based binding assay was performed to determine the binding ability of the anti-CTLA-4 antibody variants with PTM removal to human CTLA-4. The assay procedure was similar to that described in Example 3. Briefly speaking, 293F-hCTLA-4 cells were harvested using enzyme-free cell dissociation solution (Versene solution, Invitrogen) and then neutralized by culture medium, and cell counts were determined. Cells were centrifuged and blocked in blocking buffer (containing 2% BSA, pH 7.4 PBS buffer, w/v) at 1×10$^6$ cells/mL for 15 minutes at 37° C. 200 µL of cells were dispensed to each well of the 96-well plates (2×10$^5$ cells/well). The plates were centrifuged and the supernatants were discarded. The cells were resuspended in 100 µL of anti-CTLA-4 antibodies prepared in blocking buffer. The plates were incubated at 4° C. for 90 minutes and washed twice. After the blocking buffer was discarded, the cells were resuspended in 100 µL of Alexa Fluor™ 488-labeled anti-human (H+L) antibody (1:500, Invitrogen) and incubated at 4° C. for 1 hour. The cells were washed and resuspended in 200 µL of blocking buffer. The mean fluorescence intensity (MFI) was determined using FACS Calibur (BD).

Figure 7:
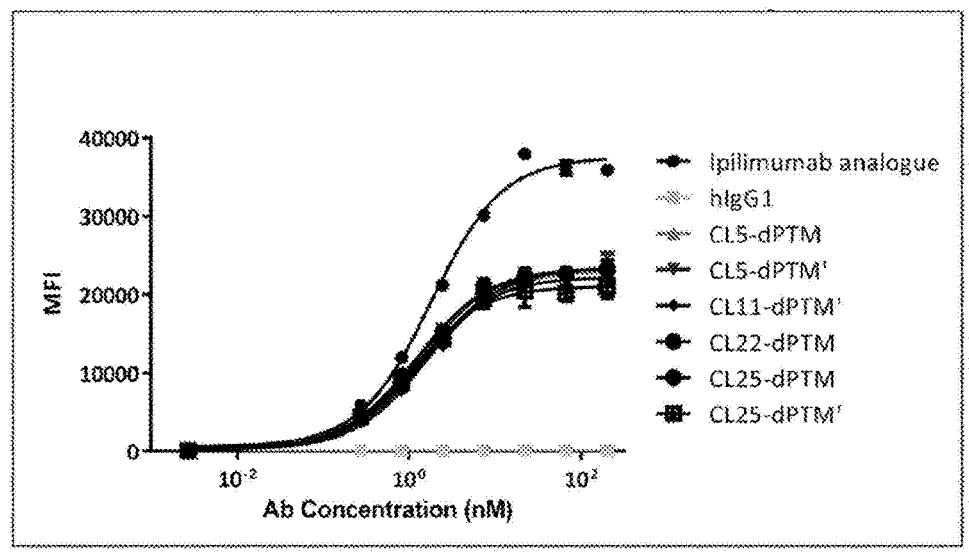
FIG. 7 shows the binding activity of anti-CTLA-4 antibody mutants to human CTLA-4.

The results, as shown in FIG. 7, demonstrated that the anti-CTLA-4 antibody variants with the PTM removal bound cell-expressed human CTLA-4.

Example 10—Blocking Activity of Anti-CTLA-4 Antibody Variants with PTM Removal on CTLA-4—B7.1 and B7.2 Interaction Cell-based receptor ligand binding assay was performed as described in Example 4 to determine the ability of the anti-CTLA-4 antibody variants with PTM removal to block the binding of CTLA-4 to its ligands B7.1.

Figure 8:
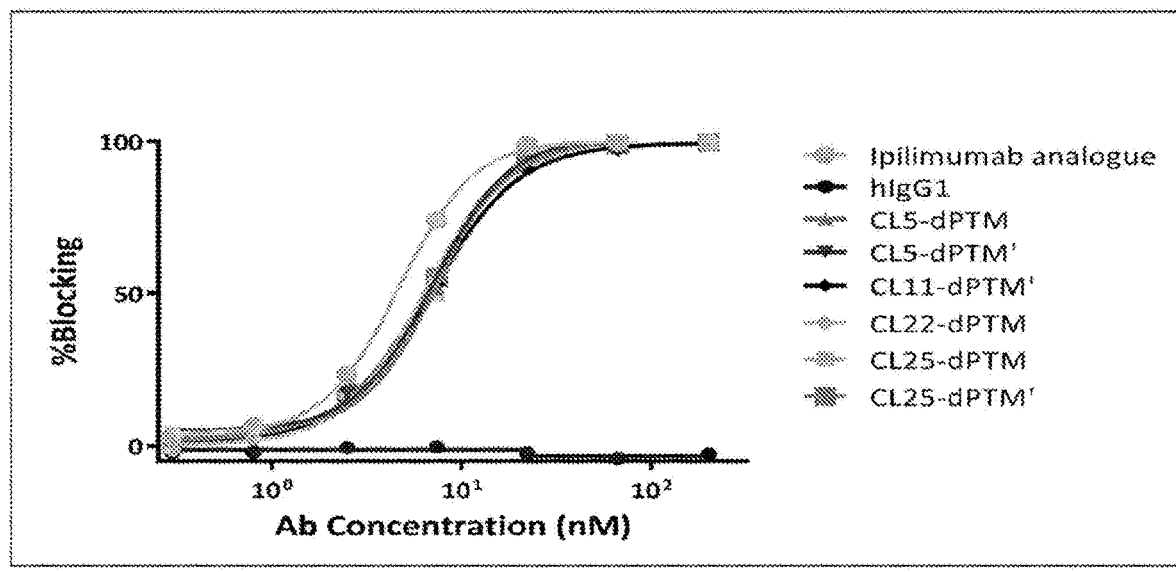
FIG. 8 shows the activity of anti-CTLA-4 antibody mutants on blocking interaction between CTAL-4 and biotin labeled B7.1.

The results, as shown in FIG. 8, demonstrated that the anti-CTLA-4 antibody variants with PTM removal blocked the binding of cell-expressed CTLA-4 to its ligand B7.1 and B7.2 at a level comparable to the Ipilimumab analogue.

Example 11—Anti-CTLA-4 Antibody Variants with PTM Removal Promoted IL-20 Release PBMC stimulation and IL-20 level quantification were carried out as described in Example 5.

Figure 9:
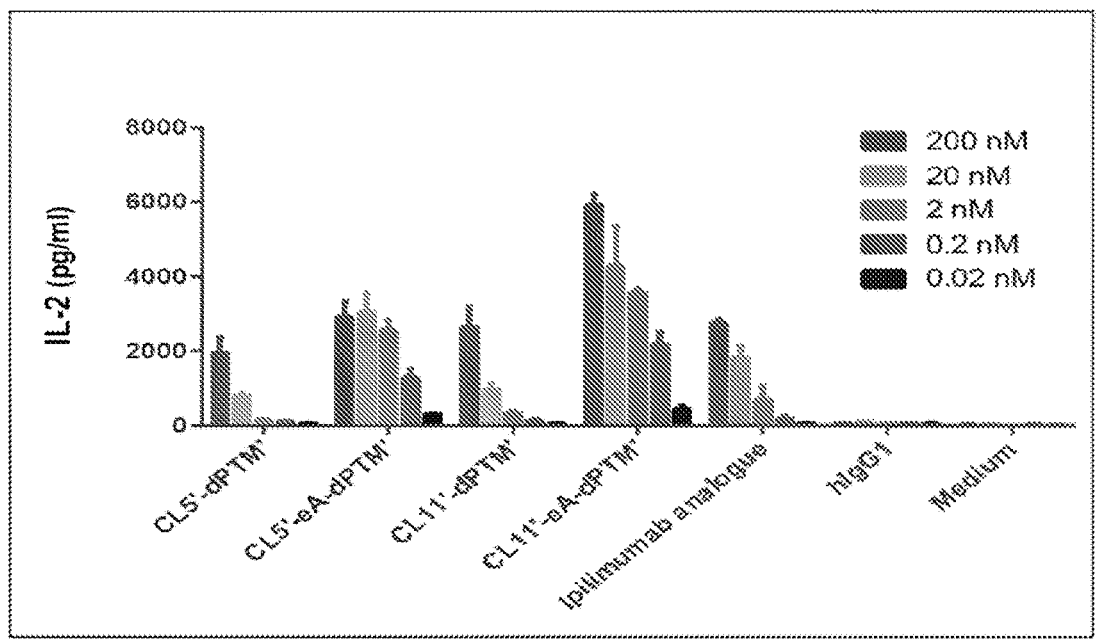
FIG. 9 shows the effect of anti-CTLA-4 antibody mutants on IL-2 secretion in a SEB dependent T lymphocyte stimulation assay using PBMC's from donor 3.

The results, as shown in FIG. 9, demonstrated that the anti-CTLA-4 antibody variants with PTM removal can still promote TL-2 secretion. The anti-CTLA-4 antibodies with S239D and 1332E mutations and PTM removal induced increased TL-2 secretion than those with S239D and 1332E mutations but no PTM removal.

Example 12—Binding Affinity and Dissociation Constant of Anti-CTLA-4 Antibody Variants with PTM Removal Dissociation constants were determined by Biacore T200 (GE Healthcare), following the specifications of the instrument provided by the manufacturer. Briefly, 1 µg/mL diluted anti-CTLA-4 antibodies in 10 mM NaOAc (pH 5.0, sigma) were immobilized on flow cell of a Series S CM5 sensor chip. Remaining active ester groups were blocked with 1 M ethanolamine (pH 8.5). With HBS-EP+as the running buffer, recombinant human CTLA-4-his (CT4-H5229, AcroBio) and cynoCTLA-4-his proteins (CT4-C5227, AcroBio) with five serial diluted concentrations were injected over flow cells at 30 µL/min with the association time of 180s. Buffer flow was maintained for dissociation for 600s. The KD value for each interaction between antibody and antigen was evaluated using Biacore T200 evaluation software 1.0 and the fitting model of 1:1 binding.

Figure 10:
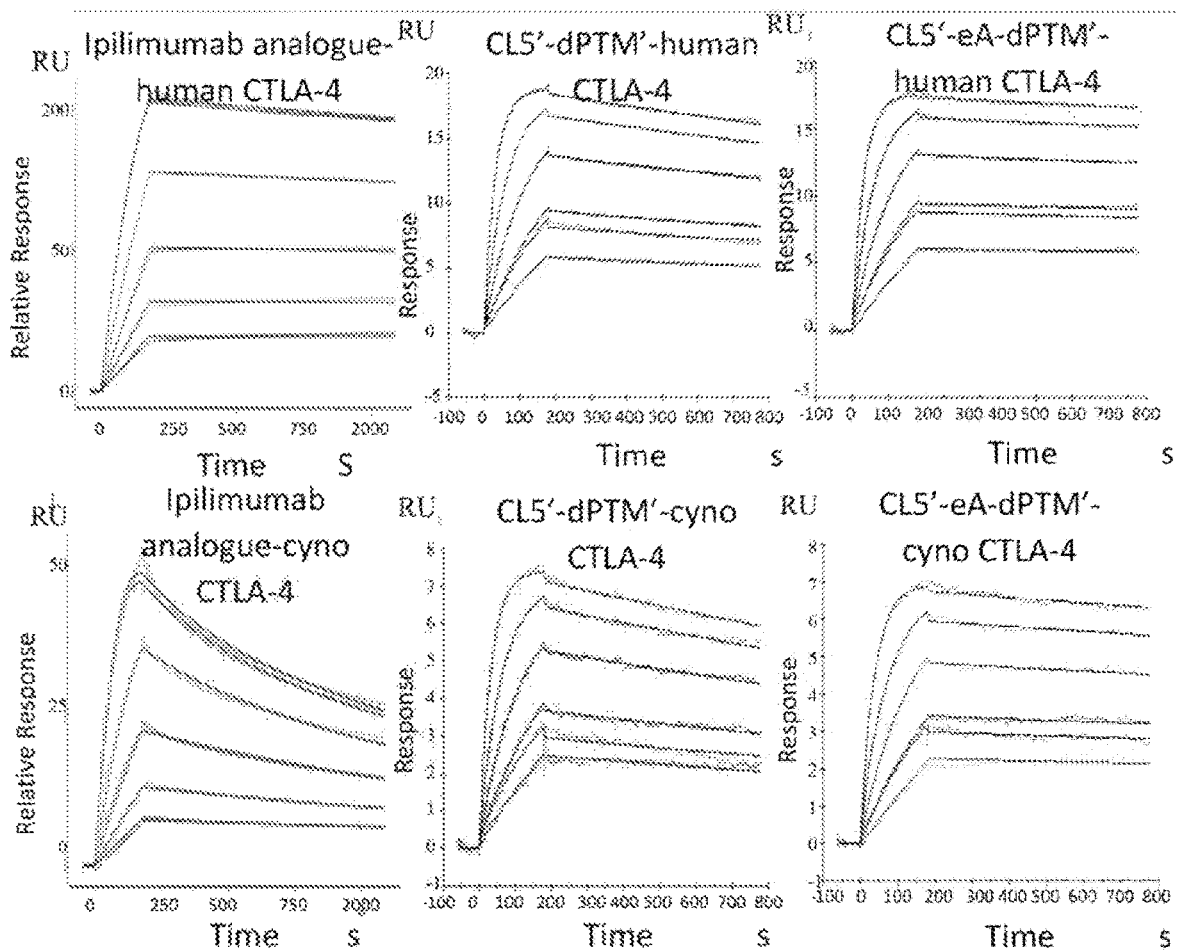
FIG. 10 shows the binding activity of anti-CTLA-4 antibody Ipilimumab analogue, CL5'dPTM' and CL5-eA-dPTM' to human CTLA-4 (Upper panel, from left to right), and the binding activity of Ipilimumab analogue, CL5'dPTM' and CL5-eA-dPTM' to cynomolgus CTLA-4 (lower panel, from left to right) as measured by BiaCore.

The results were shown in FIG. 10 and Table 5. The binding affinity of two clones were similar to that of the Ipilimumab analogue.

TABLE 5

Binding kinetics and affinities of human anti-CTLA-4 Abs to human CTLA-4$^{ECD}$-his protein and cynoCTLA-4$^{ECD}$-his protein as determined by Biacore T200

| Clone ID | Proteins | KD (M) | ka (1/Ms) | kd (1/s) |
|---|---|---|---|---|
| CL5'-dPTM' | Human CTLA-4$^{ECD}$-his | 4.28E−11 | 5.35E+06 | 2.29E−04 |
| CL5'-dPTM' | cyno CTLA-4$^{ECD}$-his | 5.91E−11 | 5.21E+06 | 3.08E−04 |
| CL5'-eA-dPTM' | Human CTLA-4$^{ECD}$-his | 1.40E−11 | 5.40E+06 | 7.58E−05 |
| CL5'-eA-dPTM' | cyno CTLA-4$^{ECD}$-his | 2.43E−11 | 4.55E+06 | 1.10E−04 |

TABLE 5-continued

Binding kinetics and affinities of human anti-CTLA-4 Abs to human CTLA-4$^{ECD}$-his protein and cynoCTLA-4$^{ECD}$-his protein as determined by Biacore T200

| Clone ID | Proteins | KD (M) | ka (1/Ms) | kd (1/s) |
| --- | --- | --- | --- | --- |
| Ipilimumab analogue | Human CTLA-4$^{ECD}$-his | 7.32E−11 | 1.23E+06 | 8.98E−05 |
| Ipilimumab analogue | cyno CTLA-4$^{ECD}$-his | 3.47E−10 | 3.73E+06 | 1.29E−03 |

Example 13—In Vitro ADCC Function Analysis

To confirm the presumed NK dependent cytotoxic activity of human anti-CTLA-4 antibodies, antibody-dependent cell-mediated cytotoxicity (ADCC) assay was performed both on CTLA-4-expressing CHO-K1 cells and CTLA-4 expressing in vitro stimulated Treg cells.

CTLA-4-expressing CHO-K1 cells as described in Example 2, step 1, were adjusted to a concentration of 2×10$^5$ cells/mL with ADCC medium (containing RPMI 1640 without phenol red, 10% FBS and 1% penicillin/streptomycin). 50 μL of cell suspensions (1×10$^4$ viable cells) were added to each well of a v-bottom 96-well plate. The test antibodies were serially diluted in ADCC medium (without phenol red) and 50 μL of each resulting solution was added to the wells in triplicate. The final antibody concentrations were: 0.087 pM, 0.44 pM, 2.2 pM, 10.9 pM, 54 pM, 272 pM, 1.36 nM, and 6.8 nM. The plate was incubated at 37° C. for 30 minutes. NK92 cells stably transfected with FcγRIII158V were adjusted with ADCC medium (without phenol red) so that by adding 100 μL of NK92 cells stably transfected with FcγRIII158V to the target cells, the ratio of effector to target cells was 5:1. The plate was then incubated at 37° C. for 6 hours. After 6 hours of incubation, the plate was centrifuged and 50 μL of each supernatant was transferred into a new plate. The supernatant was incubated with 50 μL LDH detection buffer at room temperature for 30 min and measured for the absorbance at 490 nm. For maximum cell lysis control, 50 μL of CTLA-4-expressing CHO-K1 cells, 50 μL of ADCC medium and 100 μL of 1% triton-X100 buffer were added for LDH detection. For minimum cell lysis control, 50 μL of CTLA-4-expressing CHO-K1 cells and 150 μL of ADCC medium were added for LDH detection. The absorbance at 492/650 nm was measured. The percentage of Cell lysis was calculated as 100*(absorbance of samples—absorbance of background)/(absorbance of maximum release—absorbance of minimum release). All the percentage of cell lysis values were calculated using GraphPad Prism 5.0.

Figure 11:
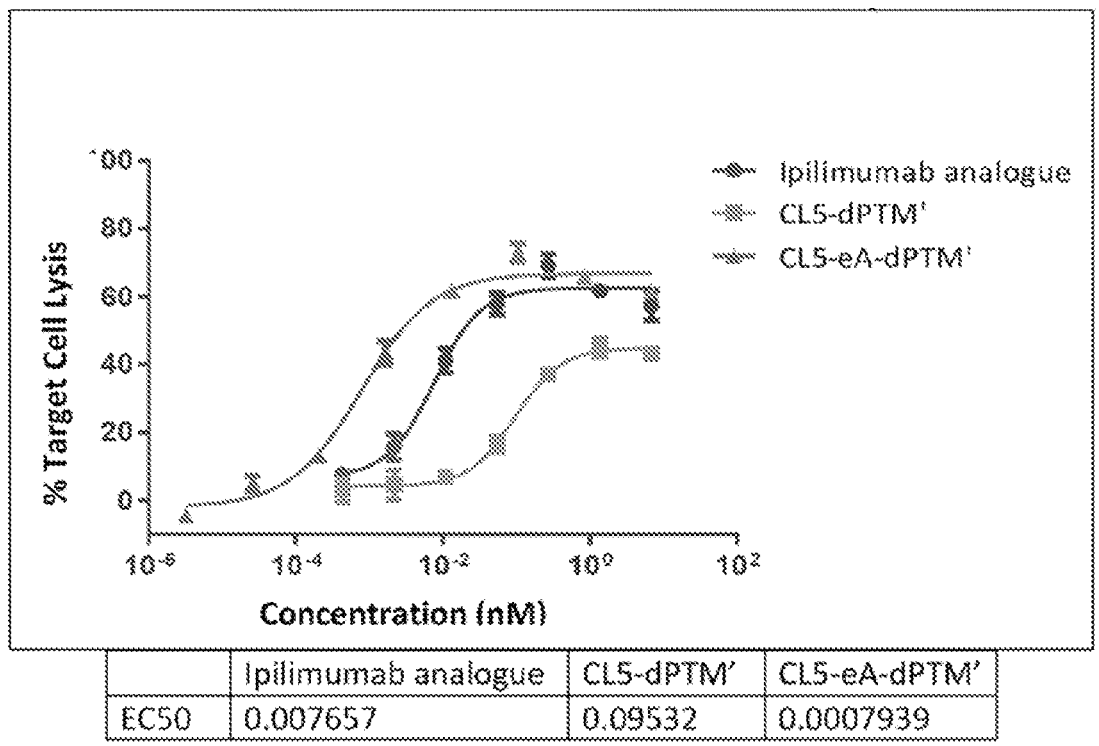
FIG. 11 shows the in vitro ADCC activity of anti-CTLA-4 antibody CL5 and its mutant on CHO K1-CTLA-4 cells.

The results, as shown in FIG. 11, showed that clone CL5-dPTM' antibody induced ADCC effect on CTLA-4-expressing CHO-K1 cells, and clone CL5-eA-dTPM' with additional S239D and I332E mutation showed a higher ADCC activity than Ipilimumab analogue.

CTLA-4-expressing in vitro stimulated Treg cells were derived from in vitro isolated naïve CD4+ T cells. First, naïve CD4+ T cells were isolated from primary PBMC according to the manufacturers instruction (Miltenyi, 130-094-131). Then naïve CD4+ T cells were activated by incubated with Dynabeads™ human T-activator CD3/CD28 (1:1) (Thermo, 11131D), 10 ng/ml IL-2 (PeproTech, 200-02-B) and 20 ng/ml TGF-β1 (PeproTech, 100-21) for three days. On the day of ADCC killing experiment, stimulated Treg cells were adjusted to a concentration of 1×10$^6$ cells/mL with ADCC medium (containing RPMI 1640 without phenol red, 10% FBS and 1% penicillin/streptomycin). 1×10$^6$ Cells were stained by 5 ul calcein AM (Therom, C34851, stock prepared as 50 ug per 50 ul DMSO) for 1 h at 37° C. Treg cells were washed three times by ADCC medium. 50 μL of Treg cell suspensions (5×10$^3$ viable cells) were added to each well of a v-bottom 96-well plate. The test antibodies were serially diluted in ADCC medium (without phenol red) and 50 μL of each resulting solution was added to the wells in triplicate. The final antibody concentrations were: 1 pM, 10 pM, 100 pM, 1 nM, 10 nM, and 100 nM. The plate was incubated at room temperature for 30 minutes. Fresh PBMC (Miaotong) were adjusted 5×10$^6$ cells/mL with ADCC medium (without phenol red). By adding 50 μL of fresh PBMC to the stained Treg cells, the ratio of effector to target cells was 50:1. The plate was then incubated at 37° C. for 2 hours. After 2 hours of incubation, the plate was centrifuged and 100 μL of each supernatant was transferred into a new plate. The supernatant was measured by Enspire instrument. For maximum cell lysis control, 50 μL of calcein AM stained Treg cells, 50 μL of ADCC medium and 100 μL of 1% triton-X100 buffer were added for released calcein AM detection. For minimum cell lysis control, 50 μL of calcein AM stained cells and 150 μL of ADCC medium were added for released calcein AM detection. The absorbance at 520/650 nm was measured. The percentage of specific killing is calculated as 100*(absorbance of samples—absorbance of background)/(absorbance of maximum release—absorbance of minimum release). All the percentage of specific killing values were calculated using GraphPad Prism 5.0.

The results showed that the human anti-CTLA-4 antibodies induced ADCC effect on CTLA-4-expressing Treg cells, and the antibody with S239D and I332E mutation showed a higher ADCC activity than the unmutated one.

Example 14—Pharmacokinetic Study of Anti-CTLA-4 Antibodies

Step 1 Single Dose Anti-CTLA-4 Antibody Treatment in Mice

Male C57BL/6 mice were injected with 3 mg/kg anti-CTLA-4 antibodies via tail vein to measure the serum concentration of anti-CTLA-4 antibodies. The animals were restrained manually and approximately 100 μL blood/time point was collected via retro-orbital puncture, the time point being Pre-dose, 0.167, 1, 4, 8, 24 hr, 2, 4, 7, 14 days post antibody injection. The terminal collection was via cardiac puncture. Blood samples were stayed at room temperature and centrifuged at 2,000×g for 5 min at 4° C. to obtain serum samples.

Step 2 Serum Concentration of Anti-CTLA-4 Antibodies as Measured by ELISA

All serum samples were diluted at 20 folds in Assay Diluent first. Additional dilution was made in 5% mouse serum (PBS, v/v). Recombinant human CTLA4-his protein (Acro Bio) was diluted in PBS to a concentration of 0.5 pg/mL, and 50 µL of the diluted CTLA-4-his protein sample were added per well to ELISA microplates, which were incubated overnight at 4° C. to coat the plates with the recombinant proteins. The plates were then blocked with ELISA blocking solution (containing 2% BSA, 0.05% (v/v) Tween® 20, pH7.4 PBS buffer, w/v) at 37° C. for two hours. The blocking buffer was aspirated away and plates were incubated with diluted serum samples for 1 hour at 37° C. The plates were washed three times with wash buffer (PBS+ 0.01% (v/v) Tween® 20) and incubated with horseradish peroxidase (HRP) conjugated goat anti-human IgG (Fc) antibody (A0170, Sigma) at 37° C. for one hour. 100 µL of tetramethylbenzidine (TMB) were added, and the plates were incubated at room temperature for 15 minutes. 100 µL of 0.1N HCl was added to each well to stop the reaction. The absorbance at 450 nm was measured with an ELISA plate reader (SpectraMax M2).

Figure 12:
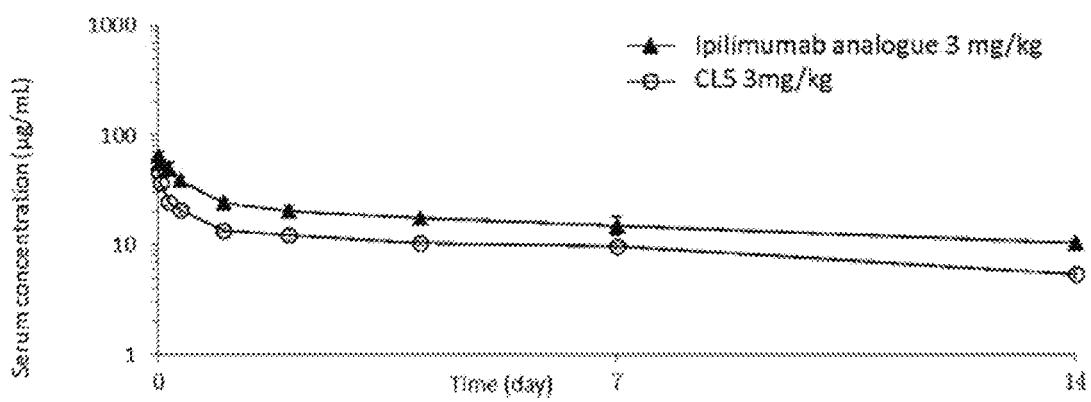
FIG. 12 shows the serum concentration-time profile of anti-CTLA-4 antibody CL5 in male C57BL/6 mice.

The corresponding serum concentration of anti-CTLA-4 antibodies were shown in FIG. 12, with detailed data listed in Table 6.

TABLE 6

Mean serum concentration of antibodies after an IV dose at 3 mg/kg in mice

Individual and mean serum concentration-time data of Ipilimumab analogue after an IV dose of 3 mg/kg in male C57BL/6 mice

| Dose (mg/kg) | Dose route | Sampling time (Day) | Concentration (µg/mL) Individual (#1~#12) | | | Mean (µg/mL) | SD | CV(%) |
|---|---|---|---|---|---|---|---|---|
| 3 | IV | 0 | BQL | BQL | BQL | BQL | NA | NA |
| | | 0.00694 | 67.3 | 69.8 | 60.2 | 65.8 | 4.99 | 7.59 |
| | | 0.0417 | 52.8 | 58.4 | 54.0 | 55.1 | 2.92 | 5.29 |
| | | 0.167 | 42.1 | 55.6 | 52.7 | 50.2 | 7.09 | 14.14 |
| | | 0.333 | 37.3 | 42.0 | 38.1 | 39.2 | 2.54 | 6.50 |
| | | 1 | 21.7 | 26.0 | 24.0 | 23.9 | 2.163 | 9.04 |
| | | 2 | 19.8 | 22.8 | 17.6 | 20.1 | 2.59 | 12.9 |
| | | 4 | 17.7 | 17.5 | 17.0 | 17.4 | 0.389 | 2.24 |
| | | 7 | 18.3 | 13.3 | 13.4 | 15.03 | 2.829 | 18.83 |
| | | 14 | 10.8 | 9.8 | 10.3 | 10.30 | 0.531 | 5.15 |

| PK parameters | Unit | Estimated Value |
|---|---|---|
| CL | mL/day/kg | 7.12 |
| Vss | mL/kg | 127 |
| V1 | mL/kg | 47.2 |
| Alpha $t_{1/2}$ | day | 0.271 |
| Beta $t_{1/2}$ | day | 12.8 |
| AUC | day*µg/mL | 421 |
| MRT | day | 17.8 |

Individual and mean serum concentration-time data of CL5 after an IV dose at 3 mg/kg in

| Dose (mg/kg) | Dose route | Sampling time (Day) | Concentration (µg/mL) Individual | | | Mean (µg/mL) | SD | CV(%) |
|---|---|---|---|---|---|---|---|---|
| 3 | IV | 0 | BQL | BQL | BQL | BQL | NA | NA |
| | | 0.00694 | 44.3 | 49.7 | 50.9 | 48.3 | 3.54 | 7.33 |
| | | 0.0417 | 37.5 | 39.6 | 33.4 | 36.8 | 3.20 | 8.67 |
| | | 0.167 | 26.0 | 26.0 | 22.5 | 24.8 | 2.00 | 8.07 |
| | | 0.333 | 22.1 | 18.7 | 21.0 | 20.6 | 1.70 | 8.27 |
| | | 1 | 12.8 | 14.1 | 14.0 | 13.6 | 0.697 | 5.12 |
| | | 2 | 12.7 | 13.6 | 11.0 | 12.4 | 1.32 | 10.6 |
| | | 4 | 11.0 | 10.5 | 9.62 | 10.4 | 0.690 | 6.66 |
| | | 7 | 9.94 | 9.09 | 10.2 | 9.75 | 0.594 | 6.09 |
| | | 14 | 4.99 | 5.42 | 5.89 | 5.43 | 0.449 | 8.26 |

| PK parameters | Unit | Estimated Values |
|---|---|---|
| CL | mL/day/kg | 13.9 |
| Vss | mL/kg | 194 |
| V1 | mL/kg | 64.0 |
| Alpha $t_{1/2}$ | day | 0.113 |
| Beta $t_{1/2}$ | day | 9.92 |
| AUC | day*µg/mL | 216 |
| MRT | day | 14.0 |

Additionally, the tumor to serum ratio of anti-CTLA4 HCAb concentration was measured in C57BL/6 mice bearing MC38 tumors. Mice were injected with 3 mg/kg anti-CTLA-4 antibodies via tail vein to measure the serum and tumor resident concentration of anti-CTLA-4 antibodies. The animals were restrained manually and approximately 100 μL of blood/time point was collected via retro-orbital puncture, the time point being 8 and 24 hr post injection. The terminal collection was via cardiac puncture. Blood samples were kept at room temperature and centrifuged at 2,000×g for 5 min at 4° C. to obtain serum samples. The serum and tumor concentrations of anti-CTLA-4 antibodies were also tested by ELISA as in step 2.

Figure 13:
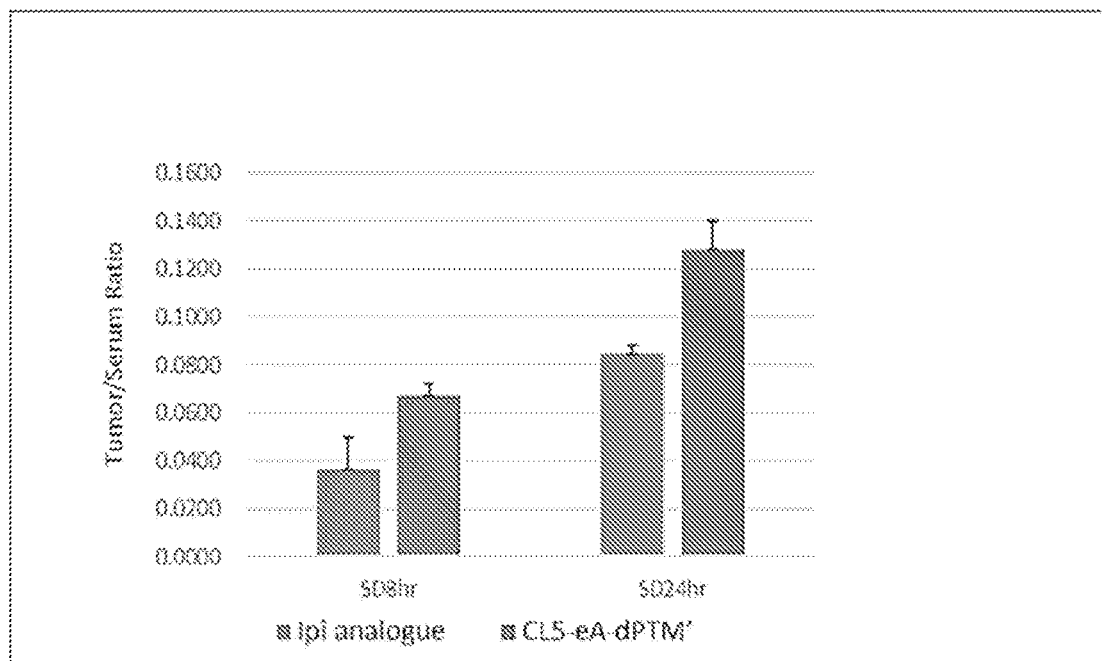
FIG. 13 shows the tumor to serum ratio of anti-CTLA4 HCAb concentration.

The tumor to serum ratio of anti-CTLA4 HCAb concentration in CL5-eA-dPTM' group was about one-fold higher than that in the Ipi analogue group, as shown in FIG. 13, which may be due to the unique feature of heavy-chain-only HCAb antibodies. The higher tumor to serum distribution may lead to a higher tumor tissue penetration of HCAb antibodies.

Example 15—Mice Bearing MC38 Tumor Better Survived with Human Anti-CTLA-4 Antibodies Cryopreserved murine colon carcinoma MC-38 cell line was recovered and cultured in DMEM medium containing 10% fetal bovine serum (FBS) and 1% Penicillin Streptomycin at 37° C. to get enough cells for tumor implantation. The cultured MC-38 cells were harvested, re-suspended in PBS at a density of $1\times10^7$ cells/ml with viability >90% and subcutaneously implanted into the right flank of 120 hCTLA-4 knock in mice (GempharmaTech). Five days after tumor inoculation, 81 mice with tumor size ranging from 26-64 mm$^3$ (average tumor size was 40 mm$^3$) were selected and assigned into 9 groups using stratified randomization with 9 mice per group based upon their tumor volumes. The treatments were started from the day of randomization (defined as D0). Group1 was treated with hIgG1 i.p. at 10 mpk on D0, D3, D6, D10, D13, D16; Group 2 was treated with CL20'-eA (sequences in Table 7) i.p. at 5.4 mpk on D0, D3, D6, D10, D13, D16; Group 3 was treated with Ipilimumab analogue i.p. at 10 mpk on D0, D3, D6, D10, D13, D16; Group 4 was treated with Ipilimumab analogue i.p. at 1 mpk on D0, D3, D6, D10, D13, D16; Group 5 was treated with CL5'-dPTM' i.p. at 5.4 mpk on D0, D3, D6, D10, D13, D16; Group 6 was treated with CL5'-dPTM' i.p. at 0.54 mpk on D0, D3, D6, D10, D13, D16; Group 7 was treated with CL5'-eA-dPTM' i.p. at 5.4 mpk on D0, D3, D6, D10, D13, D16; Group 8 was treated with CL5'-eA-dPTM' i.p. at 1.5 mpk on D0, D3, D6, D10, D13, D16; and Group 9 was treated with CL5'-eA-dPTM' i.p. at 0.54 mpk on D0, D3, D6, D10, D13, D16.

TABLE 7

Nucleic acid and amino acid sequences of clone CL20'-eA

| | SEQ ID Nos | | | | | |
|---|---|---|---|---|---|---|
| Clone ID | na-heavy chain | aa-heavy chain | aa-heavy chain variable region | aa-heavy chain CDR1 | aa-heavy chain CDR2 | aa-heavy chain CDR3 |
| CL20'-eA | 157 | 158 | 159 | 160 | 161 | 162 | na: nucleic acid;
aa: amino acid

The tumor sizes were measured three times per week during the treatment. When an individual animal reached to the termination endpoint (TV>2000 mm$^3$), it was euthanized. The time from treatment initiation to the termination was deemed as its survival time. Survival curve was plotted by Kaplan-Meier method. Median survival time (MST) was calculated for each group. Increase of life span (ILS) was calculated according to the following formula:

$$ILS(\%)=(MST_{Treatment}-MST_{Vehicle})/MST_{Vehicle}\times 100\%.$$

ILS(%)>25% will be considered as biologically significant survival benefit according to National Cancer Institute Criteria.

Relative change of body weight (RCBW) of each mouse were calculated according to the following formula: RCBW (%)=$(BW_i-BW_0)/BW_0\times 100\%$, wherein $BW_i$ referred to average body weight on Day i, and $BW_0$ referred to average bodyweight on Day 0.

Tumor volumes (TV) were calculated based on the following formula: tumor volume=(length×width$^2$)/2.

Tumor growth inhibition rate (TGI %) of each dosing group was calculated according to the following formula: TGI%=$[1-TV_i/TV_{vi}]*100\%$, wherein $TV_i$ referred to average tumor volume of a dosing group on Day i, and $TV_{vi}$ referred to average tumor volume of the vehicle group on Day i.

Mean and standard error of the mean (SEM) of mice body weight, RCBW and tumor volume of each group were calculated using Microsoft Excel 2007. Figures of body weight, relative change of body weight, tumor growth curve, and tumor growth inhibition were plotted using GraphPad Prism 5. Tumor growth between different groups was analyzed using Two-way RM ANOVA. Kaplan-Meier survival curves were analyzed using Log-Rank test. A P-value of <0.05 was considered statistically significant.

Figure 14A:
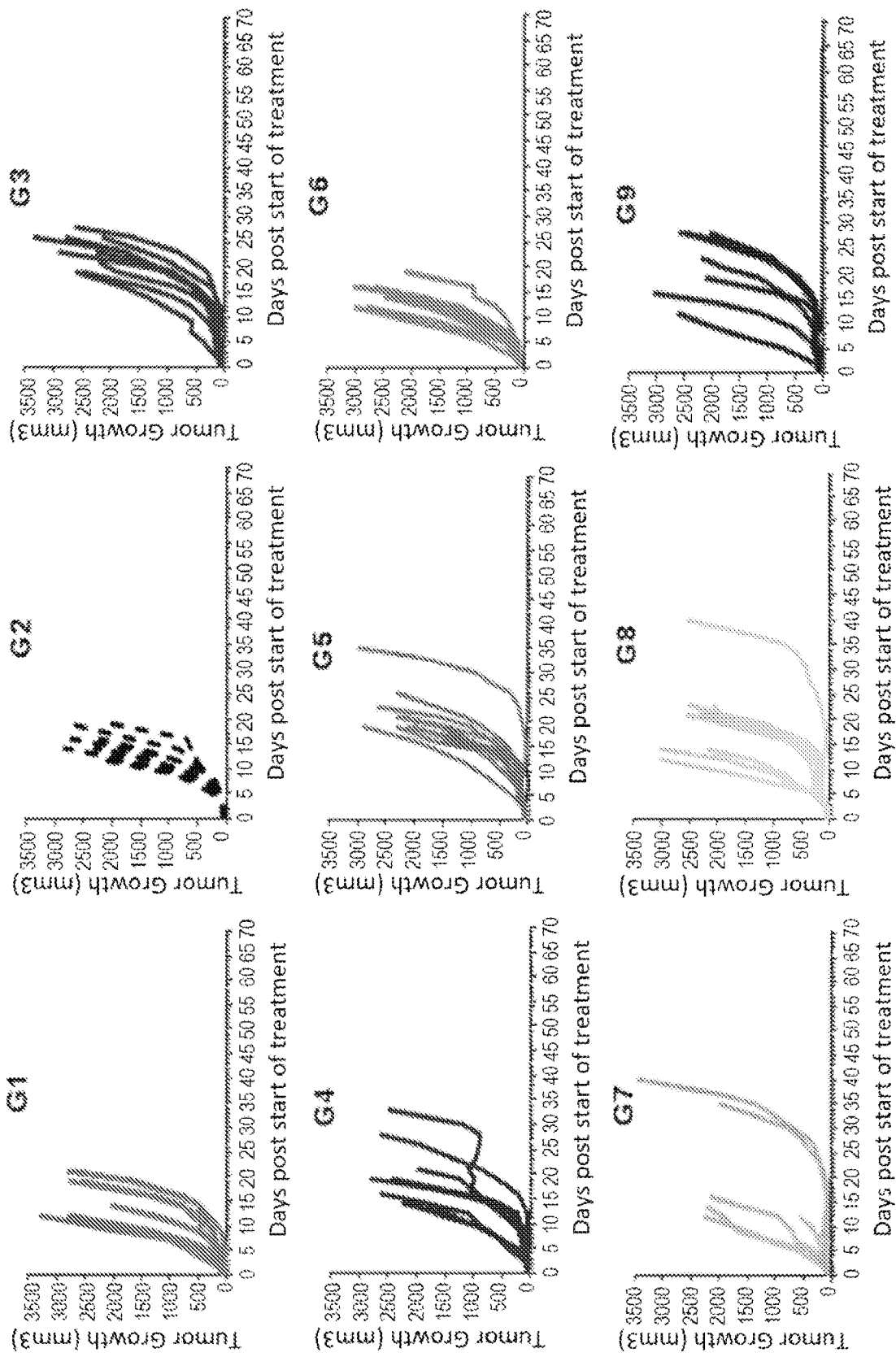
FIGS. 14A, 14B, and 14C show the anti-tumor activity of anti-CTLA-4 antibodies in MC38 tumor bearing mice. (A) Tumor growth curves of Groups 1-4 (upper panel, from left to right) and Groups 5-8 (lower panel, from left to right). (B) Time-to-End point Kaplan-Meier survival curve. (C) Mice body weights kept relatively constant along with the human anti-CTLA-4 antibody treatment. Data were expressed as Mean +SEM, N=9.
Figure 14B:
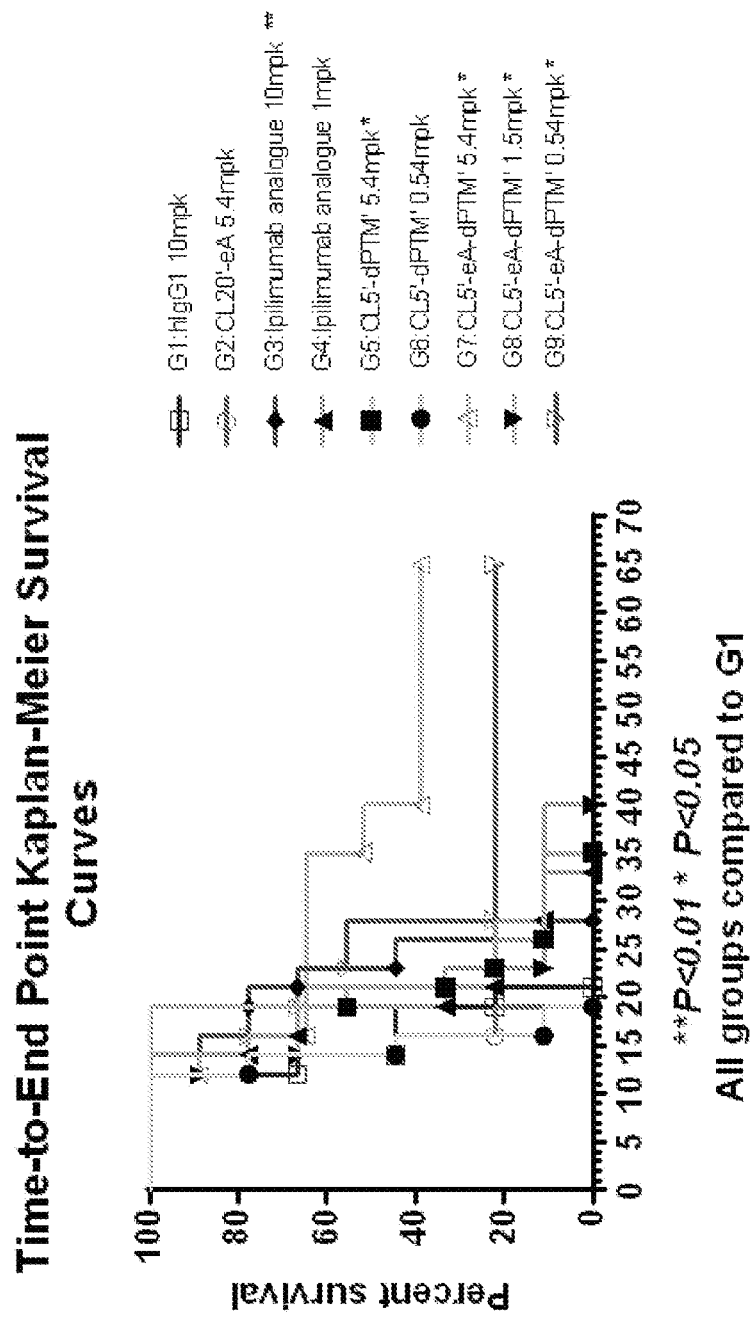
Figure 14C:
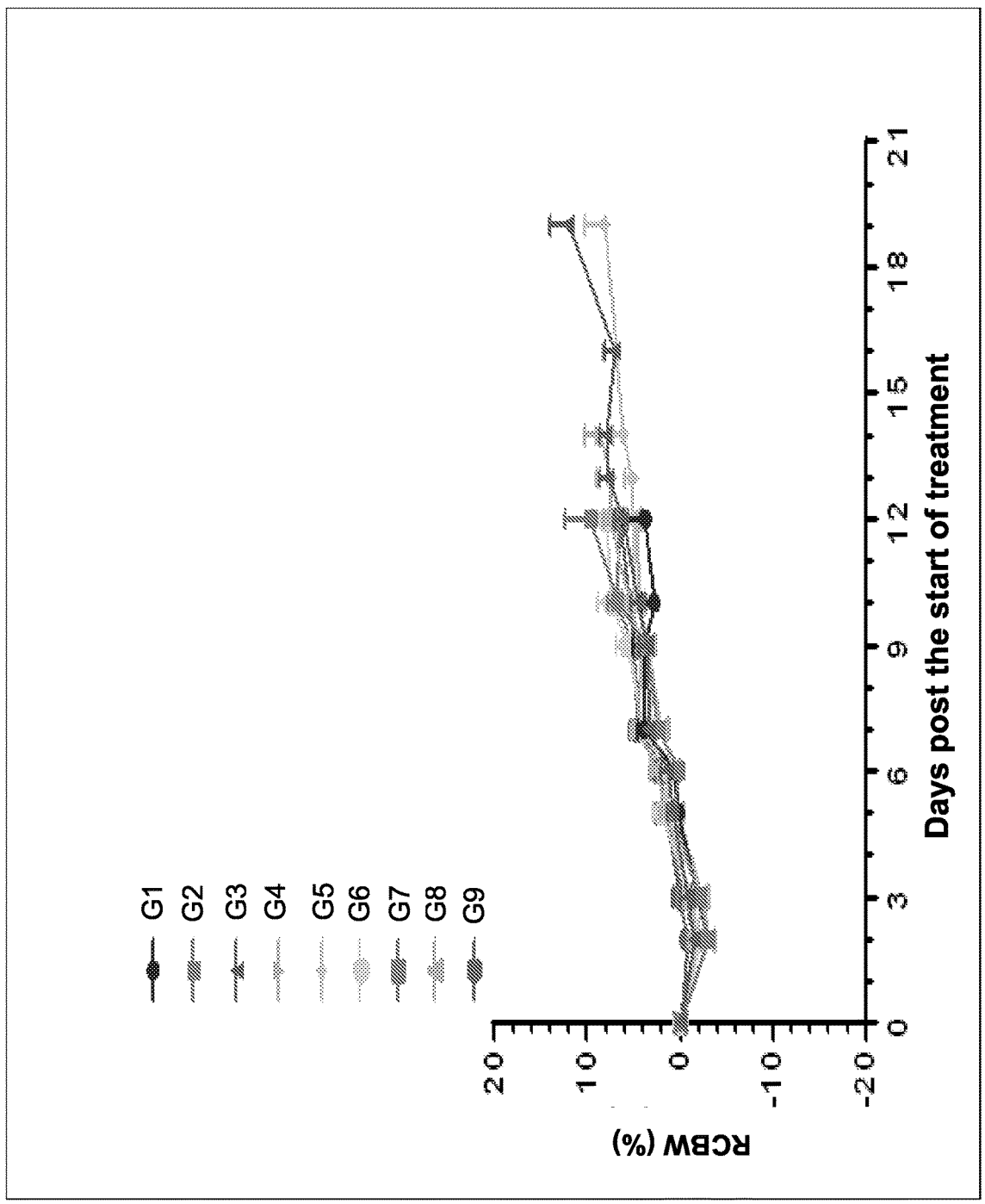

The entire study was terminated on D65. Individual tumor growth curves of each group were shown in FIG. 14A. Animal time-to-end point Kaplan-Meier survival curves were shown in FIG. 14B. All the treatments were tolerated without any adverse effect, as observed in FIG. 14C. In most of these groups, mice were all sacrificed when the tumor volume reached 2000 mm$^3$. In Group 7, 3 out of 9 mice treated with CL5'-eA-dPTM' at 5.4 mpk survived with tumor free on D65. In Group 9, 2 out of 9 mice administered with CL5'-eA-dPTM' at 0.54 mpk survived with tumor free on D65.

MST was calculated for each group and shown in Table 8. The MST of vehicle group hIgG1 at 5.4 mpk and CL20'-eA at 5.4 mpk were both 14 days. The MSTs of the treatment groups with ipilimumab analogue at 10 mpk and 1 mpk, CL5'-dPTM' at 5.4 mpk and 0.54 mpk, CL5'-eA-dPTM' at 5.4 mpk, 1.5 mpk and 0.54 mpk were 14, 23, 19, 21, 14, 40, 21 and 28 days, respectively. Also can be seen in Table 8, ILS in the treatment groups were 64.3%, 35.7%, 50%, 0%, 1850.7%, 50% and 100% compared with vehicle treatment group hIgG1. Ipilimumab analogue at 10 mpk, CL5'-dPTM' at 5.4 mpk, CL5'-eA-dPTM' at 5.4 mpk, 1.5 mpk and 0.54 mpk significantly increased median survival time. Mice treated with CL5'-eA-dPTM' at 5.4 mpk appeared a better ILS than those with the Ipilimumab analogue at 10 mpk.

TABLE 8

Survival Analysis

| Group | | MST | ILS(%) | p value |
|---|---|---|---|---|
| G1 | hIgG1, 10 mpk | 14 | — | — |
| G2 | CL20'-eA, 5.4 mpk | 14 | 0.0 | ns |
| G3 | Ipilimumab analogue, 10 mpk | 23 | 64.3 | <0.01 |
| G4 | Ipilimumab analogue, 1 mpk | 19 | 35.7 | ns |
| G5 | CL5'-dPTM', 5.4 mpk | 21 | 50.0 | <0.05 |
| G6 | CL5'-dPTM', 0.54 mpk | 14 | 0.0 | ns |
| G7 | CL5'-eA-dPTM', 5.4 mpk | 40 | 185.7 | <0.05 |
| G8 | CL5'-eA-dPTM', 1.5 mpk | 21 | 50.0 | <0.05 |
| G9 | CL5'-eA-dPTM', 0.54 mpk | 28 | 100.0 | <0.05 |

Note:
ILS = (MST$_{Gn}$ − MST$_{G1}$)/MST$_{G1}$*100%; P value are all groups compared to G1 group.

Example 16—Inhibition of MC38 Tumor Growth in hCTLA-4 Knock in Mice by Anti-CTLA-4 HCAb Cryopreserved murine colon carcinoma MC-38 cell line was recovered and cultured in DMEM medium containing 10% fetal bovine serum (FBS) and 1% Penicillin Streptomycin at 37° C. to get enough cells for tumor implantation. The cultured MC-38 cells were harvested, re-suspended in PBS at a density of 5×10$^6$ cells/ml with viability >90% and subcutaneously implanted into the right flank of 60 hCTLA-4 knock in mice. Seven days after tumor inoculation, 30 tumor-bearing mice with mean tumor size of 102 mm$^3$ were selected and randomized into 5 groups (n=6) based on their tumor sizes. The treatments were started at the day of the randomization (defined as D0). Enrolled mice were treated with hIgG1 (0.5 mpk), the Ipilimumab analogue (0.5 and 0.2 mpk) and CL5'-eA-dPTM' (0.27 and 0.1 mpk) respectively, by intraperitoneally (i.p.) on D0, D6, D9, D13, D16 and D19. Mice were monitored daily and body weights were recorded on the work days. The tumor sizes were measured twice per week during the treatment.

Relative change of body weight (RCBW), tumor volumes (TV), and tumor growth inhibition rate (TGI %) were calculated as in Example 16. Mean, standard error of the mean (SEM) of mice body weight, RCBW and tumor volume of each group were calculated using Microsoft Excel 2007. Figures of body weight, relative change of body weight, tumor growth curve, and tumor growth inhibition were plotted using GraphPad Prism 5. Tumor growth between different groups was analyzed using Two-way RM ANOVA. Kaplan-Meier survival curves were analyzed using Log-Rank test. A P-value of <0.05 was considered statistically significant.

Figure 15A:
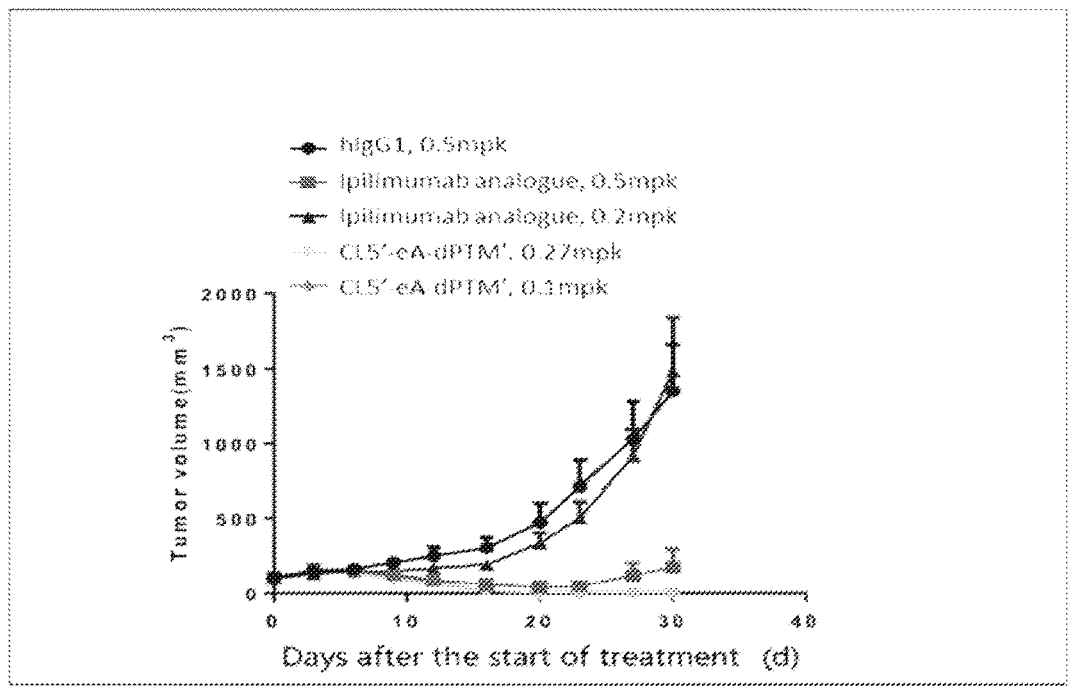
FIGS. 15A and 15B show the inhibition of tumor growth by human anti-CTLA-4 antibodies in MC38 bearing mice. (A) Tumor growth curve. (B) Mice body weights kept relatively constant along with the human anti-CTLA-4 antibody treatment. Data were expressed as Mean+SEM, N=6.
Figure 15B:
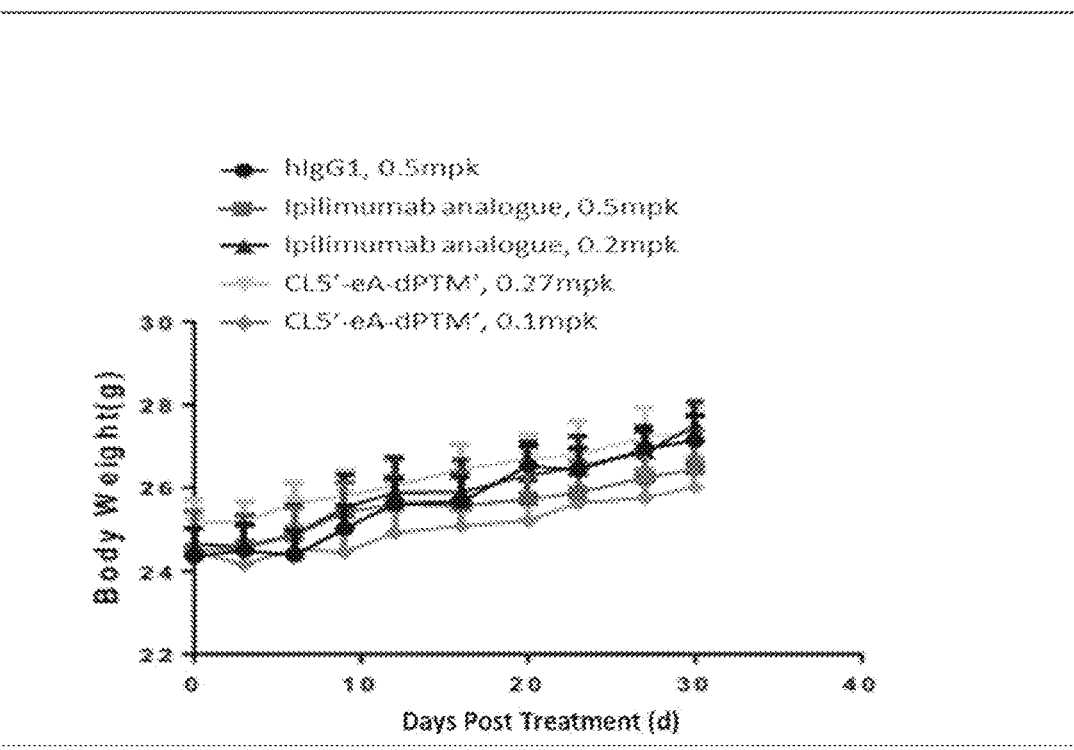

Tumor growth curves were shown in FIG. 15A. All the treatments were tolerated without any adverse effect, as observed in FIG. 15B. Mice in groups of CL5'-eA-dPTM' at 0.1 mpk and 0.27 mpk, ipilimumab analogue at 0.5 mpk showed significant tumor growth inhibition from D20 to D30 compared with mice in group of hIgG1 at 0.2 mpk. While, ipilimumab analogue treatment at 0.2 mg/kg did not show significant tumor growth inhibition compared to hIgG1 at 0.2 mpk. CL5'-eA-dPTM' promoted a better tumor growth inhibition than the Ipilimumab analogue at the same dose.

While the invention has been described in detail, and with reference to specific embodiments thereof, it will be apparent to one of ordinary skill in the art that various changes and modifications can be made therein without departing from the spirit and scope of the invention.

The invention claimed is:

1. A method of treating a disorder in a subject in need thereof, comprising administering to the subject a therapeutically effective amount of a pharmaceutical composition comprising an isolated monoclonal antibody or an antigen-binding portion thereof comprising a CD152-binding domain, and a pharmaceutical acceptable excipient, wherein the CD152-binding domain comprises an immunoglobulin heavy chain variable region comprising CDR1, CDR2, and CDR3, wherein the CDR1, CDR2, and CDR3 comprise amino acid sequences of (1) SEQ ID NOs: 4, 5 and 6, respectively;
(2) SEQ ID NOs: 10, 11 and 12, respectively;
(3) SEQ ID NOs: 16, 17 and 18, respectively;
(4) SEQ ID NOs: 22, 23 and 24, respectively;
(5) SEQ ID NOs: 28, 29 and 30, respectively;
(6) SEQ ID NOs: 34, 35 and 36, respectively;
(7) SEQ ID NOs: 40, 41 and 42, respectively;
(8) SEQ ID NOs: 46, 47 and 48, respectively;
(9) SEQ ID NOs: 52, 53 and 54, respectively;
(10) SEQ ID NOs: 58, 59 and 60, respectively;
(11) SEQ ID NOs: 64, 65 and 66, respectively;
(12) SEQ ID NOs: 94, 95 and 96, respectively;

(13) SEQ ID NOs: 100, 101 and 102, respectively; or
(14) SEQ ID NOs: 184, 185 and 186, respectively; and
wherein the disorder is a cancer or an autoimmune disease.

2. The method of claim 1, wherein the antibody is a heavy-chain-only antibody.

3. The method of claim 1, wherein the antibody comprises two immunoglobulin heavy chains or consists of two immunoglobulin heavy chains.

4. The method of claim 1, wherein the immunoglobulin heavy chain variable region comprises an amino acid sequence having at least 90% identity to SEQ ID NO: 3, 9, 15, 21, 27, 33, 39, 45, 51, 57, 63, 69, 75, 81, 87, 93, 99, 105, or 183.

5. The method of claim 3, wherein at least one of the two immunoglobulin heavy chains comprises an amino acid sequence having at least 90% identity to SEQ ID NO: 2, 8, 14, 20, 26, 32, 38, 44, 50, 56, 62, 68, 74, 80, 86, 92, 98, 104, 110, 116, 122, 128, 134, 140, 146, 152, 158, 164, 170, 176, 182, or 188.

6. The method of claim 1, wherein the antibody is a human, humanized, or chimeric antibody.

7. The method of claim 1, wherein the disorder is a cancer.

8. The method of claim 7, wherein the cancer is selected from the group consisting of leukemia, lymphoma, CLL, small lymphocytic lymphoma, marginal cell B-Cell lymphoma, Burkett's Lymphoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, and head and neck cancer.

9. The method of claim 7, further comprising administering to the subject an additional therapeutic agent.

10. The method of claim 9, wherein the additional therapeutic agent is an anti-cancer agent.

11. The method of claim 9, wherein the additional therapeutic agent is an immunostimulatory antibody or a costimulatory antibody.

12. The method of claim 11, wherein the immunostimulatory antibody is selected from the group consisting of an anti-PD-1 antibody, an anti-PD-L1 antibody, an anti-LAG-3 antibody, an anti-TIM 3 antibody, an anti-STAT3 antibody, and an anti-ROR1 antibody.

13. The method of claim 11, wherein the costimulatory antibody is an anti-CD137 antibody or an anti-GITR antibody.

14. The method of claim 9, wherein the additional therapeutic agent is Ipilimumab.

15. The method of claim 1, wherein the disorder is an autoimmune disease.

16. The method of claim 1, wherein the CDR1, CDR2, and CDR3 comprise the amino acid sequences of SEQ ID NO: 184, 185 and 186 respectively, and wherein the disorder is a cancer.

17. The method of claim 16, wherein the immunoglobulin heavy chain variable region comprises the amino acid sequence of SEQ ID NO 183.

18. The method of claim 16, wherein the antibody comprises two immunoglobulin heavy chains, and each of the two immunoglobulin heavy chains comprises the amino acid sequence of SEQ ID NO: 182.

19. The method of claim 16, wherein the cancer is selected from the group consisting of melanoma, liver cancer, renal cell carcinoma, and lung cancer.

20. The method of claim 18, wherein the cancer is selected from the group consisting of melanoma, liver cancer, renal cell carcinoma, and lung cancer.

\* \* \* \* \*